US009683237B2

(12) United States Patent
Rao et al.

(10) Patent No.: US 9,683,237 B2
(45) Date of Patent: *Jun. 20, 2017

(54) MULTIPLE TARGETED RNAI FOR THE TREATMENT OF CANCERS

(71) Applicants: Strike Bio, Inc, Dallas, TX (US); Baylor College of Medicine, Houston, TX (US)

(72) Inventors: Donald Rao, Dallas, TX (US); John Nemunaitis, Cedar Hill, TX (US); Bert W. O'Malley, Houston, TX (US); David Lonard, Pearland, TX (US)

(73) Assignees: STRIKE BIO, INC., Dallas, TX (US); BAYLOR COLLEGE OF MEDICINE, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/696,144

(22) Filed: Apr. 24, 2015

(65) Prior Publication Data

US 2015/0307885 A1    Oct. 29, 2015

Related U.S. Application Data

(60) Provisional application No. 61/984,614, filed on Apr. 25, 2014.

(51) Int. Cl.
*C12N 15/113*  (2010.01)
*A61K 31/7088* (2006.01)
*A61K 45/06* (2006.01)
*C12Q 1/68* (2006.01)
(Continued)

(52) U.S. Cl.
CPC ...... *C12N 15/1135* (2013.01); *A61K 31/7088* (2013.01); *A61K 31/713* (2013.01);
(Continued)

(58) Field of Classification Search
CPC .................................................. C12N 15/113
See application file for complete search history.

(56) References Cited

U.S. PATENT DOCUMENTS 7,893,034 B2     2/2011  Slack et al.
9,353,373 B2 *   5/2016  Rao ..................... C12N 15/1135
(Continued)

OTHER PUBLICATIONS

Huang H. et al. "Profiling of mismatch discrimination in RNAi enabled rational design of allele-specific siRNAs." Nucleic Acids Res. Dec. 2009; vol. 37(22):7560-9.
(Continued)

*Primary Examiner* — J. E. Angell
(74) *Attorney, Agent, or Firm* — Edwin S. Flores; Chalker Flores, LLP

(57) ABSTRACT

The present invention includes compositions and methods for making and using a RNAi capable of reducing expression of two or more genes, comprising: a first RNAi molecule that reduces the expression of a first target gene; a second RNAi molecule that reduces the expression of the first or a second target gene; and optionally a third RNAi molecule that reduces the expression of the first, the second, or a third target gene, wherein the RNAi molecules reduce the expression level of, e.g., mutated KRAS, SRC-3, EGFR, PIK3, NCOA3, or ERalpha1, and can be, e.g., miRNAs, shRNAs, or bifunctional shRNAs.

10 Claims, 7 Drawing Sheets

(51) Int. Cl.
  *G01N 33/50* (2006.01)
  *A61K 31/7105* (2006.01)
  *A61K 31/713* (2006.01)
  *A61K 9/127* (2006.01)
  *A61K 9/00* (2006.01)

(52) U.S. Cl.
  CPC .......... *A61K 31/7105* (2013.01); *A61K 45/06* (2013.01); *C12N 15/1136* (2013.01); *C12N 15/1137* (2013.01); *C12N 15/1138* (2013.01); *C12Q 1/6886* (2013.01); *G01N 33/5011* (2013.01); *A61K 9/0019* (2013.01); *A61K 9/127* (2013.01); *C12N 2310/14* (2013.01); *C12N 2310/531* (2013.01); *C12N 2320/31* (2013.01); *C12Q 2600/136* (2013.01); *C12Q 2600/158* (2013.01); *G01N 2333/914* (2013.01)

(56) References Cited

U.S. PATENT DOCUMENTS

| | | |
|---|---|---|
| 2012/0142764 A1 | 6/2012 | Seol |
| 2013/0064881 A1 | 3/2013 | Nemunaitis et al. |
| 2013/0078719 A1* | 3/2013 | Rao .................. A61K 48/00 435/366 |
| 2013/0266639 A1 | 10/2013 | Rao et al. |

OTHER PUBLICATIONS

Schwarz DS. et al. "Designing siRNA that distinguish between genes that differ by a single nucleotide." PLoS Genet. Sep. 8, 2006;2(9):e140.

Brummelkamp TR. et al. "Stable suppression of tumorigenicity by virus-mediated RNA interference." Cancer Cell. Sep. 2002;2(3):243-7.

Fleming JB et al. "Molecular consequences of silencing mutant K-ras in pancreatic cancer cells: justification for K-ras-directed therapy." Mol Cancer Res. Jul. 2005;3(7):413-23.

Zhang Z. et al. "Knockdown of mutant K-ras expression by adenovirus-mediated siRNA inhibits the in vitro and in vivo growth of lung cancer cells." Cancer Biol Ther. Nov. 2006;5(11):1481-6.

Smakman N. et al. "Dual effect of Kras(D12) knockdown on tumorigenesis: increased immune-mediated tumor clearance and abrogation of tumor malignancy." Oncogene. Dec. 15, 2005;24(56):8338-42.

Zhang YA. et al. "Antitumor activity of an oncolytic adenovirus-delivered oncogene small interfering RNA." Cancer Res. Oct. 1, 2006;66(19):9736-43.

Sierant M. et al. "Specific Silencing of L392V PSEN1 Mutant Allele by RNA Interference." Int J Alzheimers Dis. Apr. 7, 2011;2011:809218.

De Yñigo-Mojado L. et al. "Efficient allele-specific targeting of LRRK2 R1441 mutations mediated by RNAi." PLoS One. 2011;6(6):e21352.

Takahashi M. et al "Tailor-made RNAi knockdown against triplet repeat disease-causing alleles." Proc Natl Acad Sci U S A. Dec. 14, 2010;107(50):21731-6.

Pfister EL. et al. "Five siRNAs targeting three SNPs may provide therapy for three-quarters of Huntington's disease patients." Curr Biol. May 12, 2009;19(9):774-8.

Rao D. et al. "Enhanced target gene knockdown by a bifunctional shRNA: a novel approach of RNA interference." Cancer Gene Ther. Nov. 2010;17(11):780-91.

* cited by examiner

MULTIPLE TARGETED RNAI FOR THE TREATMENT OF CANCERS

CROSS-REFERENCE TO RELATED APPLICATIONS

This non-provisional Patent Application claims priority to U.S. Provisional Patent Application Ser. No. 61/984,614 filed Apr. 25, 2014, entitled "Multiple Targeted Bi-Functional SHRNA For the Treatment of Lung Cancer," the contents of which is incorporated by reference herein in its entirety.

TECHNICAL FIELD OF THE INVENTION

The present invention relates in general to the field of cancer treatment, and more particularly, to an RNAi construct that is used for the treatment of cancer.

STATEMENT OF FEDERALLY FUNDED RESEARCH

None.

REFERENCE TO A SEQUENCE LISTING

The present application includes a Sequence Listing filed separately in electronic format as required by 37 C.F.R. §1.821-1825.

BACKGROUND OF THE INVENTION

Without limiting the scope of the invention, its background is described in connection with K-ras and lung cancer.

The KRAS (Kirsten-ras) oncogene is mutated in a significant proportion of pancreatic ductal adenocarcinoma (PDAC), colorectal and non-small-cell lung cancers (NSCLC). In the majority of PDAC (70-90%) patients carrying KRAS mutations, the five-year survival rate is less than 5%. KRAS is a member of guanine nucleotide-binding protein family and is an integral component of multiple intracellular signaling pathways including epidermal growth factor receptor (EGFR). The overwhelming majority of mutations in KRAS are single nucleotide somatic mutations resulting in single amino acid substitutions at codons 12 or 13. The G12D, G12V, G12R and G12C KRAS mutations comprise >90% of KRAS mutations found in PADC patients. KRAS mutations essentially result in constitutively active KRAS and unregulated downstream signaling.

Targeted agents such as the antibody Cetuximab (in colorectal cancer) and the small molecular inhibitor vemurafenib (in BRAF mutant melanoma), perform poorly in patients with KRAS mutations. Consequently an effective cancer therapeutic strategy requires KRAS mutation selectivity sparing wild-type functionality. There remains a great need for compositions, methods and treatments for cancers with KRAS mutations.

U.S. Pat. No. 7,893,034, issued to Slack, et al., is entitled "Regulation of oncogenes by microRNAs." Briefly, these inventors describe targeting naturally occurring miRNAs that regulate human oncogenes and methods of use thereof. Suitable nucleic acids for use in the methods and compositions described by the inventors are said to include, but not be limited to, pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA. The inventors also discuss compositions containing nucleic acids are administered to a patient in need of treatment or prophylaxis of at least one symptom or manifestation of cancer. In one specific embodiment, the compositions are said to be administered in an effective amount to inhibit gene expression of one or more oncogenes. Methods for treatment or prevention of at least one symptom or manifestation of cancer are also described.

SUMMARY OF THE INVENTION

In one embodiment, the present invention includes a bifunctional shRNA capable of reducing expression of three or more genes, comprising: a first bifunctional RNA molecule that reduces the expression of a KRAS; a second bifunctional RNA molecule that reduces the expression of a steroid receptor coactivator-3 (SRC-3); and a third bifunctional RNA molecule that reduces the expression of a Epidermal Growth Factor Receptor (EGFR), wherein the bifunctional RNA molecules are capable of activating a cleavage-dependent and a cleavage-independent RNA-induced silencing complex for reducing the expression level of mutated K-ras, SRC-3 and EGFR. In one aspect, the bifunctional shRNA is spliced into a vector. In another aspect, the bifunctional shRNA is spliced into a vector defined by SEQ ID NOS: 1, 3, 42 or 43. In another aspect, the bifunctional shRNA comprises at least one sequence defined by SEQ ID NOS: 2, 4, 40 or 41. In another aspect, at least one target site for the first bifunctional RNA is a mutated KRAS gene defined further as a human KRAS gene having at least one of a G12C, a G12D, a G12V, or a G12R mutation. In another aspect, the expression of normal RAS is not reduced below functional physiological levels by the first bifunctional RNA molecule. In another aspect, at least one of the SRC-3 or EGFR is a normal human gene.

Another embodiment of the present invention includes an expression vector comprising: a promoter; and a nucleic acid insert operably linked to the promoter, wherein the insert comprises: a first bifunctional RNA molecule that reduces the expression of a mutated KRAS; a second bifunctional RNA molecule that reduces the expression of a SRC-3; and a third bifunctional RNA molecule that reduces the expression of a Epidermal Growth Factor Receptor (EGFR), wherein the bifunctional RNA molecule is capable of activating a cleavage-dependent and a cleavage-independent RNA-induced silencing complex for reducing the expression level of mutated KRAS, SRC-3 and EGFR, wherein the one or more shRNA comprise a bifunctional RNA molecule that activates a cleavage-dependent and a cleavage-independent RNA-induced silencing complex for reducing the expression level of KRAS, SRC-3 and EGFR. In one aspect, the vector comprises at least one sequence defined by SEQ ID NOS: 1, 3, 42 or 43. In another aspect, the bifunctional RNA molecule comprises SEQ ID NO: 2, 4, 40 or 41. In another aspect, a sequence arrangement for the first, second and third bifunctional shRNA comprises a 5' stem arm-19 nucleotide target, which is K-ras-TA-15 nucleotide loop-19 nucleotide target complementary sequence-3'stem arm-Spacer-5' stem arm-19 nucleotide target variant-TA-15 nucleotide loop-19 nucleotide target complementary sequence-3'stem arm. In another aspect, the vector comprises at least one sequence selected from SEQ ID NO: 1 or 2. In another aspect, the nucleic acid insert comprises 1, 2, 3, 4, 5, 6, 7, 8, 9, 10, 11, 12, 13, 14, 15, 16, 17, 18, 20, 21, 25, 50, 75, or 100 copies of bifunctional shRNAs inserts capable of reducing an expression of one or more mutated KRAS, and EGFR and SRC-3. In another aspect, at least one of the SRC-3 or EGFR is a normal human gene.

Yet another embodiment of the present invention is a therapeutic delivery system comprising: a therapeutic agent carrier; and an expression vector comprising a promoter and a nucleic acid insert operably linked to the promoter, the nucleic acid insert encoding: a first bifunctional RNA molecule that reduces the expression of a mutated KRAS; a second bifunctional RNA molecule that reduces the expression of a SRC-3; and a third bifunctional RNA molecule that reduces the expression of a Epidermal Growth Factor Receptor (EGFR), wherein the bifunctional RNA molecule is capable of activating a cleavage-dependent and a cleavage-independent RNA-induced silencing complex for reducing the expression level of mutated KRAS, SRC-3 and EGFR, wherein the one or more shRNA comprise a bifunctional RNA molecule that activates a cleavage-dependent and a cleavage-independent RNA-induced silencing complex for reducing the expression level of KRAS, SRC-3 and EGFR. In another aspect, the therapeutic agent carrier is a compacted DNA nanoparticle, or a compacted DNA nanoparticle with one or more polycations. In another aspect, the one or more polycations is a 10 kDA polyethylene glycol (PEG)-substituted cysteine-lysine 3-mer peptide ($CK_{30}PEG10k$). In another aspect, the compacted DNA nanoparticles are further encapsulated in at least one of a liposome, a reversibly masked liposome, or a bilamellar invaginated vesicle (BIV). In another aspect, the vector comprises at least one sequence defined by SEQ ID NOS: 1, 3, 42 or 43. In another aspect, the nucleic acid insert comprises SEQ ID NO: 2, 4, 40 or 41.

Yet another embodiment of the invention includes a method to deliver one or more shRNAs to a target tissue expressing a KRAS, SRC-3 and EGFR gene comprising the steps of: preparing an expression vector comprising a promoter and a nucleic acid insert operably linked to the promoter that encodes the one or more shRNA, wherein the one or more shRNA comprise a nucleic acid insert operably linked to the promoter, wherein the insert comprises: a first bifunctional RNA molecule that reduces the expression of a mutated SRC-3; a second bifunctional RNA molecule that reduces the expression of a SRC-3; and a third bifunctional RNA molecule that reduces the expression of a Epidermal Growth Factor Receptor (EGFR), wherein the bifunctional RNA molecule is capable of activating a cleavage-dependent and a cleavage-independent RNA-induced silencing complex for reducing the expression level of mutated KRAS, SRC-3 and EGFR, wherein the one or more shRNA comprise a bifunctional RNA molecule that activates a cleavage-dependent and a cleavage-independent RNA-induced silencing complex for reducing the expression level of KRAS, SRC-3 and EGFR; combining the expression vector with a therapeutic agent carrier, wherein the therapeutic agent carrier comprises a liposome; and administering a therapeutically effective amount of the expression vector and therapeutic agent carrier complex to a patient in need thereof. In one aspect, the therapeutic agent carrier is a compacted DNA nanoparticle. In another aspect, the DNA nanoparticle is compacted with one or more polycations, wherein the one or more polycations comprise a 10 kDA polyethylene glycol (PEG)-substituted cysteine-lysine 3-mer peptide ($CK_{30}PEG10k$) or a 30-mer lysine condensing peptide. In another aspect, the compacted DNA nanoparticles are further encapsulated in a liposome, wherein the liposome is a bilamellar invaginated vesicle (BIV) that comprises one or more receptor targeting moieties.

Yet another embodiment of the invention includes a method of suppressing a tumor cell growth in a human subject comprising the steps of: identifying the human subject in need for suppression of the tumor cell growth; and administering an expression vector in a therapeutic agent carrier complex to the human subject in an amount sufficient to suppress the tumor cell growth, wherein the expression vector comprises a nucleic acid insert operably linked to the promoter, wherein the insert comprises: a first bifunctional RNA molecule that reduces the expression of a mutated KRAS gene; a second bifunctional RNA molecule that reduces the expression of a SRC-3 gene; and a third bifunctional RNA molecule that reduces the expression of a Epidermal Growth Factor Receptor (EGFR) gene, wherein the bifunctional RNA molecule is capable of activating a cleavage-dependent and a cleavage-independent RNA-induced silencing complex for reducing the expression level of mutated KRAS, SRC-3 and EGFR, and wherein the inhibition results in an apoptosis, an arrested proliferation, or a reduced invasiveness of the tumor cells. In one aspect, the therapeutic agent carrier comprises a bilamellar invaginated vesicle (BIV). In another aspect, the therapeutic agent carrier comprises one or more receptor targeting moieties that comprise small molecule bivalent beta-turn mimics. In another aspect, the step of administering is selected from the group consisting of intratumoral, subcutaneous, intravenous, intraperitoneal, intramuscular, and intravenous injection. In another aspect, the step of administering comprises injecting with a DNA:lipoplex. In another aspect, the tumor cell growth expresses a mutated KRAS. In another aspect, the tumor cell growth is a lung cancer. In another aspect, the method further comprises a combination therapy with a second anti-neoplasmic agent.

Yet another embodiment of the invention includes a method of evaluating a candidate drug believed to be useful in treating a lung cancer, the method comprising: (a) measuring one or more of the following: the level of expression of at least a wild-type KRAS and one or more mutated KRAS, EGFR and SRC-3 genes in the lung cancer cells or tissues; the level of expression of a candidate gene or a group of candidate genes in an cellular environment with the lowered expression of one or more mutated KRAS, EGFR and SRC-3 genes in the lung cancer cells or tissues; the effect of a candidate drug on the phenotype of such cells comprised of lowered expression of one or more mutated KRAS, EGFR and SRC-3 genes in the lung cancer cells or tissues; (b) administering a candidate drug to a first subset of said lung cancer cells or tissues, and a placebo to a second subset of said lung cancer cells or tissues; (c) repeating step (a) after the administration of the candidate drug or the placebo; and (d) determining if the candidate drug is effective in producing determined phenotype in an cellular environment with reduced expression of mutated KRAS, EGFR and SRC-3 as compared to KRAS mutant, EGFR and SRC-3 expressing cellular environment that is statistically significant as compared to any reduction occurring in the second subset of lung cancer cells or tissues, wherein a statistically significant reduction indicates that the candidate drug is useful in treating lung cancer. In another aspect, the cells or tissue further express one or more detectable genes have modified to comprise a wild-type RAS and one or more mutated KRAS, wherein the level of expression of the detectable label correlates with the effect of the candidate substance on the wild-type RAS and one or more mutated KRAS.

Yet another embodiment of the invention includes a method of suppressing the growth of tumor cells in a human subject comprising the steps of: obtaining a tumor cell sample from the human subject; identifying one or more target gene or genes in the human subject in need for suppression to prevent tumor cell growth; constructing a expression vector that comprises an insert that expresses two or more RNAi nucleic acid segments that specifically target the gene or genes identified in the tumor cell sample; wherein the insert comprises: a first and a second RNAi nucleic acid that reduces the expression of the same or different target gene or genes identified in the tumor cell; administering the expression vector in a therapeutic agent carrier complex to the human subject in an amount sufficient to express the two or more RNAi nucleic acid segments; and determining whether the gene or genes have been knocked-down by the expression vector in the target tumor cells, wherein the inhibition results in an apoptosis, an arrested proliferation, or a reduced invasiveness of the tumor cells. In one aspect, the RNAi is selected from at least one of an miRNA, and shRNA, and siRNA, or a bi-shRNA. In another aspect, both the first and the second nucleic acids encode a bifunctional-shRNA. In another aspect, the at least one of the first or the second nucleic acid targets K-RAS and is selected from SEQ ID NOS: 5-26, SEQ ID NOS: 27-36, SEQ ID NOS: 38-39, SEQ ID NOS: 40-41, SEQ ID NOS: 42-43, SEQ ID NOS: 48-49, or SEQ ID NOS:50-126. In another aspect, the at least one of the first or the second nucleic acid targets SRC-3 and is selected from SEQ ID NOS: 27-36. In another aspect, the insert further comprises 3, 4, 5, 6, 7, 8, 9, 11, 10, 12, 13, 14, 15, 16, 17, 18, 20, 21, 25, 50, 75, or 100 copies of RNAi inserts capable of reducing an expression of one or more mutated or normal genes.

In another embodiment, the present invention includes a bifunctional shRNA composition capable of reducing expression of three or more genes, comprising: a first bifunctional RNA molecule that reduces the expression of a first gene target; a second bifunctional RNA molecule that reduces the expression of a second gene target; and a third bifunctional RNA molecule that reduces the expression of a third gene target, wherein each of the bifunctional RNA molecules are capable of activating a cleavage-dependent and a cleavage-independent RNA-induced silencing complex for reducing the expression level of the first, second and third gene target. In another aspect, each of the bifunctional shRNAs is spliced into a vector. In another aspect, the composition is defined further as a vector defined by SEQ ID NOS: 1, 3, 46 or 47. In another aspect, the bifunctional shRNAs comprises at least one nucleic acid sequence defined by SEQ ID NOS: 2, 4, 44 or 45. In another aspect, the at least one target site for the first bifunctional RNA selectively targets a mutated KRAS gene defined further as a human KRAS gene having at least one of a G12C, a G12D, a G12V, or a G12R mutation. In another aspect, the at least first, second or third bifunctional RNA molecule is selected from SEQ ID NOS: 5-26, SEQ ID NOS: 27-36, SEQ ID NOS: 38-39, SEQ ID NOS: 40-41, SEQ ID NOS: 42-43, SEQ ID NOS: 48-49, or SEQ ID NOS:50-126. In another aspect, the expression of normal RAS is not reduced below functional physiological levels by the first bifunctional RNA molecule. In another aspect, the at least one of SRC-3 or EGFR is a normal human gene.

In another embodiment, the present invention includes an expression vector comprising: a promoter; and a nucleic acid insert operably linked to the promoter, wherein the insert comprises: a first bifunctional RNA molecule that reduces the expression of s first target gene; a second bifunctional RNA molecule that reduces the expression of a second target gene; and a third bifunctional RNA molecule that reduces the expression of a third target gene, wherein the bifunctional RNA molecule is capable of activating a cleavage-dependent and a cleavage-independent RNA-induced silencing complex for reducing the expression level of the first, second and third target genes, wherein the one or more shRNA comprise a bifunctional RNA molecule that activates a cleavage-dependent and a cleavage-independent RNA-induced silencing complex for reducing the expression level of the first, second and third target genes. In another aspect, the composition is defined further as a vector defined by SEQ ID NOS: 1, 3, 46 or 47. In another aspect, the bifunctional shRNAs comprises at least one nucleic acid sequence defined by SEQ ID NOS: 2, 4, 44 or 45. In another aspect, the at least one gene target comprises a bifunctional shRNA that selectively targets a mutated KRAS gene defined further as a human KRAS gene having at least one of a G12C, a G12D, a G12V, or a G12R mutation. In another aspect, the at least the first, second or third bifunctional RNA molecule is selected from SEQ ID NOS: 5-26, SEQ ID NOS: 27-36, SEQ ID NOS: 38-39, SEQ ID NOS: 40-41, SEQ ID NOS: 42-43, SEQ ID NOS: 48-49, or SEQ ID NOS:50-126. In another aspect, the nucleic acid insert comprises 1, 2, 3, 4, 5, 6, 7, 8, 9, 11, 10, 12, 13, 14, 15, 16, 17, 18, 20, 21, 25, 50, 75, or 100 copies of bifunctional shRNAs inserts capable of reducing an expression of one or more mutated or normal genes.

In another embodiment, the present invention includes a therapeutic delivery system comprising: a therapeutic agent carrier; and an expression vector comprising a promoter and a nucleic acid insert operably linked to the promoter, the nucleic acid insert encoding: a first bifunctional RNA molecule that reduces the expression of a first gene target; a second bifunctional RNA molecule that reduces the expression of a second gene target; and a third bifunctional RNA molecule that reduces the expression of a third gene target, wherein each of the bifunctional RNA molecules are capable of activating a cleavage-dependent and a cleavage-independent RNA-induced silencing complex for reducing the expression level of the first, second and third gene target. In one aspect, the composition is defined further as a vector defined by SEQ ID NOS: 1, 3, 46 or 47. In another aspect, the bifunctional shRNAs comprises at least one nucleic acid sequence defined by SEQ ID NOS: 2, 4, 44 or 45. In another aspect, the at least one gene target comprises a bifunctional shRNA that selectively targets a mutated KRAS gene defined further as a human KRAS gene having at least one of a G12C, a G12D, a G12V, or a G12R mutation. In another aspect, the at least first, second or third bifunctional RNA molecule is selected from SEQ ID NOS: 5-26, SEQ ID NOS: 27-36, SEQ ID NOS: 38-39, SEQ ID NOS: 40-41, SEQ ID NOS: 42-43, SEQ ID NOS: 48-49, or SEQ ID NOS:50-126. In another aspect, the nucleic acid insert comprises 1, 2, 3, 4, 5, 6, 7, 8, 9, 11, 10, 12, 13, 14, 15, 16, 17, 18, 20, 21, 25, 50, 75, or 100 copies of bifunctional shRNAs inserts capable of reducing an expression of one or more mutated or normal genes.

In another embodiment, the present invention includes a method to deliver one or more shRNAs to a target tissue expressing a KRAS, SRC-3 and EGFR gene comprising the steps of: preparing an expression vector comprising a promoter and a nucleic acid insert operably linked to the promoter that encodes the one or more shRNA, wherein the one or more shRNA comprise a nucleic acid insert operably linked to the promoter, wherein the insert comprises: a first bifunctional RNA molecule that reduces the expression of a first gene target; a second bifunctional RNA molecule that reduces the expression of a second gene target; and a third bifunctional RNA molecule that reduces the expression of a third gene target, wherein each of the bifunctional RNA molecules are capable of activating a cleavage-dependent and a cleavage-independent RNA-induced silencing complex for reducing the expression level of the first, second and third gene target; combining the expression vector with a therapeutic agent carrier, wherein the therapeutic agent carrier comprises a liposome; and administering a therapeutically effective amount of the expression vector and therapeutic agent carrier complex to a patient in need thereof. In another aspect, the composition is defined further as a vector defined by SEQ ID NOS: 1, 3, 46 or 47. In another aspect, the bifunctional shRNAs comprises at least one nucleic acid sequence defined by SEQ ID NOS: 2, 4, 44 or 45. In another aspect, the at least one gene target comprises a bifunctional shRNA that selectively targets a mutated KRAS gene defined further as a human KRAS gene having at least one of a G12C, a G12D, a G12V, or a G12R mutation. In another aspect, the at least first, second or third bifunctional RNA molecule is selected from SEQ ID NOS: 5-26, SEQ ID NOS: 27-36, SEQ ID NOS: 38-39, SEQ ID NOS: 40-41, SEQ ID NOS: 42-43, SEQ ID NOS: 48-49, or SEQ ID NOS:50-126. In another aspect, the nucleic acid insert comprises 1, 2, 3, 4, 5, 6, 7, 8, 9, 10, 11, 12, 13, 14, 15, 16, 17, 18, 20, 21, 25, 50, 75, or 100 copies of bifunctional shRNAs inserts capable of reducing an expression of one or more mutated or normal genes.

In another embodiment, the present invention includes a method of suppressing a tumor cell growth in a human subject comprising the steps of: identifying the human subject in need for suppression of the tumor cell growth; and administering an expression vector in a therapeutic agent carrier complex to the human subject in an amount sufficient to suppress the tumor cell growth, wherein the expression vector comprises a nucleic acid insert operably linked to the promoter, wherein the insert comprises: a first bifunctional RNA molecule that reduces the expression of a mutated KRAS gene; a second bifunctional RNA molecule that reduces the expression of a SRC-3 gene; and a third bifunctional RNA molecule that reduces the expression of a Epidermal Growth Factor Receptor (EGFR) gene, wherein the bifunctional RNA molecule is capable of activating a cleavage-dependent and a cleavage-independent RNA-induced silencing complex for reducing the expression level of mutated KRAS, SRC-3 and EGFR, and wherein the inhibition results in an apoptosis, an arrested proliferation, or a reduced invasiveness of the tumor cells. In another aspect, the nucleic acid insert comprises SEQ ID NO: 2, 4, 42, or 43. In another aspect, the at least one nucleic acid insert against K-RAS is selected from SEQ ID NOS: 5-26. In another aspect, the at least one nucleic acid insert against SRC-3 is selected from SEQ ID NOS: 27-36. In another aspect, the at least one nucleic acid insert against EGFR is selected from SEQ ID NO: 48-49. In another aspect, the step of administering is selected from the group consisting of intratumoral, subcutaneous, intravenous, intraperitoneal, intramuscular, and intravenous injection. In another aspect, the tumor cell growth expresses a mutated KRAS. In another aspect, the tumor cell growth is a lung cancer. In another aspect, the method further comprises a combination therapy with a second anti-neoplasmic agent.

In another embodiment, the present invention includes a method of evaluating a candidate drug believed to be useful in treating a cancer, the method comprising: (a) measuring one or more of the following: the level of expression of at least a wild-type KRAS and one or more mutated KRAS, and two or more target genes in the cancer cells or tissues; the level of expression of a candidate gene or a group of candidate genes in an cellular environment with the lowered expression of one or more mutated KRAS, genes and the two or more target genes in the cancer cells or tissues; the effect of a candidate drug on the phenotype of such cells comprised of lowered expression of one or more mutated KRAS genes and the two or more target genes in the cancer cells or tissues; (b) administering a candidate drug to a first subset of said cancer cells or tissues, and a placebo to a second subset of said cancer cells or tissues; (c) repeating step (a) after the administration of the candidate drug or the placebo; and (d) determining if the candidate drug is effective in producing determined phenotype in an cellular environment with reduced expression of mutated KRAS and the two or more target genes as compared to normal KRAS expressing cellular environment that is statistically significant as compared to any reduction occurring in the second subset of lung cancer cells or tissues, wherein a statistically significant reduction indicates that the candidate drug is useful in treating cancer. In another aspect, the cancer is selected from brain, bladder, blood, bone, breast, cervical, colorectal, gastrointestinal, endocrine, kidney, liver, lung, ovarian, pancreatic, prostate, or thyroid. In another aspect, the mutated KRAS is selectively knocked down, and the two or more target genes are selected from SRC-3, EGFR, PIK3, NCOA3 or ERalpha 1, and the inserts are selected from at least one of RNAi, shRNA or bi-shRNA.

In another embodiment, the present invention includes a method of suppressing the growth of tumor cells in a human subject comprising the steps of: obtaining a tumor cell sample from the human subject; identifying one or more target gene or genes in the human subject in need for suppression to prevent tumor cell growth; constructing a expression vector that comprises an insert that expresses two or more RNAi nucleic acid segments that specifically target the gene or genes identified in the tumor cell sample; wherein the insert comprises: a first and a second RNAi nucleic acid that reduces the expression of the same or different target gene or genes identified in the tumor cell; administering the expression vector in a therapeutic agent carrier complex to the human subject in an amount sufficient to express the two or more RNAi nucleic acid segments; and determining whether the gene or genes have been knocked-down by the expression vector in the target tumor cells, wherein the inhibition results in an apoptosis, an arrested proliferation, or a reduced invasiveness of the tumor cells. In one aspect, the RNAi is selected from at least one of an miRNA, and shRNA, and siRNA, or a bi-shRNA. In another aspect, the at least first, second or third bifunctional RNA molecule is selected from SEQ ID NOS: 5-26, SEQ ID NOS: 27-36, SEQ ID NOS: 38-39, SEQ ID NOS: 40-41, SEQ ID NOS: 42-43, SEQ ID NOS: 48-49, or SEQ ID NOS:50-126. In another aspect, the insert further comprises 3, 4, 5, 6, 7, 8, 9, 10, 11, 12, 13, 14, 15, 16, 17, 18, 20, 21, 25, 50, 75, or 100 copies of RNAi inserts capable of reducing an expression of one or more mutated or normal genes. In another aspect, the expression vector is defined further as comprising the structure: vector-A-B-C-vector, wherein A, B, and C are three or more RNAi nucleic acid segments that can target the same region of an mRNA for the one or more target genes, different regions of the mRNA for the one or more target genes, or different mRNAs from two or more target genes. In one aspect, the inserts A-B-C are selected from SEQ ID NOS: 5-26, SEQ ID NOS: 27-36, SEQ ID NOS: 38-39, SEQ ID NOS: 40-41, SEQ ID NOS: 42-43, SEQ ID NOS: 48-49, or SEQ ID NOS:50-126.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
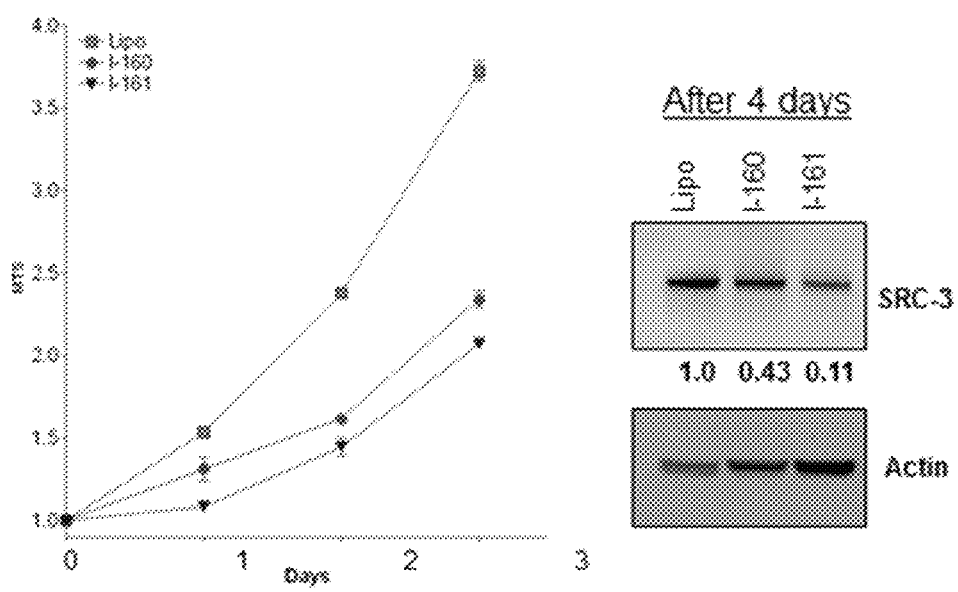
FIG. 1 shows the results from the use of a multi-targeting bishRNA designed to target SRC-3, EGFR and mutant KRAS (G12C) can attenuate lung cancer cell growth.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention include multimeric nucleic acid inserts in expression vectors, which may have the structure: vector-A-B-C-vector, wherein A, B, and C are siRNAs that can target the same region of an mRNA for the one or more target genes, different regions of the mRNA for the one or more target genes, or different mRNAs from two or more target genes. The skilled artisan will recognize that the multimer can include more that A, B, C, for example, D, E, and F . . . or even A', B', C', D', or combinations or multiple targeting inserts, e.g., A, B, C, A', B', C', D', D, E, and F . . . , or even A, A, B, B', C, D, D', D', etc. The combination(s) can be determined using the methods of the present invention, e.g., obtaining a tumor cell sample from the human subject; identifying one or more target gene or genes in the human subject in need for suppression to prevent tumor cell growth; constructing a expression vector that comprises an insert that expresses two or more RNAi nucleic acid segments that specifically target the gene or genes identified in the tumor cell sample; wherein the insert comprises: a first and a second RNAi nucleic acid that reduces the expression of the same or different target gene or genes identified in the tumor cell; administering the expression vector in a therapeutic agent carrier complex to the human subject in an amount sufficient to express the two or more RNAi nucleic acid segments; and determining whether the gene or genes have been knocked-down by the expression vector in the target tumor cells, wherein the inhibition results in an apoptosis, an arrested proliferation, or a reduced invasiveness of the tumor cells. In certain examples, the inserts, A, B, C, A', B', C', D', D, E, and F . . . , or even A, A, B, B', C, D, D', D', etc., are selected from SEQ ID NOS: 5-26, SEQ ID NOS: 27-36, SEQ ID NOS: 38-39, SEQ ID NOS: 40-41, SEQ ID NOS: 42-43, SEQ ID NOS: 48-49, or SEQ ID NOS:50-126.

The activating mutations in the ras proto-oncogenes family render them constitutively active are observed frequently in all human cancers. In particular, the activating K-ras mutations are observed in many lung cancers. K-ras mutations are difficult to target specifically with small molecules, thus knocking down KRAS mutations without affecting the wild-type (wt) RAS expression is a viable approach for the treatment of cancer. All RNAi based KRAS mutation knockdown is either targeting at one specific mutation or concomitantly knockdown the wt RAS expression.

RNAi is the Nobel-prize winning discovery by Fire and Mello in 1998, which has fostered an exponential number of studies and publications furthering the understanding of gene function and stimulating numerous phase I and II clinical trials. This naturally occurring gene-silencing mechanism by small RNAs, which includes endogenous microRNA (miRNA), is highly dependent on gene sequence; thus the mechanism can, in theory, be used to inhibit the expression of any targeted gene[s] with strong specificity. RNAi is not limited by the pharmacologic constraints inherent to the development of small molecules which creates an opportunity to access traditionally "undruggable" targets for disease treatment.

The central player of this mechanism is the RNA Induced Silencing Complex (RISC). The process starts with double-stranded small RNA (composed of a passenger strand and a guide strand) which is incorporated into the pre-RISC followed by the cleavage-dependent or cleavage-independent release of the passenger strand to form the guide strand containing RISC. The guide strand (anti-sense to mRNA) guides the RISC to recognize the target mRNA through sequence complementarity (full or extended partial). A key component of RISC is the family of Argonaute proteins (Ago), Ago 1, 2, 3 and 4 in mammalian systems, of which only Ago 2 has endonuclease activity so as to allow for cleavage of the target mRNA for further degradation (cleavage dependent pathway); all the Ago containing RISC can function through a cleavage-independent effector pathway resulting in translation repression and mRNA sequestration in p-body with subsequent degradation. The cleavage-dependent effector process requires extensive homology between guide strand and both the passenger strand and target mRNA, particularly in the central region; the cleavage-independent effector process, on the other hand, only requires partial homology between guide strand and both the passenger strand and target mRNA.

The present invention takes advantage of both cleavage dependent and cleavage independent loading at the RISC complex, not the events that are downstream from the RISC complex. Thus, as used herein the phrase "cleavage dependent and cleavage independent" refers to the design of RNA(s) that are specifically targeted to RISC and the cleavage dependent and cleavage independent activities at the RISC complex, i.e., loading. It has been found herein and in the parent application for this case, that these "bifunctional shRNAs" have a higher inhibitory activity than the sum of targeting each individual part of the RISC complex. Thus, the higher inhibitory activity of the present invention.

RNA interference can be triggered either by synthetic double stranded small interfering RNA (siRNA) or by vector driven short hairpin RNA (shRNA). Both siRNA and vector driven shRNA have been demonstrated to be effective in in vitro and in vivo applications, each with their respective advantages. Most siRNA are structurally designed to promote efficient incorporation into the Ago2 containing RISC, the RNase III containing Dicer-substrate design improves the efficiency of siRNA at least 10-fold by initial association and processing at the pre-RISC. Vector driven shRNA utilizes the host microRNA biogenesis pathway, which appears to be more efficient. siRNA is more readily chemically modified while shRNA expression can be modulated and regulated by specific promoters.

shRNA and siRNA Design and Synthesis. Current methods in designing shRNA and siRNA (two different methods of RNAi) often employ a set of computer-implemented rules, which are not always reliable and essentially represent a trial-and-error approach. As used herein, "RNAi molecules" refers generally to conventional shRNA molecules (the well-known shRNA molecules routinely used by those of ordinary skill in the art), enhanced shRNA (the novel shRNA molecules and uses thereof encompassed by the present invention and described below) and/or siRNA molecules. As used herein, "shRNA/siRNA," "siRNA/shRNA," and like terms refer to conventional shRNA, enhanced shRNA, siRNA, or any combination of the foregoing.

Recent studies have indicated rather wide-spread off-target effects of siRNAs (and other RNAi molecules). Although a target gene may be effectively silenced, non-specific effects both at the mRNA and protein levels have been reported. Accordingly, for the clinical applications of the present invention described herein, it is important to incorporate RNAi molecules with desirable potency, efficacy, and binding precision and accuracy. In certain embodiments of the invention, the RNAi molecules are preferably conventional or enhanced shRNAs, as such designs have been shown to be more stable, durable, potent and amenable to regulation than siRNAs. In addition, the incorporation of tumor-specific targeting of the delivery vector and tumor-specific promoters may be utilized, thereby adding a multiple-log safety buffer to the invention.

For each selected target gene or genes, the invention provides that a literature search may be conducted to identify any commercially-available shRNA- and siRNA-encoding plasmids that have been shown to modulate the expression of the Target Gene and/or exhibit other preferred characteristics (such as potency, efficacy, and binding precision and accuracy). Additional information regarding such Target Gene, siRNAs, and/or shRNA may, preferably, be obtained from The Cancer Genome Anatomy Project's RNAi site of NCI. If appropriate commercially-available shRNA- and/or siRNA-encoding sequences exist, such compositions or components thereof may be used in the present invention (assuming such compositions satisfy other preferred criteria, such as those relating potency, efficacy, and binding precision and accuracy).

If there are no commercially-available siRNAs or shRNA clones for the selected Target Gene, an appropriate number of shRNAs and/or siRNAs may be designed, such as two, three, four, five, or more shRNAs and/or siRNAs, using readily-available RNAi molecule design computer programs. Synthetic shRNA/siRNA duplexes of HPLC grade may be purchased from any of numerous suppliers, such as Qiagen or IDT.

If there are no commercially-available siRNA or shRNA clones for a Target Gene (and shRNAs and/or siRNAs that are designed using computer software do not demonstrate, for example, desirable efficacy), a "shotgun" approach may be employed. For example, shRNA expression clone synthesis technology, developed by SilereTech, enables the synthesis of a "shotgun" library of shRNA expressing vectors for a given target sequence (e.g., Target Gene). The shotgun library provides thousands of RNAi candidates that are randomly distributed along the target sequence. From the shotgun library, numerous shRNA expressing vectors with varied potency and efficacy may be identified. The shotgun library provides a rich source of representative RNAi molecules (e.g., shRNAs or siRNAs) that do not require repeated synthesis, testing, or vector construction. With a proper screening process, shRNA and/or siRNA expression vectors of desired potency and efficacy may be readily identified.

The invention provides that the shRNA and/or siRNA sequences purchased, designed, or otherwise identified (using the above-mentioned "shotgun" approach) are, preferably, reviewed for unwanted "off-target" effects (i.e., binding to sequences other than the intended Target Gene). For example, the predicted "off-target" effects, or lack thereof, of a shRNA or siRNA molecule may be analyzed by conducting a BLAST search against irrelevant gene sequences of the NCBI GeneBank database.

In addition to shRNA/siRNA-mediated inhibition of gene expression, the invention provides that other appropriate methods may be employed to modulate the expression of one or more Target Genes. While the use of shRNA/siRNA to modulate gene expression is used throughout the present specification, the invention provides that such other appropriate methods may be used in addition to (or in replacement of) shRNA/siRNA methods. For example, the invention provides that other transcriptional and/or translation inhibitors may be employed to modulate Target Gene expression. Non-limiting examples of transcriptional modulators may include helix-turn-helix, zinc finger, leucine zipper, and/or helix-loop-helix proteins. Non-limiting examples of translational inhibitors/modulators may further include other forms of antisense technology, as well as siRNA-binding proteins, miRNAs, miRNA-binding proteins, small molecular inhibitors (e.g., anisomycin, cycloheximide, emetine, harringtonine and puromycin), and like compositions.

The present inventors have also developed the novel vector driven shRNA technology, the bi-functional shRNA (bi-shRNA), to further improve the efficiency of RNAi by harnessing both cleavage-dependent and cleavage-independent pathways of RISC loading in one pre-programmed molecule. The vector driven bi-shRNA includes two stem-loop structures for each mRNA target sequence, one stem-loop shRNA has perfect complementarity at the stem and the second stem-loop shRNA contains mismatches on the passenger strand of the stem (thereby differing from prior art mismatched RNA that include the mismatch on the guide strand). Importantly, following incorporation into the RISC, the guide strands derived from each of the two structures are fully complementary to the mRNA target sequence but are associated with different Ago containing RISCs. The bi-shRNA design leads to more rapid onset of gene silencing, higher efficacy, and greater durability when compared with either siRNA or conventional shRNA. Currently personalized cancer therapy with target specific bi-shRNA is transitioned into the clinic in Phase I studies using a modified bilamellar invaginated liposome delivery vehicle. Key molecular methods involved in design, construction, and the implementation of bi-shRNA are provided below.

Depending on that objective and the embodiments, several different vectors, promoters, or plasmid backbones and delivery systems can be used. It has been found useful to choose an expression vector with efficient transgene expression. The present inventors recognized that an expression vector with powerful promoters, e.g., an extended CMV promoter containing IE 5'UTR and partial Intron A (pUMVC3), is more effective than those with a cloning site immediately adjacent to the CMV promoter. In certain embodiments it is beneficial to have a stretch of lead transcript before the stem-loop structures. In addition, if more than one vector usage is planned, an effective shuttle strategy should be worked out beforehand; modification by PCR amplification of the expressed cassette is not as efficient. The choice of promoter is also important; RNA polymerase III promoters are much stronger in expression but competitively saturate the endogenous miRNA maturation process at both the nuclear export and RISC loading steps resulting in lethal toxicity in vitro and in vivo with certain delivery vehicles. RNA polymerase II promoters, although less strong in expression, works efficiently and is much less toxic vis-à-vis competition for the endogenous miRNA pathway.

In certain embodiments a sequence that can act in more than one species is designed, particularly if multiple animal model systems are utilized. For most target genes, it is possible to find stretches of target nucleotides that are conserved between species. For finding a sequence that is both conserved and optimum for knockdown, one has to compare the homology-matched sequence with the selected target site sequence.

Public accessible computer programs using differing algorithms (e.g. Dharmacon RNAi design center (www.dharmacon.com) and IDT (www.idtdna.com) are readily available and can be used to locate appropriate target sites within the targeted gene. A search with most computer programs will often yield a preliminary first set of targets for further analysis. Some available publications offer do and do-not suggestions. A BLAST search for each target sequence is to be taken in order to analyze potential cross homology with other mRNAs within the species of interest.

Once the target site sequence is selected, the bi-shRNA design process can begin; the design process is presented below. The bi-shRNA stem-loop structure used by the inventors employs the well-analyzed miR-30a backbone, although, any functional miRNA backbone can be used. The bi-shRNA consists of the two stem-loop structures on a miR-30a backbone located immediately adjacent to each other with a gap about 10 nucleotides long. A longer nucleotide gap can be used and multiple units of bi-sh RNA can be designed to string together in a single transcript targeting either a single gene at multiple sites or multiple different genes simultaneously.

To construct the expression unit to be placed in the multiple cloning sites of an expression vector, an assembly strategy using synthetic oligonucleotides sequentially linked together has been developed. Alternatively, one can also outsource the synthesis of the gene construct with the specified sequence to a biotechnology service company. For the oligonucleotide assembly process, overlapping DNA fragments were designed and synthesized. Because of redundant sequences in the two stem-loop structures, it is necessary to initially ligate the 5' fragments and 3' fragments. The 5' fragment and the 3' fragment can then be purified on gel and further ligated to the middle linking fragments. This assembly process is efficient and, with careful design, many fragments can be repetitively used for different bi-functional constructs.

For each target, it is the best to design and construct at least three bi-functional constructs to compare and from which to select a construct with high knockdown efficiency for further evaluation. Knockdown efficiency can be compared in vitro in tissue culture cells. The present inventors recognized that is generally difficult to compare the knockdown efficiency with endogenously expressed genes because in vitro transfection methods have widely different efficiencies; this is particularly so when the transfection efficiency is low as the knockdown is hard to assess due to background noise from untransfected cells.

Efficacy and efficiency of target gene knockdown by bi-shRNA can be tested with a variety of in vitro and in vivo systems depending on the target and planned application. This in vitro assessment can be conducted following transfection of the bi-shRNA expression plasmids in a variety of cultured cells. The present inventors found that transfections by both electroporation and by liposome (e.g., Lipofectamine 2000) are highly effective, when the amount of plasmid DNA is carefully controlled using a control vector or universal random sequence. For Lipofectamine or a related agent, the present inventors found that the reverse transfection method, in general, is less toxic than the forward transfection method. Target gene knockdown can be assessed by either qRT-PCR for target gene mRNA or by Western and/or ELISA for target gene protein. In one assay methods the expression of mature shRNA by stem-loop RT-PCR is detected, in another essay method, the target mRNA cleavage is detected by 5' RNA-Ligand Mediated RACE (5' RLM-RACE). Stem-loop RT-PCR is a sensitive method dependent on the specific probe primer used; in addition, one can specifically detect and quantify both the passenger strand and guide strand. For bi-shRNA, the method can differentially score both the fully complementary as well as the mismatched (partially complementary) passenger strand. The 5' RLM-RACE method requires ligation of an RNA oligomer onto the cleaved mRNA end, consequently, the method is rendered less efficient. Insofar as a number of rounds of amplifications are often required, a nested primer design is essential to ensure specificity.

Evaluable functionality of bi-shRNA relies on effective plasmid delivery into target cells. The inventors recognize that some in vitro transfection systems often do not translate to inherently more complex in vivo animal models. There are numerous delivery systems designed specifically for systemic applications in vivo. The present inventors utilize the fusogenic, cationic DOTAP:cholesterol bilamellar invaginated vesicle lipoplex (BIV) for in vivo studies and has successfully translated it to the clinic. Modification strategies for more focused biodistribution, targeted delivery, and enhanced intracellular uptake are developed. An effective lipoplex should use plasmids devoid of any contaminants from host *E. coli*. Although endo-free plasmid purification kit produced plasmids are generally used, GLP or GMP produced plasmids are more effective. Unfortunately, colanic acid and other non-endotoxin associated polysaccharides co-purify with DNA by anion exchange chromatography and by cesium chloride density gradient centrifugation. Therefore, endotoxin removal does not remove these contaminants, and HPLC cannot detect these contaminants. To correct this, the Superclean™ procedure has been developed to generate ultra-high quality plasmid DNA, cleansed of these contaminants, for in vivo and clinical applications. Liposome preparation involves highly specialized equipment; the present inventors routinely generate the DOTAP:cholesterol BIV in a GMP facility. Premade liposome may be obtained from a collaborator or purchased from a vendor. The process of preparing lipoplex with high quality liposome and plasmid DNA is described below. The lipoplex formulation can be achieved in most laboratory settings. Once the lipoplex is made, the formulation can be delivered systemically to experimental animals either through slow tail vein injection or with catheters. Target site vector expression can be analyzed using the PCR method for plasmid DNA and the stem-loop RT-PCR for mature bi-shRNA, respectively. bi-shRNA functionality can be assayed with the 5' RLM-RACE for target mRNA cleavage and with Western blot or IHC for target protein knockdown. These analyses can be performed at about 48 hours post treatment. For efficacy, repeated delivery into the experimental animal is often required; the dosing schedule needs to be experimentally determined and optimized.

As used herein, the term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

As used herein, the term "expression vector" refers to nucleic acid molecules encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter. The term "promoter" refers to any DNA sequence which, when associated with a structural gene in a host yeast cell, increases, for that structural gene, one or more of 1) transcription, 2) translation or 3) mRNA stability, compared to transcription, translation or mRNA stability (longer half-life of mRNA) in the absence of the promoter sequence, under appropriate growth conditions.

As used herein, the term "oncogene" refers to genes that permit the formation and survival of malignant neoplastic cells (Bradshaw, T.K.: Mutagenesis 1, 91-97 (1986)).

As used herein, the term "receptor" refers to a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

As used herein, the term "hybridizing" refers to any process by which a strand of nucleic acid binds with a complementary strand through base pairing.

As used herein, the term "transfection" refers to the introduction of foreign DNA into eukaryotic cells. Transfection may be accomplished by a variety of means known to the art including, e.g., calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "bi-functional" refers to an shRNA having two mechanistic pathways of action, that of the siRNA and that of the miRNA. The term "traditional" shRNA refers to a DNA transcription derived RNA acting by the siRNA mechanism of action. The term "doublet" shRNA refers to two shRNAs, each acting against the expression of two different genes but in the "traditional" siRNA mode. The bi-functional shRNA (bi-shRNA) improves the efficiency of RNAi by harnessing both cleavage-dependent and cleavage-independent pathways of RISC loading in one pre-programmed molecule. The vector driven bi-shRNA includes two stem-loop structures for each mRNA target sequence, one stem-loop shRNA has perfect complementarity at the stem and the second stem-loop shRNA contains mismatches on the passenger strand of the stem (thereby differing from prior art mismatched RNA that include the mismatch on the guide strand). Importantly, following incorporation into the RISC, the guide strands derived from each of the two structures are fully complementary to the mRNA target sequence but are associated with different Ago containing RISCs. The bi-shRNA design leads to more rapid onset of gene silencing, higher efficacy, and greater durability when compared with either siRNA or conventional shRNA.

The bi-functional shRNA has a first guide strand sequence is complementary, preferably 100% complementary, to at least a portion of an mRNA transcript encoded by a target gene. The invention provides that this guide strand (which is initially bonded to the passenger strand to form the double stranded stem) comprises a nucleic acid sequence that is capable of binding to the mRNA transcript of the target gene, and is presented to the cleavage-dependent RISC pathway. The invention provides that such binding of the guide strand sequence to the mRNA transcript, and presentation to the cleavage-dependent RISC pathway, causes degradation of the mRNA transcript. The second guide strand sequence is at least partially complementary to at least a portion of the mRNA transcript encoded by the target gene. More particularly, the second guide strand sequence may contain a first portion that is complementary, preferably 100% complementary, to the mRNA transcript encoded by the target gene, whereas a second portion of the guide strand sequence contains certain bases that are mismatched with the corresponding sequence of the target gene mRNA transcript.

As used herein, a "mismatched" base pair refers to two nitrogenous bases within a nucleic acid sequence that, when bound (or hybridized) to each other, do not follow Chargaff's rules of base pairing. Chargaff's rules provide that the purine adenine (A) within a first nucleic acid sequence will pair with the pyrimidine thymine (T) (or uridine (U)) within a second nucleic acid sequence. Furthermore, Chargaffs rules provide that the purine guanine (G) within a first nucleic acid sequence will pair with the pyrimidine cytosine (C) within a second nucleic acid sequence. Thus, a base pairing between two strands (nucleic acid sequences) that does not follow and comply with such rules would be deemed a "mismatched" base pair, e.g., a pairing between G and U, A and G, A and C, G and T, G and U, and so on. A guide strand within the double stranded sequence of the stem-loop structures shown therein, which contain one or more "mismatched" base pairs relative to the passenger strand, creates a bulge in the double stranded stem sequence.

As used herein, the term "liposome" refers to a closed structure composed of lipid bilayers surrounding an internal aqueous space. The term "polycation" as used herein denotes a material having multiple cationic moieties, such as quaternary ammonium radicals, in the same molecule and includes the free bases as well as the pharmaceutically-acceptable salts thereof.

Accordingly, the bifunctional shRNAs may comprise shRNAs designed to enter into and interact with both cleavage-dependent RISC and cleavage-independent RISC. A higher level of gene "knock-down" is achieved using such bifunctional shRNAs compared to other currently-available RNAi methods and compositions, including siRNAs and conventional shRNAs (i.e., shRNA constructs designed to enter cleavage-dependent RISC or cleavage-independent RISC, but not both).

As used herein, gene "knock-down" refers to effective quantitative and durable inhibition of expression. Such gene "knock-down" may be manifested, and/or apparent, in the suppression of target gene mRNA translation, increased target cell apoptosis and/or cell kill.

As used herein, "target gene" refers to a nucleic acid sequence in a cell, wherein the expression of the sequence may be specifically and effectively modulated using the bifunctional shRNA. In certain embodiments, the target gene may be implicated in the growth (proliferation), maintenance (survival), and/or migratory (metastatic) behavior of an individual's cancer. The invention provides, however, that the target gene may be implicated in any other disease or medical condition, and is not limited to genes implicated in cancer. For example, the target gene may represent any sequence that an investigator or clinician wishes to silence (i.e., reduce the expression level of such target gene).

Vector sequence may comprise a promoter, which is operably linked (or connected), directly or indirectly, to a sequence encoding the bifunctional shRNAs. Such promoters may be selected based on the host cell and the effect sought. Non-limiting examples of suitable promoters include constitutive and inducible promoters, such as inducible RNA polymerase II (pol II)-based promoters. Non-limiting examples of suitable promoters further include the tetracycline inducible or repressible promoter, RNA polymerase I or III-based promoters, the pol II dependent viral promoters, such as the CMV-IE promoter, and the pol III U6 and H1 promoters. The bacteriophage T7 promoter may also be used (in which case it will be appreciated that the T7 polymerase must also be present). The invention shall not be restricted to the use of any single promoter, especially since the invention may comprise two or more bifunctional-shRNAs (i.e., a combination of effectors), including but not limited to incorporated shRNA singlets. Each incorporated promoter may control one, or any combination of, the shRNA singlet components.

In certain embodiments, the promoter may be preferentially active in the targeted cells, e.g., it may be desirable to preferentially express the bifunctional shRNA molecules in tumor cells using a tumor cell-specific promoter. Introduction of such constructs into host cells may be effected under conditions whereby the two or more RNA molecules that are contained within the bifunctional shRNA precursor transcript initially reside within a single primary transcript, such that the separate RNA molecules (each comprising its own stem-loop structure) are subsequently excised from such precursor transcript by an endogenous ribonuclease. The invention further provides that splice donor and acceptor sequences may be strategically placed within the primary transcript sequence to promote splicesome-mediated nuclear processing. The resulting mature shRNAs may then induce degradation, and/or translation repression, of target gene mRNA transcripts produced in the cell. Alternatively, each precursor stem-loop structure may be produced as part of a separate transcript, in which case each shRNA-encoding sequence will preferably include its own promoter and transcription terminator sequences. Additionally, the bifunctional shRNA precursor transcript may reside within a single primary transcript, which, optionally, further comprises of one or more mRNA sequences that encode one or more functional mammalian proteins. For example, the one or more mRNA sequences may encode certain proteins that are known to bolster a patient's immune system, or otherwise provide some preventative and/or therapeutic effect that will operate in parallel with the bifunctional shRNA.

The stem-loop structures of the shRNA molecules described herein may be about 40 to 100 nucleotides long or, preferably, about 50 to 75 nucleotides long. The stem region may be about 19-45 nucleotides in length (or more), or more preferably about 20-30 nucleotides in length. The stem may comprise a perfectly complementary duplex (but for any 3' tail), however, bulges or interior loops may be present, and even preferred, on either arm of the stem. The number of such bulges and asymmetric interior loops are preferably few in number (e.g., 1, 2 or 3) and are about 3 nucleotides or less in size. The terminal loop portion may comprise about 4 or more nucleotides, but preferably not more than about 25. More particularly, the loop portion will preferably be 6-15 nucleotides in size.

As described herein, the stem regions of the bifunctional shRNAs comprise passenger strands and guide strands, whereby the guide strands contain sequences complementary to the target mRNA transcript encoded by the target gene(s). Preferably, the G-C content and matching of guide strand and passenger strand is carefully designed for thermodynamically-favorable strand unwind activity with or without endonuclease cleavage. Furthermore, the specificity of the guide strand is preferably confirmed via a BLAST search (www.ncbi.nim.nih.qov/BLAST).

Expression level of multiple target genes may be modulated using the methods and bifunctional shRNAs described herein. For example, the invention provides that a first set of bifunctional shRNAs may be designed to include a sequence (a guide strand) that is designed to reduce the expression level of a first target gene, whereas a second set of bifunctional shRNAs may be designed to include a sequence (a guide strand) that is designed to reduce the expression level of a second target gene. The different sets of bifunctional shRNAs may be expressed and reside within the same, or separate, preliminary transcripts. In certain embodiments, such multiplex approach, i.e., the use of the bifunctional shRNAs described herein to modulate the expression level of two or more target genes, may have an enhanced therapeutic effect on a patient. For example, if a patient is provided with the bifunctional shRNAs described herein to treat, prevent, or ameliorate the effects of cancer, it may be desirable to provide the patient with two or more types of bifunctional shRNAs, which are designed to reduce the expression level of multiple genes that are implicated in the patient's cancer.

In certain embodiments, the invention further provides that the bifunctional shRNA sequences may comprise stem sequences of naturally occurring miRNAs (e.g., miR-30, *C. elegans* let-7 and/or lin-4). While the presence of a miR-30 loop, for example, may be desirable, the invention provides that variations of that structure may be tolerated, wherein loops may be used that are greater than 72%, preferably greater than 79%, more preferably greater than 86%, and most preferably, greater than 93% identical to, for example, the miR-30 sequence (determined using well-known computer programs such as the BESTFIT program (Wisconsin Sequence Analysis Package, Version 8 for Unix, Genetics Computer Group, University Research Park, 575 Science Drive, Madison, Wis. 53711)).

The precursor sequences (or constructs) encoding the bifunctional shRNAs may be introduced into host cells using any of a variety of techniques and delivery vehicles well-known in the art. For example, infection with a viral vector comprising one or more constructs may be carried out, wherein such viral vectors preferably include replication defective retroviral vectors, adenoviral vectors, adeno-associated vectors, lentiviral vectors, or measle vectors. In addition, transfection with a plasmid comprising one or more constructs may be employed. Such plasmids may be present as naked DNA, or may be present in association with, for example, a liposome (e.g., an immunoliposome). Still further, the delivery vehicle may consist of immunolipoplexes, targeted nanoparticles, targeted liposomes, cyclodextrins, nanoparticles, aptamers, dendrimers, chitosan, or pegylated derivatives thereof. The nature of the delivery vehicle may vary depending on the target host cell.

In-vivo delivery of the bifunctional shRNA-encoding constructs may be carried out using any one of a variety of techniques, depending on the target tissue. Delivery may be, for example, achieved by direct injection, inhalation, intravenous injection or other physical methods (including via micro-projectiles to target visible and accessible regions of tissue (e.g., with naked DNA). Administration may further be achieved via syringe needles, trocars, canulas, catheters, etc., as appropriate.

In addition to the methods of using the bifunctional shRNAs described herein, provided for are shRNAs themselves. Accordingly, additional aspects include nucleic acid sequences, which may comprise a single contiguous sequence or multiple distinct sequences that, individually or collectively, encode two or more RNA molecules. According to such embodiments, a first RNA molecule will comprise a double stranded sequence that includes a guide strand sequence that is complementary to a portion of an mRNA transcript encoded by a target gene, whereas a second RNA molecule comprises a second double stranded sequence that includes a second guide strand sequence that is partially complementary to a portion of such mRNA transcript. Preferably, the second guide strand sequence of the second RNA molecule comprises one or more bases that are mismatched with a nucleic acid sequence of the mRNA transcript encoded by the target gene. According to further aspects, expression vectors are provided which comprise the nucleic acid sequences, and may be used to carry out the methods, and express the bifunctional shRNAs, described herein.

Still further, methods of using the nucleic acid sequences and bifunctional shRNAs are described herein to prevent, treat and/or ameliorate the effects of one or more medical conditions, including without limitation various types of cancer. For example, the invention provides that the bifunctional shRNAs described herein may be used to reduce the expression level of one or more target genes that are implicated in cancer cell growth, survival, and/or metastasis. For example, as demonstrated in the Examples below, the bifunctional shRNAs may be used to reduce the expression level of certain target genes that encode scaffold proteins, which have been found to be over-expressed in cancer cells. Non-limiting examples of such target genes include K-ras.

RNA Interference: The introduction of artificial double-stranded small interfering RNAs (siRNAs) into animal and plant cells can induce the degradation of targeted mRNA molecules with complementary sequence; the process is known as RNA interference (RNAi) (Sharp 2001; Hutvagner and Zamore 2002; Zamore 2002) (see U.S. Pat. No. 6,506, 559). RNAi has emerged as a useful experimental tool with strong potential for therapeutic applications (Fire, Xu et al. 1998; Hammond, Bernstein et al. 2000; Elbashir, Harborth et al. 2001; Senzer, Rao et al. 2009; Wang Z 2011). However, in mammalian cells, induction of RNAi using shRNAs requires the transfection of RNA oligonucleotides, which can be inefficient with the duration of effective silencing limited by vehicle disassembly time and siRNA biologic half life. Despite these limitations, in a recent early results publication of a clinical phase I study, Davis and colleagues have convincingly demonstrated target specific silencing and site-specific cleavage with systemic delivery of a pegylated, transferrin decorated, cyclodextrin-based siRNA targeting the M2 subunit of ribonucleotide reductase (RRM2) (CALAA-01) (Davis, Zuckerman et al. 2010). Three reported patients with biopsy accessible melanoma, who were treated as per the dose-escalation Phase I study, received 18, 24, or 30 mg/m2 CALAA-01 by intravenous infusion on days 1, 3, 8, and 10 of a 21 day cycle. Voluntary biopsies were performed after the final dose of cycle 1 in each and compared to archived tumor, and at 1 month post cycle 1 (prior to initiation of cycle 2) and on the day of the final dose of cycle 2 in the patient treated at 30 mg/m2. RRM2 mRNA reduction was confirmed by qRT-PCR comparing post- and pre-cycle 2 tissue samples at 30 mg/m2. In the same patient, immunohistochemistry and Western blot pre- and post-cycle 1 showed a five-fold reduction in MMR2 protein. Supporting the proposed mechanism of action, 5'-RLM-RACE (5'-RNA-ligase-mediated rapid amplification of complementary DNA ends) confirmed the predicted cleavage site. This first-in-human demonstration of targeted tumor cell entry (using transmission electron microscopy) and mRNA and protein expression reduction along with predicted site-specific siRNA cleavage following systemic delivery brings added impetus to translational application of RNAi.

siRNA requires chemical modification to increase serum stability, cellular uptake and duration of action. Alternatively, siRNA can be constructed as a short hairpin RNA (shRNA). shRNA consists of a stem-loop structure that can be transcribed in cells from RNA polymerase III (or, less frequently used, RNA polymerase II) promoter on a plasmid construct (Miyagishi and Taira 2002; Yu, DeRuiter et al. 2002). Constitutive expression of shRNA from a plasmid independently from the chromosome provides an advantage over synthetic siRNA. The shRNA expression units can be incorporated into a variety of plasmids and viral vectors for intracellular delivery and nuclear import. In addition, vector based shRNA expression can also be regulated or induced (Gossen and Bujard 1992; Gupta, Schoer et al. 2004; Dickins, Hemann et al. 2005). shRNAs, as opposed to synthetic siRNAs, are synthesized in the nucleus of cells, then processed and transported to the cytoplasm to be incorporated into the RNA-induced silencing complex (RISC) for activity (Cullen 2005). To be effective, shRNA has to be designed to utilize the endogenous cellular microRNA biogenesis machinery.

Bifunctional shRNA: As described above, RNA interference (RNAi) is a natural cellular regulatory process capable of inhibiting transcriptional, post-transcriptional and translational mechanisms thereby modulating gene expression. Using a miR30-scaffold, the present inventors developed a "bifunctional" RNAi strategy which demonstrated more effective silencing of target gene expression by concurrently inducing translational repression, and [GW 182-mediated] sequestration in the p-body (as a holding reservoir or promoting decapping, deadenylation and mRNA degradation) (cleavage-independent) as well as post-transcriptional mRNA mRNA cleavage (cleavage dependent) (Rao D 2010).

The present inventors have developed a novel bifunctional shRNA (bi-shRNAi) RNA interference (RNAi) technology. Bi-shRNAi allows for programmed endonuclease and non-endonuclease Argonaute (Ago) containing RISC (RNA-induced silencing complexes) loading to simultaneously effect mRNA cleavage, degradation, and translational repression resulting in higher potency and over longer duration than other RNAi mediators. In order to explore the potential of bi-shRNAi in KRAS mutant selective knockdown, an in vitro dual luciferase reporter assay system was established to systematically compare knockdown activity of the mutant allele and the wild-type allele in the same assay environment. The present invention includes the development of therapeutic agents specific for G12D, G12V, G12R and G12C for the treatment of, e.g., pancreatic ductal adenocarcinoma (PDAC).

Of a series of bi-shRNA expression vector constructs targeting G12D with a single nucleotide mutation at each position of the guide strand, it was found that the most discriminating knockdown activity for the mutant allele produced by placing a mutant nucleotide at position 2-4. By examining the knockdown effect of additional mismatches at other positions of the guide strand it was determined that the process was sequence-specific. Similar constructs were made for G12V, G12R and G12C mutations and they are effective in the knockdown of their respective target mutant alleles. G12R specific constructs cross-react with G12C mutants.

The constructs of the present invention were compared to control vector on KRAS knockdown using HEK-293 cells (wt/wt), PANC-1 cells (wt/G12D allele) and MiaPaCa2 cells (wt/G12C allele). G12D and G12C selective bi-shRNA expression vectors did not reduce KRAS expression in HEK-293 in contrast to reduction of KRAS expression in PANC-1 cell and MiaPaCa2 cell, respectively. It was found that, e.g., a single expression construct with multimeric bi-shRNA units capable of knocking down G12D, G12V, G12R and G12C is going to be tested for effectiveness and specificity in vitro and in vivo.

KRAS (Kirsten-ras) oncogene is mutated in a significant proportion of pancreatic ductal adenocarcinoma (PDAC), colorectal and non-small-cell lung cancers (NSCLC) (Downward J, Nat Rev Cancer. 2003; 3:11-22.). In the majority of PDAC (70-90%) patients carrying KRAS mutations, the five year survival rate is less than 5% (Saif M W et al. World J Gastroenterol. 2007; 13; 4423-4430). KRAS is a member of guanine nucleotide-binding protein family and is an integral component of multiple intracellular signaling pathways including epidermal growth factor receptor (EGFR). The overwhelming majority of mutations in KRAS are single nucleotide somatic mutations resulting in single amino acid substitutions at codons 12 or 13. G12D, G12V, G12R and G12C KRAS mutations comprise >90% of KRAS mutations found in PADC patients (COSMIC Database, www.sanger.ac.uk/genetics/CGP/cosmic/). KRAS mutations essentially result in constitutively active KRAS and unregulated downstream signaling (Schubbert S, et al. Nat Rev Cancer. 2007; 7: 295-308). In addition, targeted agents such as the antibody Cetuximab (in colorectal cancer) and the small molecular inhibitor vemurafenib (in BRAF mutant melanoma), perform poorly in patients with KRAS mutations (Karapetis C S, et al. N Engl J Med 2008; 259 (17): 1757-1765). Consequently an effective cancer therapeutic strategy requires KRAS mutation selectivity sparing wild-type functionality. The present inventors have recently developed a novel bi-functional shRNA RNA interference (bi-shRNAi) technology. Bi-shRNAi allows for programmed endonuclease and non-endonuclease Argonaute protein (Ago) containing RISC (RNA-induced silencing complexes) loading to simultaneously effect mRNA cleavage, degradation, and translational repression resulting in higher potency and over longer duration than other RNAi mediators.

The present inventors targeted SRC-3 as a key oncogenic nuclear receptor coactivator; that nuclear hormone receptor coactivators are required for nuclear receptors to function as transcription factors and play key roles as rheostats that determine the amplitude of biological responses to steroid hormones; that overexpression of the steroid receptor coactivator-3/amplified in breast cancer 1 (SRC-3) is implicated in a wide range of cancers and is frequently overexpressed at high percentages in hormone-dependent cancers such as breast, ovarian, endometrial and prostate cancers, and other cancers including pancreatic, esophageal, nasopharyngeal, urothelial and colorectal cancers. In breast and ovarian cancers where it was first characterized, the SRC-3 gene is amplified in approximately 10% of breast cancers and its mRNA is overexpressed ~64% of the time; and that elevated expression of SRC-3 also has been associated with resistance to tamoxifen therapy and poor disease outcome.

SRC-3 is overexpressed in an estimated 322,000 new cancer cases and 91,000 cancer deaths in the US each year and that experimental targeting of SRC-3 limits breast cancer cell growth and restores the ability of SERMs to block cancer cells growth; that siRNA-mediated disruption of SRC-3 expression in BT-474 breast cancer cells restores the growth inhibitory effects of 4-hydroxytamoxifen; that siRNA-mediated disruption of SRC-3 expression also impairs epidermal growth factor (EGF) activity in a variety of cell lines; and that siRNA targeting of SRC-3 leads to reduced transcriptional activity of E2F, impairing the expression of genes important for entry into S phase.

Overexpression of SRC-3 promotes prostate cancer cell growth, while in SRC-3 knockout mice, AKT signaling is downregulated; and that transgenic mice that overexpress SRC-3 develop spontaneous malignant mammary tumors; in contrast, SRC-3 knockout mice are resistant to chemical carcinogen-induced and viral-induced mammary tumorigenesis; furthermore, that SRC-3/− mice are resistant to induced prostate cancer progression. The present inventors also appreciate that many advanced hormone refractory breast cancers cease to express ERα and that agents that reduce SRC-3 cellular protein concentration are more inclusive and able to function as anticancer agents in both ERα positive or negative breast cancers.

A multi-targeting bishRNA designed to target SRC-3, EGFR and mutant KRAS (G12C) can attenuate lung cancer cell growth. FIG. 1 shows the results from the use of a multi-targeting bishRNA designed to target SRC-3, EGFR and mutant KRAS (G12C) can attenuate lung cancer cell growth. The H358 lung cancer cell line, which expresses SRC-3, EGFR and a mutant form of KRAS (G12C), was transiently transfected with two different triple targeting bishRNAs (pGBI-160 or pGBI-161) that target these three oncogenes or a lipoplex only control (lipo) using Lipofectamine 2000 (Invitrogen). Cell proliferation was assayed using a colorimetric MTS assay on days 1, 2, and 3 normalized to MTS values determined on the day of transfection (day 0). On day 4, cells were harvested and the extent of SRC-3 knockdown was assessed by Western analysis.

Materials and Methods: H358 lung cancer cells: H358 lung cancer cells were obtained from the American Type Culture Collection (ATCC) (Manassas, Va.). Cells were maintained in Dulbecco's modified Eagle's medium (DMEM) supplemented with 10% fetal calf serum, penicillin and streptomycin (100 U/ml) and cultured at 37° C. under 5% CO$_2$.

Cell growth assays: All the cell lines discussed above were seeded in a 96-well plate and treated with bishRNA vectors complexed with lipofectamine 2000 or with lipofectamine 2000 only as a control. One, two or threes day later, cell growth was determined using a MTS assay (Promega) according to the manufacturer's instructions.

Figure 2:
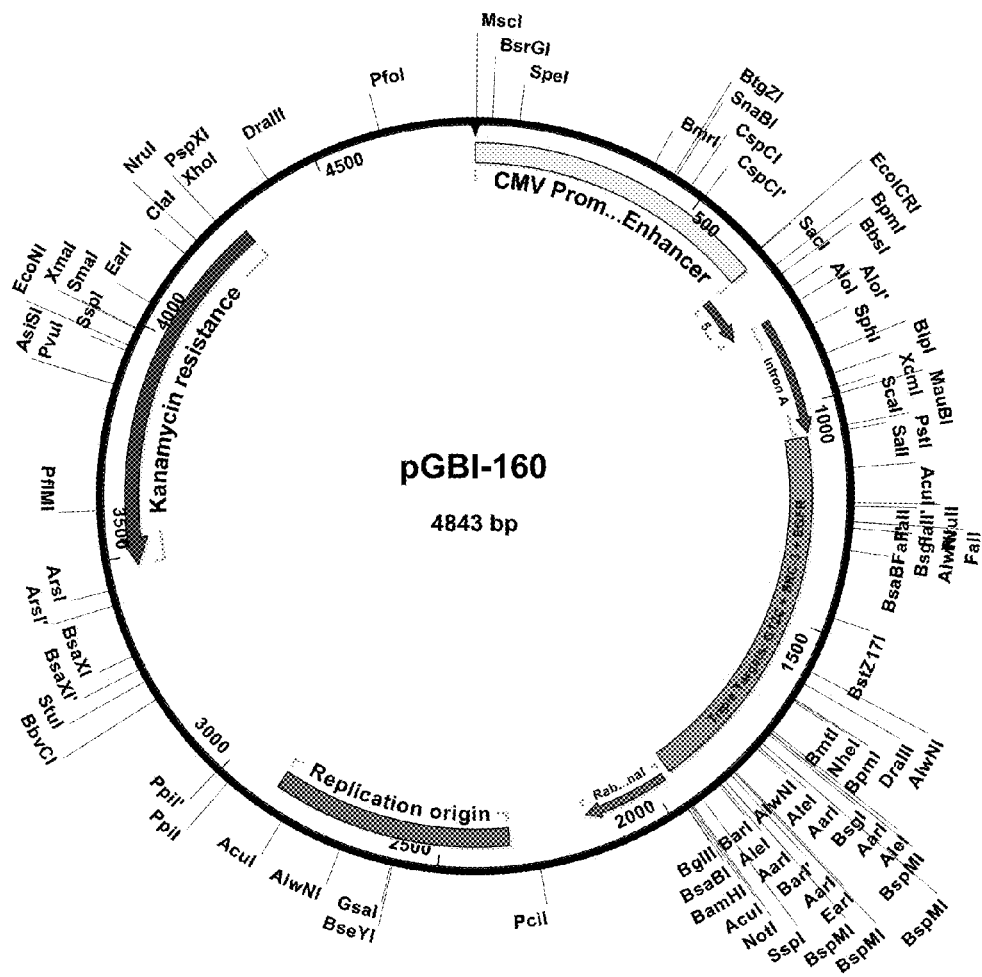
FIG. 2 shows one construct of the present invention.

FIG. 2 shows one construct of the present invention: pGBI-160.

Triple targeting bi-shRNA, targeting KRAS G12C mutation, SRC-3 and EGFR. Bi-shRNA sequences are in upper case letters, pUMVC3 sequence are in lower case letters.

(SEQ ID NO:: 1)
tggccattgcatacgttgtatccatatcataatatgtacatttatatt ggctcatgtccaacattaccgccatgttgacattgattattgactagt tattaatagtaatcaattacgggtcattagttcatagcccatatatg gagttccgcgttacataacttacggtaaatggcccgcctggctgaccg cccaacgaccccgccccattgacgtcaataatgacgtatgttcccata gtaacgccaatagggactttccattgacgtcaatgggtggagtattta cggtaaactgcccacttggcagtacatcaagtgtatcatatgccaagt acgcccctattgacgtcaatgacggtaaatggcccgcctggcattat gcccagtacatgaccttatgggactttcctacttggcagtacatctac gtattagtcatcgctattaccatggtgatgcggttttggcagtacatc aatgggcgtggatagcggtttgactcacggggatttccaagtctccac cccattgacgtcaatgggagtttgttttggcaccaaaatcaacgggac tttccaaaatgtcgtaacaactccgccccattgacgcaaatgggcggt aggcgtgtacggtgggaggtctatataagcagagctcgtttagtgaac cgtcagatcgcctggagacgccatccacgctgttttgacctccataga agacaccgggaccgatccagcctccgcggccgggaacggtgcattgga acgcggattccccgtgccaagagtgacgtaagtaccgcctatagactc tataggcacacccctttggctcttatgcatgctatactgtttttggct tggggcctatacacccccgcttccttatgctataggtgatggtatagc ttagcctataggtgtgggttattgaccattattgaccactccaacggt ggagggcagtgtagtctgagcagtactcgttgctgccgcgcgcgccac cagacataatagctgacagactaacagactgttcctttccatgggtct tttctgcagtcaccgtcgTCGACAATTATCTATTTCAAATTTAGCAGG

AAAAAAGAGAACATCACCTTGTAAAACTGAAGATTGTGACCAGTCAGA

ATAATGTTGTGGTAGTTGGAGCTTGTGATATGTGCATCTACAAGCTCC

AACTACCACACATTATGGTGACAGCTGCCTCGGGAAGCCAAGTTGGGC

TTTAAAGTGCAGGGCCTGCTGATGTTGAGTGCTTTTTGTTCTGTGGTA

GCAAGAGCTAGTAGTGAAGTAGATTAGCATCTACAAGCTCCAACTACC

ACACATAAGAAGTTATGTATTCATCCAATAATTCAAGCCAAGCAAGTA

TATAGGTGTTTTAATAGTTTTTGTTTGCAGTCCTCTGTTGGAAATGAG

ATGACAGTATAGAAGAATGTAGTATACTGTCATCTCATTTCCTGGTGG

CCTGCTATTTCCTTCAAATGAATGATTTTTACTAATTTTGTGTACTTT

TATTGTGTCGATGTAGAATCTGCCTGGTCTATCTGATGTGACAGCTTC

TGTAGCACGGAAATGATGCGACACTATGTGTTTAGTTATCTATACTGT

CATCTCATTTCCTACTGCTAGCTGTAGAACTCCAGCTTCGGCCTGTCG

CCCAATCAAACTGTCCTGTTACTGAACACTGTTCTATGGTTCACCTGC

GTGAAGAAGTGTTGTGTGATATTCTGCACACTTCTTCACGCAGGTGCT

GTGGTAGTGAAAAGTCTGTAGAAAAGTAAGGGAAACTCAAACCCCTTT

CTACACCACCTGCGACTAGAAGAGTGTGTTTCTGTATGGACACTTCTT

CACGCAGGTGTGAGTTTGGTGGGGATTGTGACCAGAAGATTTTGAAAA

TTAAATATTACTGAAGATTTCGACTTCGCggccgcggatccAgatctt tttccctctgccaaaaattatggggacatcatgaagcccttgagcat ctgacttctggctaataaaggaaatttattttcattgcaatagtgtgt tggaattttttgtgtctctcactcggaaggacatatgggagggcaaat catttaaaacatcagaatgagtatttggtttagagtttggcaacatat gcccattcttccgcttcctcgctcactgactcgctgcgctcggtcgtt cggctgcggcgagcggtatcagctcactcaaaggcggtaatacggtta tccacagaatcaggggataacgcaggaaagaacatgtgagcaaaaggc cagcaaaaggccaggaaccgtaaaaaggccgcgttgctggcgtttttc cataggctccgcccccctgacgagcatcacaaaaatcgacgctcaagt

```
cagaggtggcgaaacccgacaggactataaagataccaggcgtttccc
cctggaagctccctcgtgcgctctcctgttccgaccctgccgcttacc
ggatacctgtccgcctttctcccttcgggaagcgtggcgctttctcat
agctcacgctgtaggtatctcagttcggtgtaggtcgttcgctccaag
ctgggctgtgtgcacgaaccccccgttcagcccgaccgctgcgcctta
tccggtaactatcgtcttgagtccaacccggtaagcacgacttatcg
ccactggcagcagccactggtaacaggattagcagagcgaggtatgta
ggcggtgctacagagttcttgaagtggtggcctaactacggctacact
agaagaacagtatttggtatctgcgctctgctgaagccagttaccttc
ggaaaaagagttggtagctcttgatccggcaaacaaaccaccgctggt
agcggtggttttttgtttgcaagcagcagattacgcgcagaaaaaa
ggatctcaagaagatcctttgatcttttctacggggtctgacgctcag
tggaacgaaaactcacgttaagggattttggtcatgagattatcaaaa
aggatcttcacctagatccttttaaattaaaaatgaagttttaaatca
atctaaagtatatatgagtaaacttggtctgacagttaccaatgctta
atcagtgaggcacctatctcagcgatctgtctatttcgttcatccata
gttgcctgactcgggggggggggcgctgaggtctgcctcgtgaagaa
ggtgttgctgactcataccaggcctgaatcgcccatcatccagccag
aaagtgagggagccacggttgatgagagctttgttgtaggtggaccag
ttggtgattttgaacttttgctttgccacggaacggtctgcgttgtcg
ggaagatgcgtgatctgatccttcaactcagcaaaagttcgatttatt
caacaaagccgccgtcccgtcaagtcagcgtaatgctctgccagtgtt
acaaccaattaaccaattctgattagaaaaactcatcgagcatcaaat
gaaactgcaatttattcatatcaggattatcaataccatattttgaa
aaagccgtttctgtaatgaaggagaaaactcaccgaggcagttccata
ggatggcaagatcctggtatcggtctgcgattccgactcgtccaacat
caatacaacctattaatttcccctcgtcaaaaataaggttatcaagtg
agaaatcaccatgagtgacgactgaatccggtgagaatggcaaaagct
tatgcatttcttttccagacttgttcaacaggccagccattacgctcgt
catcaaaatcactcgcatcaaccaaaccgttattcattcgtgattgcg
cctgagcgagacgaaatacgcgatcgctgttaaaaggacaattacaaa
caggaatcgaatgcaaccggcgcaggaacactgccagcgcatcaacaa
tattttcacctgaatcaggatattcttctaatacctggaatgctgttt
tcccggggatcgcagtggtgagtaaccatgcatcatcaggagtacgga
taaaatgcttgatggtcggaagaggcataaattccgtcagccagttta
gtctgaccatctcatctgtaacatcattggcaacgctacctttgccat
gtttcagaaacaactctggcgcatcgggcttcccatacaatcgataga
ttgtcgcacctgattgcccgacattatcgcgagcccatttataccat
ataaatcagcatccatgttggaatttaatcgcggcctcgagcaagacg
tttcccgttgaatatggctcataacacccatgtattactgtttatgta
agcagacagttttattgttcatgatgatatattttttatcttgtgcaat
```

```
gtaacatcagagattttgagacacaacgtggattccccccccccccat
tattgaagcatttatcagggttattgtctcatgagcggatacatattt
gaatgtatttagaaaaataaacaaataggggttccgcgcacatttccc
cgaaaagtgccacctgacgtctaagaaaccattattatcatgacatta
acctataaaaataggcgtatcacgaggccctttcgtctcgcgcgtttc
ggtgatgacggtgaaaacctctgacacatgcagctcccggagacggtc
acagcttgtctgtaagcggatgccgggagcagacaagcccgtcagggc
gcgtcagcgggtgttggcgggtgtcggggctggcttaactatgcggca
tcagagcagattgtactgagagtgcaccatatgcggtgtgaaataccg
cacagatgcgtaaggagaaaataccgcatcagattggctat.
```

Bifunctional Sequence 106

(SEQ ID NO:: 2)
TCGACAATTATCTATTTCAAATTTAGCAGGAAAAAAGAGAACATCACC
TTGTAAAACTGAAGATTGTGACCAGTCAGAATAATGTTGTGGTAGTTG
GAGCTTGTGATATGTGCATCTACAAGCTCCAACTACCACACATTATGG
TGACAGCTGCCTCGGGAAGCCAAGTTGGGCTTTAAAGTGCAGGGCCTG
CTGATGTTGAGTGCTTTTTGTTCTGTGGTAGCAAGAGCTAGTAGTGAA
GTAGATTAGCATCTACAAGCTCCAACTACCACACATAAGAAGTTATGT
ATTCATCCAATAATTCAAGCCAAGCAAGTATATAGGTGTTTTAATAGT
TTTTGTTTGCAGTCCTCTGTTGGAAATGAGATGACAGTATAGAAGAAT
GTAGTATACTGTCATCTCATTTCCTGGTGGCCTGCTATTTCCTTCAAA
TGAATGATTTTTACTAATTTTGTGTACTTTTATTGTGTCGATGTAGAA
TCTGCCTGGTCTATCTGATGTGACAGCTTCTGTAGCACGGAAATGATG
CGACACTATGTGTTTAGTTATCTATACTGTCATCTCATTTCCTACTGC
TAGCTGTAGAACTCCAGCTTCGGCCTGTCGCCCAATCAAACTGTCCTG
TTACTGAACACTGTTCTATGGTTCACCTGCGTGAAGAAGTGTTGTGTG
ATATTCTGCACACTTCTTCACGCAGGTGCTGTGGTAGTGAAAAGTCTG
TAGAAAAGTAAGGGAAACTCAAACCCCTTTCTACACCACCTGCGACTA
GAAGAGTGTGTTTCTGTATGGACACTTCTTCACGCAGGTGTGAGTTTG
GTGGGGATTGTGACCAGAAGATTTTGAAAATTAAATATTACTGAAGAT
TTCGACTTCGC.

Figure 3:
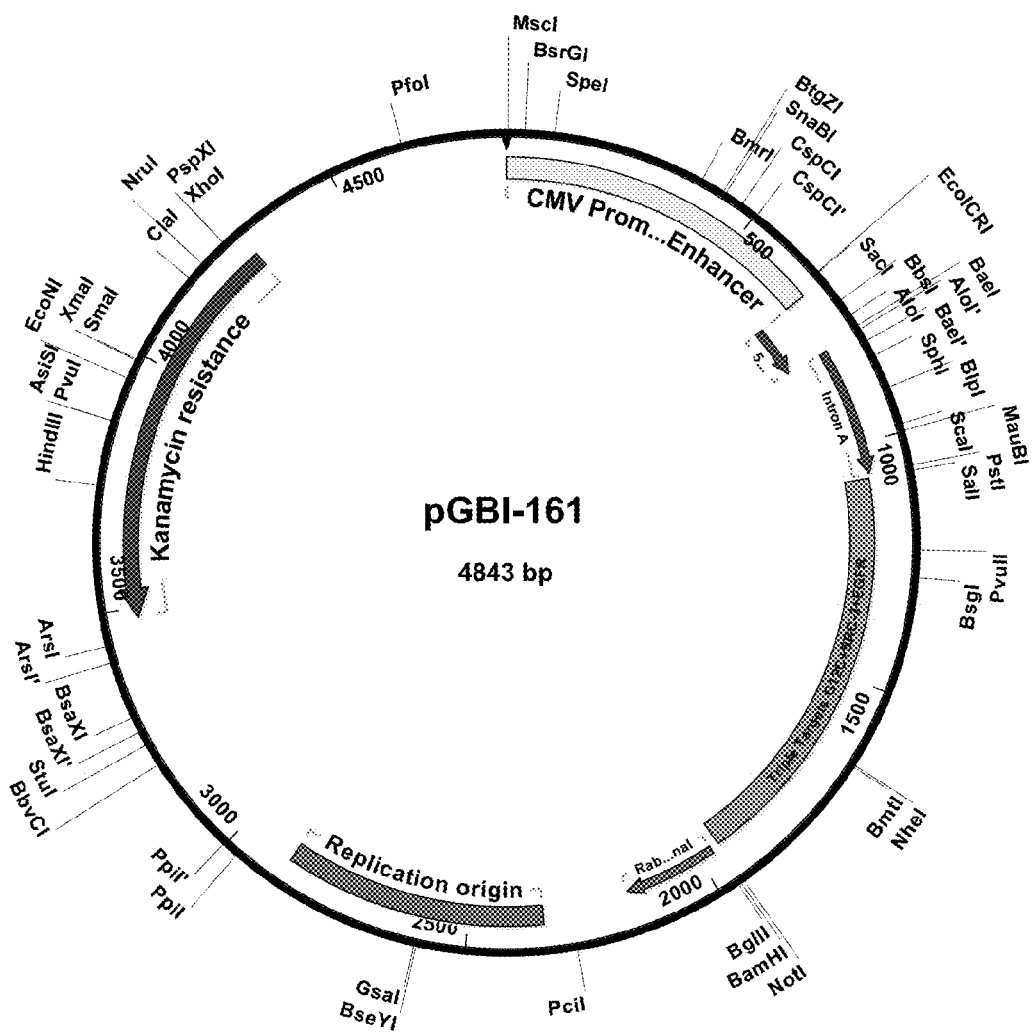
FIG. 3 shows another construct of the present invention.

FIG. 3 shows one construct of the present invention: pGBI-161.

Triple targeting bi-shRNA, targeting EGFR, KRAS G12C mutation and SRC-3. Bi-snRNA sequences are in upper case letters, pUMVC3 sequence are in lower case letters.

(SEQ ID NO:: 3)
tggccattgcatacgttgtatccatatcataatatgtacatttatatt
ggctcatgtccaacattaccgccatgttgacattgattattgactagt
tattaatagtaatcaattacggggtcattagttcatagcccatatatg
gagttccgcgttacataacttacggtaaatggcccgcctggctgaccg -continued cccaacgaccccgcccattgacgtcaataatgacgtatgttcccata
gtaacgccaatagggactttccattgacgtcaatgggtggagtattta
cggtaaactgcccacttggcagtacatcaagtgtatcatatgccaagt
acgccccctattgacgtcaatgacggtaaatggcccgcctggcattat
gcccagtacatgaccttatgggactttcctacttggcagtacatctac
gtattagtcatcgctattaccatggtgatgcggttttggcagtacatc
aatgggcgtggatagcggtttgactcacggggatttccaagtctccac
cccattgacgtcaatgggagtttgttttggcaccaaaatcaacgggac
tttccaaaatgtcgtaacaactccgccccattgacgcaaatgggcggt
aggcgtgtacggtgggaggtctatataagcagagctcgtttagtgaac
cgtcagatcgcctggagacgccatccacgctgttttgacctccataga
agacaccgggaccgatccagcctccgcggccgggaacggtgcattgga
acgcggattccccgtgccaagagtgacgtaagtaccgcctatagactc
tataggcacacccctttggctcttatgcatgctatactgtttttggct
tggggcctatacaccccgcttccttatgctataggtgatggtatagc
ttagcctataggtgtgggttattgaccattattgaccactccaacggt
ggagggcagtgtagtctgagcagtactcgttgctgccgcgcgccac
cagacataatagctgacagactaacagactgttcctttccatgggtct
tttctgcagtcaccgtcgTCGACAATTATCTATTTCAAATTTAGCAGG
AAAAAAGAGAACATCACCTTGTAAAACTGAAGATTGTGACCAGTCAGA
ATAATGTCACCTGCGTGAAGAAGTGTGATATGTGCATCTACACTTCTT
CACGCAGGTGCATTATGGTGACAGCTGCCTCGGGAAGCCAAGTTGGGC
TTTAAAGTGCAGGGCCTGCTGATGTTGAGTGCTTTTTGTTCCACCTGC
GACTAGAAGAGTAGTGAAGTAGATTAGCATCTACACTTCTTCACGCAG
GTGCATAAGAAGTTATGTATTCATCCAATAATTCAAGCCAAGCAAGTA
TATAGGTGTTTTAATAGTTTTTGTTTGCAGTCCTCTGTTTGTGGTAGT
TGGAGCTTGTAGAAGAATGTAGTACAAGCTCCAACTACCACATGGTGG
CCTGCTATTTCCTTCAAATGAATGATTTTTACTAATTTTGTGTACTTT
TATTGTGTCGATGTAGAATCTGCCTGGTCTATCTGATGTGACAGCTTC
TGTAGCACTGTGGTAGCAAGAGCTAGTGTGTTTAGTTATCTACAAGCT
CCAACTACCACATACTGCTAGCTGTAGAACTCCAGCTTCGGCCTGTCG
CCCAATCAAACTGTCCTGTTACTGAACACTGTTCTATGGTTGGAAATG
AGATGACAGTATTGTGTGATATTCTGCATACTGTCATCTCATTTCCCT
GTGGTAGTGAAAAGTCTGTAGAAAAGTAAGGGAAACTCAAACCCCTTT
CTACACGGAAATGATGCGACACTATGTGTTTCTGTATGGATACTGTCA
TCTCATTTCCTGAGTTTGGTGGGGATTGTGACCAGAAGATTTTGAAAA
TTAAATATTACTGAAGATTTCGACTTCGCggccgcggatccagatctt
tttccctctgccaaaaattatggggacatcatgaagcccttgagcat
ctgacttctggctaataaaggaaatttattttcattgcaatagtgtgt
tggaattttttgtgtctctcactcggaaggacatatgggagggcaaat
catttaaaacatcagaatgagtatttggtttagagtttggcaacatat -continued gcccattcttccgcttcctcgctcactgactcgctgcgctcggtcgtt
cggctgcggcgagcggtatcagctcactcaaaggcggtaatacggtta
tccacagaatcaggggataacgcaggaaagaacatgtgagcaaaaggc
cagcaaaaggccaggaaccgtaaaaaggccgcgttgctggcgttttc
cataggctccgcccccctgacgagcatcacaaaaatcgacgctcaagt
cagaggtggcgaaacccgacaggactataaagataccaggcgtttccc
cctggaagctccctcgtgcgctctcctgttccgaccctgccgcttacc
ggatacctgtccgcctttctcccttcgggaagcgtggcgctttctcat
agctcacgctgtaggtatctcagttcggtgtaggtcgttcgctccaag
ctgggctgtgtgcacgaaccccccgttcagcccgaccgctgcgcctta
tccggtaactatcgtcttgagtccaacccggtaagacacgacttatcg
ccactggcagcagccactggtaacaggattagcagagcgaggtatgta
ggcggtgctacagagttcttgaagtggtggcctaactacggctacact
agaagaacagtatttggtatctgcgctctgctgaagccagttaccttc
ggaaaaagagttggtagctcttgatccggcaaacaaaccaccgctggt
agcggtggtttttttgtttgcaagcagcagattacgcgcagaaaaaaa
ggatctcaagaagatcctttgatcttttctacggggtctgacgctcag
tggaacgaaaactcacgttaagggattttggtcatgagattatcaaaa
aggatcttcacctagatccttttaaattaaaaatgaagttttaaatca
atctaaagtatatatgagtaaacttggtctgacagttaccaatgctta
atcagtgaggcacctatctcagcgatctgtctatttcgttcatccata
gttgcctgactcggggggggggcgctgaggtctgcctcgtgaagaa
ggtgttgctgactcataccaggcctgaatcgccccatcatccagccag
aaagtgagggagccacggttgatgagagctttgttgtaggtggaccag
ttggtgattttgaacttttgctttgccacggaacggtctgcgttgtcg
ggaagatgcgtgatctgatccttcaactcagcaaaagttcgatttatt
caacaaagccgccgtcccgtcaagtcagcgtaatgctctgccagtgtt
acaaccaattaaccaattctgattagaaaaactcatcgagcatcaaat
gaaactgcaatttattcatatcaggattatcaataccatatttttgaa
aaagccgtttctgtaatgaaggagaaaactcaccgaggcagttccata
ggatggcaagatcctggtatcggtctgcgattccgactcgtccaacat
caatacaacctattaatttcccctcgtcaaaaataaggttatcaagtg
agaaatcaccatgagtgacgactgaatccggtgagaatggcaaaagct
tatgcatttctttccagacttgttcaacaggccagccattacgctcgt
catcaaaatcactcgcatcaaccaaaccgttattcattcgtgattgcg
cctgagcgagacgaaatacgcgatcgctgttaaaaggacaattacaaa
caggaatcgaatgcaaccggcgcaggaacactgccagcgcatcaacaa
tattttcacctgaatcaggatattcttctaatacctggaatgctgttt
cccggggatcgcagtggtgagtaaccatgcatcatcaggagtacgga
taaaatgcttgatggtcggaagaggcataaattccgtcagccagttta -continued
```
gtctgaccatctcatctgtaacatcattggcaacgctacctttgccat gtttcagaaacaactctggcgcatcgggcttcccatacaatcgataga ttgtcgcacctgattgcccgacattatcgcgagcccatttatacccat ataaatcagcatccatgttggaatttaatcgcggcctcgagcaagacg tttcccgttgaatatggctcataacaccccttgtattactgtttatgt aagcagacagttttattgttcatgatgatatattttatcttgtgcaa tgtaacatcagagattttgagacacaacgtggctttccccccccccc attattgaagcatttatcagggttattgtctcatgagcggatacatat ttgaatgtatttagaaaaataaacaatagggggttccgcgcacatttc cccgaaaagtgccacctgacgtctaagaaaccattattatcatgacat taacctataaaaataggcgtatcacgaggcccttcgtctcgcgcgtt tcggtgatgacggtgaaaacctctgacacatgcagctcccggagacgg tcacagcttgtctgtaagcggatgccgggagcagacaagcccgtcagg gcgcgtcagcgggtgttggcgggtgtcggggctggcttaactatgcgg catcagagcagattgtactgagagtgcaccatatgcggtgtgaaatac cgcacagatgcgtaaggagaaaataccgcatcagattggctat.
```

Bifunctional Sequence 161:

(SEQ ID NO:: 4)
```
TCGACAATTATCTATTTCAAATTTAGCAGGAAAAAAGAGAACATCAC

CTTGTAAAACTGAAGATTGTGACCAGTCAGAATAATGTCACCTGCGT

GAAGAAGTGTGATATGTGCATCTACACTTCTTCACGCAGGTGCATTA

TGGTGACAGCTGCCTCGGGAAGCCAAGTTGGGCTTTAAAGTGCAGGG

CCTGCTGATGTTGAGTGCTTTTTGTTCCACCTGCGACTAGAAGAGTA

GTGAAGTAGATTAGCATCTACACTTCTTCACGCAGGTGCATAAGAAG

TTATGTATTCATCCAATAATTCAAGCCAAGCAAGTATATAGGTGTTT

TAATAGTTTTTGTTTGCAGTCCTCTGTTTGTGGTAGTTGGAGCTTGT

AGAAGAATGTAGTACAAGCTCCAACTACCACATGGTGGCCTGCTATT

TCCTTCAAATGAATGATTTTTACTAATTTTGTGTACTTTTATTGTGT

CGATGTAGAATCTGCCTGGTCTATCTGATGTGACAGCTTCTGTAGCA

CTGTGGTAGCAAGAGCTAGTGTGTTTAGTTATCTACAAGCTCCAACT

ACCACATACTGCTAGCTGTAGAACTCCAGCTTCGGCCTGTCGCCCAA

TCAAACTGTCCTGTTACTGAACACTGTTCTATGGTTGGAAATGAGAT

GACAGTATTGTGTGATATTCTGCATACTGTCATCTCATTTCCCTGTG

GTAGTGAAAAGTCTGTAGAAAAGTAAGGGAAACTCAAACCCCTTTCT

ACACGGAAATGATGCGACACTATGTGTTTCTGTATGGATACTGTCAT

CTCATTTCCTGAGTTTGGTGGGGATTGTGACCAGAAGATTTTGAAAA

TTAAATATTACTGAAGATTTCGACTTCGC.
```

KRAS (Kirsten-ras) oncogene is mutated in a significant proportion of pancreatic ductal adenocarcinoma (PDAC), colorectal and non-small-cell lung cancers (NSCLC). In the majority of PDAC (70-90%) patients carrying KRAS mutations, the five year survival rate is less than 5% (Saif M W et al. World J Gastroenterol. 2007; 13; 4423-4430). KRAS is a member of guanine nucleotide-binding protein family and is an integral component of multiple intracellular signaling pathways including epidermal growth factor receptor (EGFR). The overwhelming majority of mutations in KRAS are single nucleotide somatic mutations resulting in single amino acid substitutions at codons 12 or 13. G12D, G12V, G12R and G12C KRAS mutations comprise >90% of KRAS mutations found in PADC patients. KRAS mutations essentially result in constitutively active KRAS and unregulated downstream signaling. In addition, targeted agents such as the antibody Cetuximab (in colorectal cancer) and the small molecular inhibitor vemurafenib (in BRAF mutant melanoma), perform poorly in patients with KRAS mutations. Consequently an effective cancer therapeutic strategy requires KRAS mutation selectivity sparing wild-type functionality. The present inventors have recently developed a novel bi-functional shRNA RNA interference (bi-shRNAi) technology. Bi-shRNAi allows for programmed endonuclease and non-endonuclease Argonaute protein (Ago) containing RISC (RNA-induced silencing complexes) loading to simultaneously effect mRNA cleavage, degradation, and translational repression resulting in higher potency and over longer duration than other RNAi mediators. In order to explore the potential of bi-shRNAi in KRAS mutant selective knockdown, an in vitro dual luciferase reporter assay system was established to systematically compare knockdown activity of the mutant allele and the wild-type allele in the same assay environment. The goal of this project is to develop single therapeutic agent specifically targeting G12D, G12V, G12R and G12C mutant alleles for the treatment of PDAC.

siRNA distinguish between genes that differ by single nucleotide for allelic-specific knockdown has been systematically analyzed. Allelic specific gene silencing on KRAS mutations has been reported for single G12C, G12D or G12V KRAS mutation. However, no attempt has been reported achieving multiple KRAS mutant knockdown with a single agent. The present invention includes a multi-mer approach to effect mRNA and protein expression knockdown combinations for the four key KRAS mutants of PDAC. The following are examples of specific inserts that can be used with the present invention to target K-RAS as part of the multi-mers taught there. The present invention includes these inserts, for example, each of the inserts can target the same mutation within the k-ras mRNA, or can target different K-RAS mutations, or combinations thereof. In the case of a tri-mer of inserts, one or more of the RNAi targeting inserts could be a standard shRNA or RNAi insert, or one or more could be bi-shRNAs, or combinations thereof, each targeting the same portion of the k-ras mRNA or different portions, of the same mutation or different mutations. Below are non-limiting examples of inserts that can target different mutants of K-RAS.

(SEQ ID NO: 5) G12D, position 2. With underline are miR-30a backbone sequences.

<u>TCGACTGCTGTTGAAGTGAGCGCC</u>TGTGGTAGTTGGAGCTGAT<u>TAGT

GAAGCCACAGATGTA</u>ATCAGCTCCAACTACCACA<u>GTTGCCTACTGCC

TCGGAAGCAGCTCACTACATTACTCAGCTGTTGAAGTGAGCGCC</u>TGT

GGTAGGAAGAGATGA<u>TTAGTGAAGCCACAGATGTA</u>ATCAGCTCCAAC

TACCACA<u>GTTGCCTACTGCCTCGGAAGCTTAATAAAGGATCTTTTAT

TTTCATTGGC</u>

(SEQ ID NO: 6) G12D, position 3. With underline are miR-30a backbone sequences.

<u>TCGACTGCTGTTGAAGTGAGCGCC</u>GTGGTAGTTGGAGCTGATG<u>TAGT
GAAGCCACAGATGTA</u>CATCAGCTCCAACTACCAC<u>GTTGCCTACTGCC
TCGGAAGCAGCTCACTACATTACTCAGCTGTTGAAGTGAGCGCC</u>GTG
GTAGTCTTAGCTAATG<u>TAGTGAAGCCACAGATGTA</u>CATCAGCTCCAA
CTACCAC<u>GTTGCCTACTGCCTCGGAAGCTTAATAAAGGATCTTTTAT
TTTCATTGGC</u>

(SEQ ID NO: 7) G12D, position 4. With underline are miR-30a backbone sequences.

<u>TCGACTGCTGTTGAAGTGAGCGCC</u>TGGTAGTTGGAGCTGATGG<u>TAGT
GAAGCCACAGATGTA</u>CCATCAGCTCCAACTACCA<u>GTTGCCTACTGCC
TCGGAAGCAGCTCACTACATTACTCAGCTGTTGAAGTGAGCGCC</u>TGG
TAGTTACTGCTAATGG<u>TAGTGAAGCCACAGATGTA</u>CCATCAGCTCCA
ACTACCA<u>GTTGCCTACTGCCTCGGAAGCTTAATAAAGGATCTTTTAT
TTTCATTGGC</u>

(SEQ ID NO: 8) G12D, position 5. With underline are miR-30a backbone sequences.

<u>TCGACTGCTGTTGAAGTGAGCGCC</u>GGTAGTTGGAGCTGATGGC<u>TAGT
GAAGCCACAGATGTA</u>GCCATCAGCTCCAACTACC<u>GTTGCCTACTGCC
TCGGAAGCAGCTCACTACATTACTCAGCTGTTGAAGTGAGCGCC</u>GGT
AGTTGTCTCTGATAGC<u>TAGTGAAGCCACAGATGTA</u>GCCATCAGCTCC
AACTACC<u>GTTGCCTACTGCCTCGGAAGCTTAATAAAGGATCTTTTAT
TTTCATTGGC</u>

(SEQ ID NO: 9) G12D, position 6. With underline are miR-30a backbone sequences.

<u>TCGACTGCTGTTGAAGTGAGCGCC</u>GTAGTTGGAGCTGATGGCG<u>TAGT
GAAGCCACAGATGTA</u>CGCCATCAGCTCCAACTAC<u>GTTGCCTACTGCC
TCGGAAGCAGCTCACTACATTACTCAGCTGTTGAAGTGAGCGCC</u>GTA
GTTGGAGCTGATGGCG<u>TAGTGAAGCCACAGATGTA</u>CGCCATCAGCTC
CAACTAC<u>GTTGCCTACTGCCTCGGAAGCTTAATAAAGGATCTTTTAT
TTTCATTGGC</u>

(SEQ ID NO: 10) G12D, position 7. With underline are miR-30a backbone sequences.

<u>TCGACTGCTGTTGAAGTGAGCGCC</u>TAGTTGGAGCTGATGGCGT<u>TAGT
GAAGCCACAGATGTA</u>ACGCCATCAGCTCCAACTA<u>GTTGCCTACTGCC
TCGGAAGCAGCTCACTACATTACTCAGCTGTTGAAGTGAGCGCC</u>TAG
TTGGATGAGATGACGT<u>TAGTGAAGCCACAGATGTA</u>ACGCCATCAGCT

CCAACTA<u>GTTGCCTACTGCCTCGGAAGCTTAATAAAGGATCTTTTAT
TTTCATTGGC</u>

(SEQ ID NO: 11) G12D, position 8. With underline are miR-30a backbone sequences.

<u>TCGACTGCTGTTGAAGTGAGCGCC</u>AGTTGGAGCTGATGGCGTA<u>TAGT
GAAGCCACAGATGTA</u>TACGCCATCAGCTCCAACT<u>GTTGCCTACTGCC
TCGGAAGCAGCTCACTACATTACTCAGCTGTTGAAGTGAGCGCC</u>AGT
TGGAGACTATGGAGTA<u>TAGTGAAGCCACAGATGTA</u>TACGCCATCAGC
TCCAACT<u>GTTGCCTACTGCCTCGGAAGCTTAATAAAGGATCTTTTAT
TTTCATTGGC</u>

(SEQ ID NO: 12) G12D, position 9.

TCGACTGCTGTTGAAGTGAGCGCCGTTGGAGCTGATGGCGTAGTAGT
GAAGCCACAGATGTACTACGCCATCAGCTCCAACGTTGCCTACTGCC
TCGGAAGCAGCTCACTACATTACTCAGCTGTTGAAGTGAGCGCCGTT
GAAGCACGTGGTGTAGTAGTGAAGCCACAGATGTACTACGCCATCAG
CTCCAACGTTGCCTACTGCCTCGGAAGCTTAATAAAGGATCTTTTAT
TTTCATTGGC (SEQ ID NO: 13) G12D, POSITION 10.

TCGACTGCTGTTGAAGTGAGCGCCTTGGAGCTGATGGCGTAGGTAGT
GAAGCCACAGATGTACCTACGCCATCAGCTCCAAGTTGCCTACTGCC
TCGGAAGCAGCTCACTACATTACTCAGCTGTTGAAGTGAGCGCCTTG
GAGCTATAGGTCTAGGTAGTGAAGCCACAGATGTACCTACGCCATCA
GCTCCAAGTTGCCTACTGCCTCGGAAGCTTAATAAAGGATCTTTTAT
TTTCATTGGC (SEQ ID NO: 14) G12D, POSITION 11.

TCGACTGCTGTTGAAGTGAGCGCCTGGAGCTGATGGCGTAGGCTAGT
GAAGCCACAGATGTAGCCTACGCCATCAGCTCCAGTTGCCTACTGCC
TCGGAAGCAGCTCACTACATTACTCAGCTGTTGAAGTGAGCGCCTGG
AGCTGTATGCGTTCGCTAGTGAAGCCACAGATGTAGCCTACGCCATC
AGCTCCAGTTGCCTACTGCCTCGGAAGCTTAATAAAGGATCTTTTAT
TTTCATTGGC (SEQ ID NO: 15) G12D, POSITION 9, MOD 4.

TCGACTGCTGTTGAAGTGAGCGCCGTTGGAGCTGATGGCGTAGTAGT
GAAGCCACAGATGTACTATGCCATCAGCTCCAACGTTGCCTACTGCC
TCGGAAGCAGCTCACTACATTACTCAGCTGTTGAAGTGAGCGCCGTT
GAAGCACGTGGTGTAGTAGTGAAGCCACAGATGTACTATGCCATCAG

CTCCAACGTTGCCTACTGCCTCGGAAGCTTAATAAAGGATCTTTTAT

TTTCATTGGC (SEQ ID NO: 16) G12D, position 10, mod 5.

TCGACTGCTGTTGAAGTGAGCGCCttggagctgAtggcgtaggTAGT

GAAGCCACAGATGTACCTATGCCATCAGCTCCAAGTTGCCTACTGCC

TCGGAAGCAGCTCACTACATTACTCAGCTGTTGAAGTGAGCGCCttg gagctATAggTCtaggTAGTGAAGCCACAGATGTACCTATGCCATCA

GCTCCAAGTTGCCTACTGCCTCGGAAGCTTAATAAAGGATCTTTTAT

TTTCATTGGC (SEQ ID NO: 17) G12D, POSITION 11, MOD 6.

TCGACTGCTGTTGAAGTGAGCGCCtggagctgAtggcgtaggcTAGT

GAAGCCACAGATGTAGCCTATGCCATCAGCTCCAGTTGCCTACTGCC

TCGGAAGCAGCTCACTACATTACTCAGCTGTTGAAGTGAGCGCCtgg agctgTATgcgtTCgcTAGTGAAGCCACAGATGTAGCCTATGCCATC

AGCTCCAGTTGCCTACTGCCTCGGAAGCTTAATAAAGGATCTTTTAT

TTTCATTGGC (SEQ ID NO: 18) G12D, POSITION 9, MOD 10.

TCGACTGCTGTTGAAGTGAGCGCCgttggagctCAtggcgtagTAGT

GAAGCCACAGATGTACTACGCCATGAGCTCCAACGTTGCCTACTGCC

TCGGAAGCAGCTCACTACATTACTCAGCTGTTGAAGTGAGCGCCgtt gaagcACGtgGTgtagTAGTGAAGCCACAGATGTACTACGCCATGAG

CTCCAACGTTGCCTACTGCCTCGGAAGCTTAATAAAGGATCTTTTAT

TTTCATTGGC (SEQ ID NO: 19) G12D, position 10, mod 11.

TCGACTGCTGTTGAAGTGAGCGCCttggagctCAtggcgtaggTAG

TGAAGCCACAGATGTACCTACGCCATGAGCTCCAAGTTGCCTACTG

CCTCGGAAGCAGCTCACTACATTACTCAGCTGTTGAAGTGAGCGCC ttggagctATAggTCtaggTAGTGAAGCCACAGATGTACCTACGCC

ATGAGCTCCAAGTTGCCTACTGCCTCGGAAGCTTAATAAAGGATCT

TTTATTTTCATTGGC (SEQ ID NO: 20) G12D, position 11, mod 12.

TCGACTGCTGTTGAAGTGAGCGCCTGGAGCTCATGGCGTAGGCTAG

TGAAGCCACAGATGTAGCCTACGCCATGAGCTCCAGTTGCCTACTG

CCTCGGAAGCAGCTCACTACATTACTCAGCTGTTGAAGTGAGCGCC

TGGAGCTGTATGCGTTCGCTAGTGAAGCCACAGATGTAGCCTACGC

CATGAGCTCCAGTTGCCTACTGCCTCGGAAGCTTAATAAAGGATCT

TTTATTTTCATTGGC (SEQ ID NO: 21) G12V, position 3.

TCGACTGCTGTTGAAGTGAGCGCCGTGGTAGTTGGAGCTGTTGTAG

TGAAGCCACAGATGTACAACAGCTCCAACTACCACGTTGCCTACTG

CCTCGGAAGCAGCTCACTACATTACTCAGCTGTTGAAGTGAGCGCC

GTGGTAGTCTTAGCTATTGTAGTGAAGCCACAGATGTACAACAGCT

CCAACTACCACGTTGCCTACTGCCTCGGAAGCTTAATAAAGGATCT

TTTATTTTCATTGGC (SEQ ID NO: 22) G12V, position 4.

TCGACTGCTGTTGAAGTGAGCGCCTGGTAGTTGGAGCTGTTGGTAG

TGAAGCCACAGATGTACCAACAGCTCCAACTACCAGTTGCCTACTG

CCTCGGAAGCAGCTCACTACATTACTCAGCTGTTGAAGTGAGCGCC

TGGTAGTTACTGCTATTGGTAGTGAAGCCACAGATGTACCAACAGC

TCCAACTACCAGTTGCCTACTGCCTCGGAAGCTTAATAAAGGATCT

TTTATTTTCATTGGC (SEQ ID NO: 23) G12R, position 3.

TCGACTGCTGTTGAAGTGAGCGCCTGTGGTAGTTGGAGCTCGTTAG

TGAAGCCACAGATGTAACGAGCTCCAACTACCACAGTTGCCTACTG

CCTCGGAAGCAGCTCACTACATTACTCAGCTGTTGAAGTGAGCGCC

TGTGGTAGACTGAGCTAGTTAGTGAAGCCACAGATGTAACGAGCTC

CAACTACCACAGTTGCCTACTGCCTCGGAAGCTTAATAAAGGATCT

TTTATTTTCATTGGC (SEQ ID NO: 24) G12R, position 4.

TCGACTGCTGTTGAAGTGAGCGCCGTGGTAGTTGGAGCTCGTGTAG

TGAAGCCACAGATGTACACGAGCTCCAACTACCACGTTGCCTACTG

CCTCGGAAGCAGCTCACTACATTACTCAGCTGTTGAAGTGAGCGCC

GTGGTAGTACTAGCTAGTGTAGTGAAGCCACAGATGTACACGAGCT

CCAACTACCACGTTGCCTACTGCCTCGGAAGCTTAATAAAGGATCT

TTTATTTTCATTGGC (SEQ ID NO: 25) G12C, position 3.

TCGACTGCTGTTGAAGTGAGCGCCTGTGGTAGTTGGAGCTTGTTAG

TGAAGCCACAGATGTAACAAGCTCCAACTACCACAGTTGCCTACTG

CCTCGGAAGCAGCTCACTACATTACTCAGCTGTTGAAGTGAGCGCC

TGTGGTAGACTGAGCTAGTTAGTGAAGCCACAGATGTAACAAGCTC

-continued

```
CAACTACCACAGTTGCCTACTGCCTCGGAAGCTTAATAAAGGATCT
TTTATTTTCATTGGC
```

(SEQ ID NO: 26) G12C, position 4.

```
TCGACTGCTGTTGAAGTGAGCGCCGTGGTAGTTGGAGCTTGTGTAG
TGAAGCCACAGATGTACACAAGCTCCAACTACCACGTTGCCTACTG
CCTCGGAAGCAGCTCACTACATTACTCAGCTGTTGAAGTGAGCGCC
GTGGTAGTCTTAGCTTATGTAGTGAAGCCACAGATGTACACAAGCT
CCAACTACCACGTTGCCTACTGCCTCGGAAGCTTAATAAAGGATCT
TTTATTTTCATTGGC
```

SRC-3 bishRNA 140 (SEQ ID NO: 27):

```
TCGACTGCTGTTGAAGTGAGCGCCGTTGTCAATATAGATACAATAG
TGAAGCCACAGATGTATTGTATCTATATTGACAACGTTGCCTACTG
CCTCGGAAGCAGCTCACTACATTACTCAGCTGTTGAAGTGAGCGCC
GTTGTCAATGCTGATCCAATAGTGAAGCCACAGATGTATTGTATCT
ATATTGACAACGTTGCCTACTGCCTCGGAAGCTTAATAAAGGATCT
TTTATTTTCATTGGC.
```

The double underlined sequence region corresponds to the sense sequence (nucleotide 1090-1108), wherein the underlined region corresponds to the antisense sequence.

SRC-3 bishRNA 141 (SEQ ID NO: 28):

```
TCGACTGCTGTTGAAGTGAGCGCAAAGCAAACTCTTCCGAAATAG
TGAAGCCACAGATGTATTTCGGAAGAGTTTGCTTTGTTGCCTACTG
CCTCGGAAGCAGCTCACTACATTACTCAGCTGTTGAAGTGAGCGCC
AAAGCAAATACTTCTGAAATAGTGAAGCCACAGATGTATTTCGGAA
GAGTTTGCTTTGTTGCCTACTGCCTCGGAAGCTTAATAAAGGATCT
TTTATTTTCATTGGC.
```

The double underlined sequence region corresponds to the sense sequence (nucleotide 1304-1322), wherein the underlined region corresponds to the antisense sequence.

SRC-3 bishRNA 142 (SEQ ID NO: 29):

```
TCGACTGCTGTTGAAGTGAGCGCCGTTGTCAATATAGATACAATAG
TGAAGCCACAGATGTATTGTATCTATATTGACAACGTTGCCTACTG
CCTCGGAAGCAGCTCACTACATTACTCAGCTGTTGAAGTGAGCGCC
GAGGAAGAGAGAGGTAAGTTAGTGAAGCCACAGATGTAACTGACCT
GGTTCTTCCTCGTTGCCTACTGCCTCGGAAGCTTAATAAAGGATCT
TTTATTTTCATTGGC.
```

The double underlined sequence region corresponds to the sense sequence, wherein the underlined region corresponds to the antisense sequence.

SRC-3 bishRNA 143 (SEQ ID NO: 30):

```
TCGACTGCTGTTGAAGTGAGCGCCAAAGCAAACTCTTCCGAAATAG
TGAAGCCACAGATGTATTTCGGAAGAGTTTGCTTTGTTGCCTACTG
CCTCGGAAGCAGCTCACTACATTACTCAGCTGTTGAAGTGAGCGCC
GAGGAAGAGAGAGGTAAGTTAGTGAAGCCACAGATGTAACTGACCT
GGTTCTTCCTCGTTGCCTACTGCCTCGGAAGCTTAATAAAGGATCT
TTTATTTTCATTGGC.
```

The double underlined sequence region corresponds to the sense sequence, wherein the underlined region corresponds to the antisense sequence.

SRC-3 bishRNA 144 (SEQ ID NO: 31):

```
TCGACTGCTGTTGAAGTGAGCGCCCTATATGGTAGAGCAATATAG
TGAAGCCACAGATGTATATTGCTCTACCATATAGGGTTGCCTACTG
CCTCGGAAGCAGCTCACTACATTACTCAGCTGTTGAAGTGAGCGCC
CCTATATGCATGATCAATATAGTGAAGCCACAGATGTATATTGCTC
TACCATATAGGGTTGCCTACTGCCTCGGAAGCTTAATAAAGGATCT
TTTATTTTCATTGGC.
```

The double underlined sequence region corresponds to the sense sequence, wherein the underlined region corresponds to the antisense sequence.

SRC-3 bishRNA 145 (SEQ ID NO: 32):

```
TCGACTGCTGTTGAAGTGAGCGCCGGAAATGAGATGACAGTATTAG
TGAAGCCACAGATGTAATACTGTCATCTCATTTCCGTTGCCTACTG
CCTCGGAAGCAGCTCACTACATTACTCAGCTGTTGAAGTGAGCGCC
GGAAATGACTAGACACTATTAGTGAAGCCACAGATGTAATACTGTC
ATCTCATTTCCGTTGCCTACTGCCTCGGAAGCTTAATAAAGGATCT
TTTATTTTCATTGGC.
```

The double underlined sequence region corresponds to the sense sequence (nucleotide 1090-1108), wherein the underlined region corresponds to the antisense sequence.

SRC-3 bishRNA 146 (SEQ ID NO: 33):

```
TCGACTGCTGTTGAAGTGAGCGCCATGGAAGGTACAGGAATATTAG
TGAAGCCACAGATGTAATATTCCTGTACCTTCCATGTTGCCTACTG
CCTCGGAAGCAGCTCACTACATTACTCAGCTGTTGAAGTGAGCGCC
ATGGAAGGACTAGTAATATTAGTGAAGCCACAGATGTAATATTCCT
GTACCTTCCATGTTGCCTACTGCCTCGGAAGCTTAATAAAGGATCT
TTTATTTTCATTGGC.
```

The double underlined sequence region corresponds to the sense sequence (nucleotide 1684-1702), wherein the underlined region corresponds to the antisense sequence.

SRC-3 bishRNA 147 (SEQ ID NO: 34):

TCGACTGCTGTTGAAGTGAGCGCC<u><u>TCATGGGAATTCATATCATTA</u></u>

GTGAAGCCACAGATGTA<u>ATGATATGAATTCCCATGA</u>GTTGCCTAC

TGCCTCGGAAGCAGCTCACTACATTACTCAGCTGTTGAAGTGAGC

GCC<u><u>TCATGGGACAACATCTCATT</u></u>AGTGAAGCCACAGATGTA<u>ATGA</u>

<u>TATGAATTCCCATGA</u>GTTGCCTACTGCCTCGGAAGCTTAATAAAG

GATCTTTTATTTTCATTGGC.

The double underlined sequence region corresponds to the sense sequence (nucleotide 1331-1349), wherein the underlined region corresponds to the antisense sequence.

SRC-3 bishRNA 148 (SEQ ID NO: 35):

TCGACTGCTGTTGAAGTGAGCGCC<u><u>CCACCAATCAGAAACAGTATA</u></u>

GTGAAGCCACAGATGTA<u>TACTGTTTCTGATTGGTGGG</u>TTGCCTAC

TGCCTCGGAAGCAGCTCACTACATTACTCAGCTGTTGAAGTGAGC

GCC<u><u>CCACCAATGTCAAATAGTAT</u></u>AGTGAAGCCACAGATGTA<u>TACT</u>

<u>GTTTCTGATTGGTGGG</u>TTGCCTACTGCCTCGGAAGCTTAATAAAG

GATCTTTTATTTTCATTGGC.

The double underlined sequence region corresponds to the sense sequence (nucleotide 2791-2809), wherein the underlined region corresponds to the antisense sequence.

SRC-3 bishRNA 149 (SEQ ID NO: 36):

TCGACTGCTGTTGAAGTGAGCGCC<u><u>GGAGGAGATTGATAGAGCCTA</u></u>

GTGAAGCCACAGATGTA<u>GGCTCTATCAATCTCCT</u>CCGTTGCCTAC

TGCCTCGGAAGCAGCTCACTACATTACTCAGCTGTTGAAGTGAGC

GCC<u><u>GGAGGAGACATATACAGCC</u></u>TAGTGAAGCCACAGATGTA<u>GGCT</u>

<u>CTATCAATCTCCT</u>CCGTTGCCTACTGCCTCGGAAGCTTAATAAAG

GATCTTTTATTTTCATTGGC.

The double underlined sequence region corresponds to the sense sequence (nucleotide 3361-3381), wherein the underlined region corresponds to the antisense sequence.

Breast cancers, constructs. The following construct was generated: Generate a PI3K E545K+SRC-3+ER-α (NR3A1) targeting vector.

Figure 4:
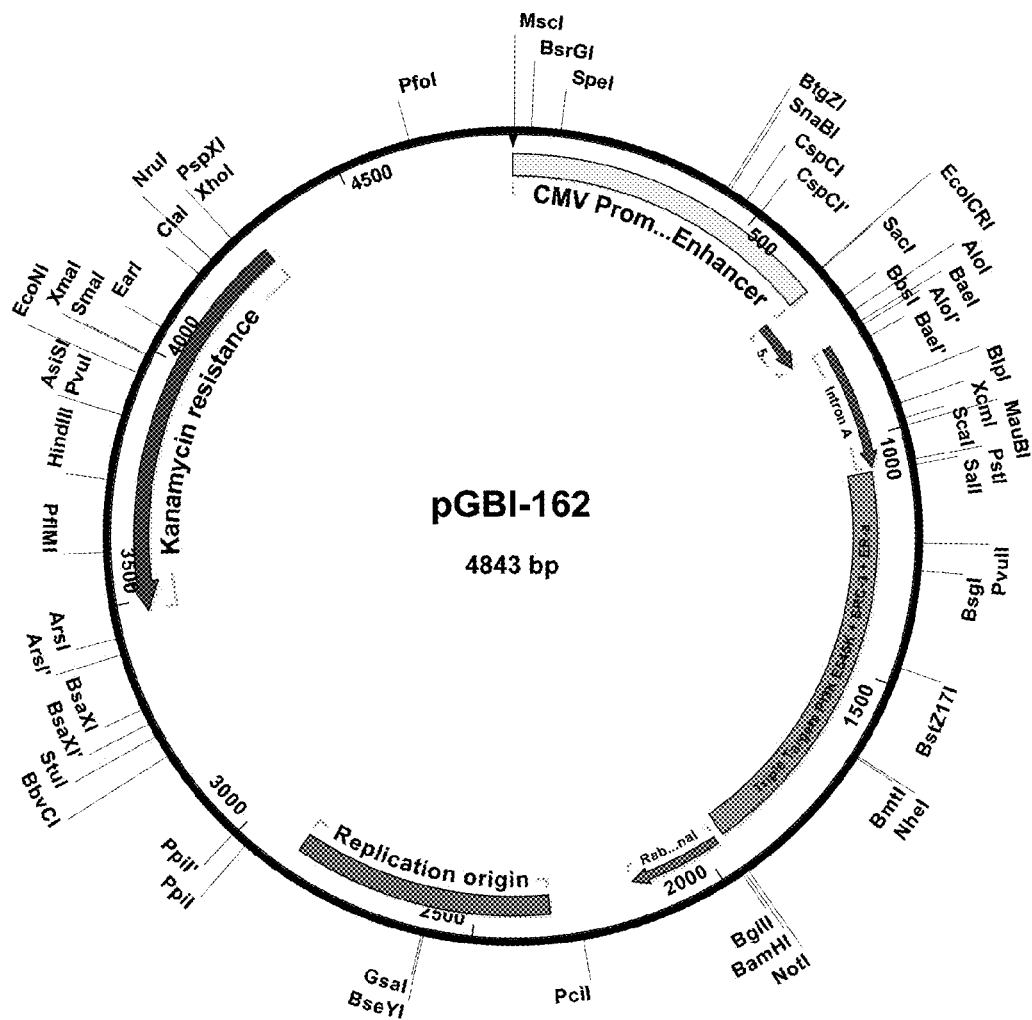
FIG. 4 shows a vector map for pGBI-162: wherein the insert includes RNAis against PI3K E545K+SRC-3+ER-α (NR3A1) targeting vector, as outlined below.

FIG. 4 shows a vector map for pGBI-162: wherein the insert includes RNAis against PI3K E545K+SRC-3+ER-α (NR3A1) targeting vector, as outlined below.

P13K E545K:

SEQ ID NO: 37
AAAGCAATTTCTACACGAGATCCTCTCTCTGAAATCACTAAGCAG
GAGA

Sense:
SEQ ID NO: 38
5' TCTCTCTGAAATCACTAAG 3'

Antisense:
SEQ ID NO: 39
5' CTTAGTGATTTCAGAGAGA 3' bi-shRNA-NCOA3-5 (pGBI-48). 3'UTR region
Sense sequence:
SEQ ID NO: 40
5' *GGAAATGAGATGACAGTAT* 3'

Antisense sequence:
SEQ ID NO: 41
5' *ATACTGTCATCTCATTTCC* 3'

Estrogen Receptor 1α:

Sense:
SEQ ID NO: 42
5' <u>CCAGTGCACCATTGATAAA</u> 3'

Antisense:
SEQ ID NO: 43
5' <u>TTTATCAATGGTGCACTGG</u> 3'

Insert sequence: The inserts are bolded (PI3K-E545K), italicized (NCOAA3-5), or underlined (ER1alpha), as outlined above.

SEQ ID NO: 44
AATTATCTATTTCAAATTTAGCAGGAAAAAAGAGAACATCACCTT

GTAAAACTGAAGATTGTGACCAGTCAGAATAATGTTCTCTCTGAA

ATCACTAAGGATATGTGCATCTCTTAGTGATTTCAGAGAGACATT

ATGGTGACAGCTGCCTCGGGAAGCCAAGTTGGGCTTTAAAGTGCA

GGGCCTGCTGATGTTGAGTGCTTTTTGTTCTCTCTCTGCTGTCAC

TTAGAGTGAAGTAGATTAGCATCTCTTAGTGATTTCAGAGAGACA

TAAGAAGTTATGTATTCATCCAATAATTCAAGCCAAGCAAGTATA

TAGGTGTTTTAATAGTTTTTGTTTGCAGTCCTCTGTT*GGAAATGA*

*TGCGACACTA*TAGAAGAATGTAGTATACTGTCATCTCATTTCCTG

GTGGCCTGCTATTTCCTTCAAATGAATGATTTTTACTAATTTTGT

GTACTTTTATTGTGTCGATGTAGAATCTGCCTGGTCTATCTGATG

TGACAGCTTCTGTAGCAC*GGAAATGAGATGACAGTAT*GTGTTTAG

TTATCTATACTGTCATCTCATTTCCTACTGCTAGCTGTAGAACTC

CAGCTTCGGCCTGTCGCCCAATCAAACTGTCCTGTTACTGAACAC

TGTTCTATGGTT<u>CCAGTGCACCATTGATAAA</u>TGTGTGATATTCTG

CTTTATCAATGGTGCACTGGCTGTGGTAGTGAAAAGTCTGTAGAA

AAGTAAGGGAAACTCAAACCCCTTTCTACAC<u>CCAGTGCATGCTTG</u>

<u>ATAAA</u>GTGTTTCTGTATGGTTTATCAATGGTGCACTGGTGAGTTT

GGTGGGGATTGTGACCAGAAGATTTTGAAAATTAAATATTACTGA

AGATTTCGACTTC

Figure 5:
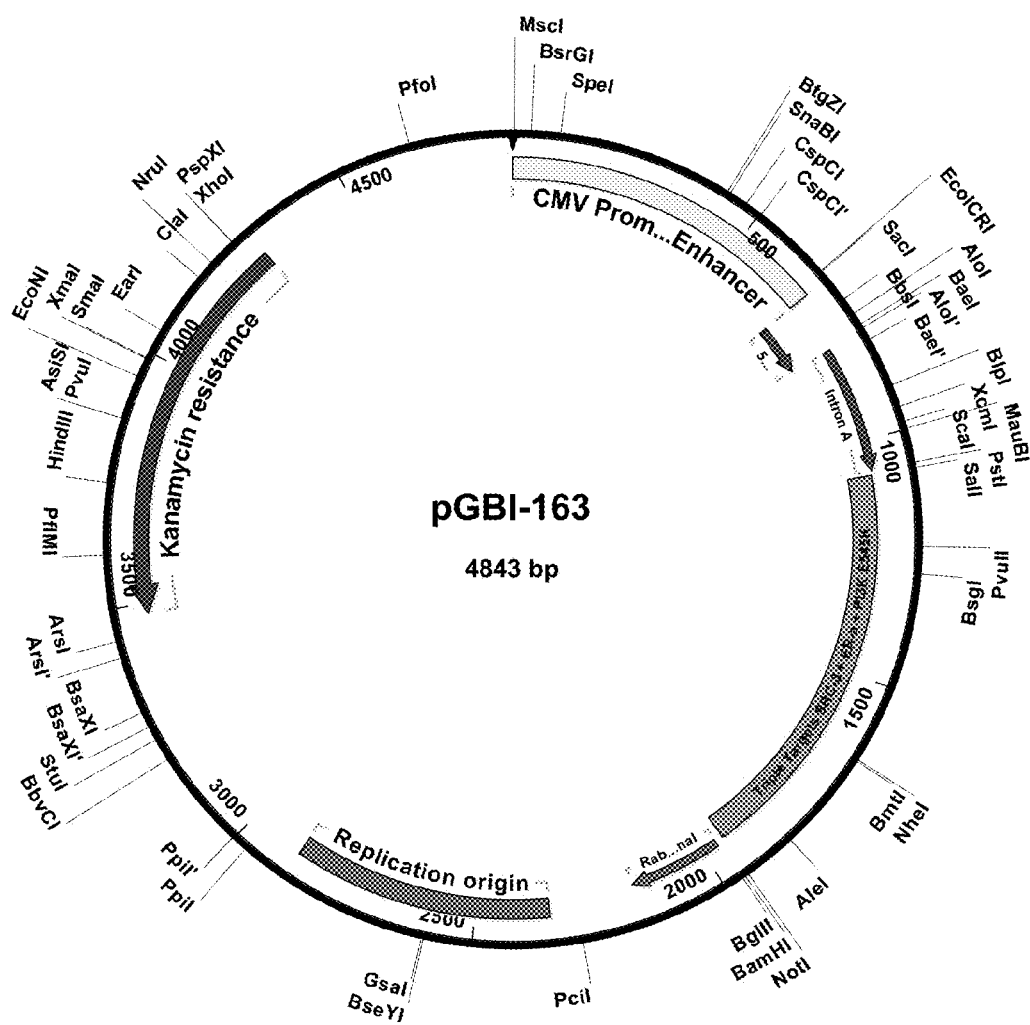
FIG. 5 shows a vector map for pGBI-162: pGBI-163: SRC-3+ER-α (NR3A1)+PI3K E545K targeting vector.

FIG. 5 shows a vector map for pGBI-162: pGBI-163: SRC-3+ER-α (NR3A1)+PI3K E545K targeting vector:

bi-shRNA-NCOA3-5 (pGBI-48): 3'UTR region

Sense sequence:
SEQ ID NO: 40
5' GGAAATGAGATGACAGTAT 3'

Antisense sequence:
SEQ ID NO: 41
5' ATACTGTCATCTCATTTCC 3'

Estrogen Receptor 1α:

Sense:
SEQ ID NO: 42
5' *CCAGTGCACCATTGATAAA* 3'

Antisenes:
SEQ ID NO: 43
5' TTTATCAATGGTGCACTGG 3'

PI3K E545K:

SEQ ID NO: 37
AAAGCAATTTCTACACGAGATCCTCTCTCTGAAATCACTAAGCAGGAGA

Sense:
SEQ ID NO: 38
5' <u>TCTCTCTGAAATCACTAAG</u> 3'

Antisense:
SEQ ID NO: 39
5' CTTAGTGATTTCAGAGAGA 3'

Insert sequence: The inserts are bolded (NCOA3-5), italicized (ER1alpha), or underlined (PI3K-E545K), as shown above.

SEQ ID NO: 45
AATTATCTATTTCAAATTTAGCAGGAAAAAAGAGAACATCACCTTGTAAAACTGAAGATTGTGACCAGTCAGAATAATGTGGAAATGATGCGACACTATGATATGTGCATCTATACTGTCATCTCATTTCCCATTATGGTGACAGCTGCCTCGGGAAGCCAAGTTGGGCTTTAAAGTGCAGGGCCTGCTGATGTTGAGTGCTTTTTGTTCGGAAATGAGATGACAGTATAGTGAAGTAGATTAGCATCTATACTGTCATCTCATTTCCATAAGAAGTTATGTATTCATCCAATAATTCAAGCCAAGCAAGTATATAGGTGTTTTAATAGTTTTTGTTTGCAGTCCTCTGTT*CCAGTGCACCATTGATAAA*AGAAGAATGTAGTTTTATCAATGGTGCACTGGTGGTGGCCTGCTATTTCCTTCAAATGAATGATTTTTACTAATTTTGTGTACTTTTATTGTGTCGATGTAGAATCTGCCTGGTCTATCTGATGTGACAGCTTCTGTAGCAC*CCAGTGCATGCTTGATAAAGTGTTTAG*TTATCTTTTATCAATGGTGCACTGGTACTGCTAGCTGTAGAACTCCAGCTTCGGCCTGTCGCCCAATCAAACTGTCCTGTTACTGAACACTGTTCTATGGTT<u>TCTCTCTGAAATCACTAAG</u>TGTGTGATATTCTGCCTTAGTGATTTCAGAGAGACTGTGGTAGTGAAAAGTCTGTAGAAAAGTAAGGGAAACTCAAACCCCTTTCTACAC<u>TCTCTCTGCTGTCACTTAGG</u>TGTTTCTGTATGGCTTAGTGATTTCAGAGAGATGAGTTTGGTGGGGATTGTGACCAGAAGATTTTGAAAATTAAATATTACTGAAGATTTCGACTTC pGBI-162: Complete sequence, insert in uppercase tggccattgcatacgttgtatccatatcataatatgtacatttat
attggctcatgtccaacattaccgccatgttgacattgattattg
actagttattaatagtaatcaattacggggtcattagttcatagc
ccatatatggagttccgcgttacataacttacggtaaatggcccg
cctggctgaccgcccaacgacccccgcccattgacgtcaataatg
acgtatgttcccatagtaacgccaatagggactttccattgacgt
caatgggtggagtatttacggtaaactgcccacttggcagtacat
caagtgtatcatatgccaagtacgccccctattgacgtcaatgac
ggtaaatggcccgcctggcattatgcccagtacatgaccttatgg
gactttcctacttggcagtacatctacgtattagtcatcgctatt
accatggtgatgcggttttggcagtacatcaatgggcgtggatag
cggtttgactcacggggatttccaagtctccaccccattgacgtc
aatgggagtttgttttggcaccaaaatcaacgggactttccaaaa
tgtcgtaacaactccgccccattgacgcaaatgggcggtaggcgt
gtacggtgggaggtctatataagcagagctcgtttagtgaaccgt
cagatcgcctggagacgccatccacgctgttttgacctccataga
agacaccgggaccgatccagcctccgcggccgggaacggtgcatt
ggaacgcggattcccgtgccaagagtgacgtaagtaccgcctat
agactctataggcacacccetttggctcttatgcatgctatactg
ttttttggcttggggcctatacaccccgcttecttatgctatagg
tgatggtatagcttagcctataggtgtgggttattgaccattatt
gaccactccaacggtggagggcagtgtagtctgagcagtactcgt
tgctgccgcgcgcgccaccagacataatagctgacagactaacag
actgttccttttccatgggtcttttctgcagtcaccgtcgTCGACAATTATCTATTTCAAATTTAGCAGGAAAAAAGAGAACATCACCTTGTAAAACTGAAGATTGTGACCAGTCAGAATAATGTTCTCTCTGAAATCACTAAGGATATGTGCATCTCTTAGTGATTTCAGAGAGACATTATGGTGACAGCTGCCTCGGGAAGCCAAGTTGGGCTTTAAAGTGCAGGGCCTGCTGATGTTGAGTGCTTTTTGTTCTCTCTCTGCTGTCACTTAGAGTGAAGTAGATTAGCATCTCTTAGTGATTTCAGAGAGACATAAGAAGTTATGTATTCATCCAATAATTCAAGCCAAGCAAGTATATAGGTGTTTTAATAGTTTTTGTTTGCAGTCCTCTGTTGGAAATGATGCGACACTATAGAAGAATGTAGTATACTGTCATCTCATTTCCTGGTGGCCTGCTATTTCCTTCAAATGAATGATTTTTACTAATTTTGTGTACTTTTATTGTGTCGATGTAGAATCTGCCTGGTCTATCTGATGTGACAGCTTCTGTAGCACGGAAATGAGATGACAGTATGTGTTTAGT

```
TATCTATACTGTCATCTCATTTCCTACTGCTAGCTGTAGAACTCC

AGCTTCGGCCTGTCGCCCAATCAAACTGTCCTGTTACTGAACACT

GTTCTATGGTTCCAGTGCACCATTGATAAATGTGTGATATTCTGC

TTTATCAATGGTGCACTGGCTGTGGTAGTGAAAAGTCTGTAGAAA

AGTAAGGGAAACTCAAACCCCTTTCTACACCCAGTGCATGCTTGA

TAAAGTGTTTCTGTATGGTTTATCAATGGTGCACTGGTGAGTTTG

GTGGGGATT
```

SEQ ID NO: 46
```
GTGACCAGAAGATTTTGAAAATTAAATATTACTGAAGATTTCGAC

TTCGCGGCCGCGGATCCAgatcttttccctctgccaaaaattat ggggacatcatgaagcccttgagcatctgacttctggctaataa aggaaatttattttcattgcaatagtgtgttggaattttttgtgt ctctcactcggaaggacatatgggagggcaaatcatttaaaacat cagaatgagtatttggtttagagtttggcaacatatgcccattct tccgcttcctcgctcactgactcgctgcgctcggtcgttcggctg cggcgagcggtatcagctcactcaaaggcggtaatacggttatcc acagaatcaggggataacgcaggaaagaacatgtgagcaaaaggc cagcaaaaggccaggaaccgtaaaaaggccgcgttgctggcgttt ttccataggctccgcccccctgacgagcatcacaaaaatcgacgc tcaagtcagaggtggcgaaacccgacaggactataaagataccag gcgtttccccctggaagctccctcgtgcgctctcctgttccgacc ctgccgcttaccggatacctgtccgcctttctcccttcgggaagc gtggcgctttctcatagctcacgctgtaggtatctcagttcggtg taggtcgttcgctccaagctgggctgtgtgcacgaaccccccgtt cagcccgaccgctgcgccttatccggtaactatcgtcttgagtcc aacccggtaagacacgacttatcgccactggcagcagccactggt aacaggattagcagagcgaggtatgtaggcggtgctacagagttc ttgaagtggtggcctaactacggctacactagaagaacagtattt ggtatctgcgctctgctgaagccagttaccttcggaaaaagagtt ggtagctcttgatccggcaaacaaaccaccgctggtagcggtggt ttttttgtttgcaagcagcagattacgcgcagaaaaaaaggatct caagaagatcctttgatcttttctacggggtctgacgctcagtgg aacgaaaactcacgttaagggattttggtcatgagattatcaaaa aggatcttcacctagatccttttaaattaaaaatgaagttttaaa tcaatctaaagtatatatgagtaaacttggtctgacagttaccaa tgcttaatcagtgaggcacctatctcagcgatctgtctatttcgt tcatccatagttgcctgactcggggggggggggcgctgaggtctg cctcgtgaagaaggtgttgctgactcataccaggcctgaatcgcc ccatcatccagccagaaagtgagggagccacggttgatgagagct ttgttgtaggtggaccagttggtgattttgaacttttgctttgcc
```

```
acggaacggtctgcgttgtcgggaagatgcgtgatctgatccttc aactcagcaaaagttcgatttattcaacaaagccgccgtcccgtc aagtcagcgtaatgctctgccagtgttacaaccaattaaccaatt ctgattagaaaaactcatcgagcatcaaatgaaactgcaatttat tcatatcaggattatcaataccatattttgaaaaagccgtttct gtaatgaaggagaaaactcaccgaggcagttccataggatggcaa gatcctggtatcggtctgcgattccgactcgtccaacatcaatac aacctattaatttcccctcgtcaaaaataaggttatcaagtgaga aatcaccatgagtgacgactgaatccggtgagaatggcaaaagct tatgcatttctttccagacttgttcaacaggccagccattacgct cgtcatcaaaatcactcgcatcaaccaaaccgttattcattcgtg attgcgcctgagcgagacgaaatacgcgatcgctgttaaaaggac aattacaaacaggaatcgaatgcaaccggcgcaggaacactgcca gcgcatcaacaatattttcacctgaatcaggatattcttctaata cctggaatgctgttttcccggggatcgcagtggtgagtaaccatg catcatcaggagtacggataaaatgcttgatggtcggaagaggca taaattccgtcagccagtttagtctgaccatctcatctgtaacat cattggcaacgctaccttgccatgtttcagaaacaactctggcg catcgggcttcccatacaatcgatagattgtcgcacctgattgcc cgacattatcgcgagcccatttatacccatataaatcagcatcca tgttggaatttaatcgcggcctcgagcaagacgtttcccgttgaa tatggctcataacaccccttgtattactgtttatgtaagcagaca gttttattgttcatgatgatatatttttatcttgtgcaatgtaac atcagagattttgagacacaacgtggctttcccccccccccatt attgaagcatttatcagggttattgtctcatgagcggatacatat ttgaatgtatttagaaaaataaacaaataggggttccgcgcacat ttccccgaaaagtgccacctgacgtctaagaaaccattattatca tgacattaacctataaaaataggcgtatcacgaggccctttcgtc tcgcgcgtttcggtgatgacggtgaaaacctctgacacatgcagc tcccggagacggtcacagcttgtctgtaagcggatgccgggagca gacaagcccgtcagggcgcgtcagcgggtgttggcgggtgtcggg gctggcttaactatgcggcatcagagcagattgtactgagagtgc accatatgcggtgtgaaataccgcacagatgcgtaaggagaaaat accgcatcagattggctat
``` pGBI-163: Complete sequence Complete sequence, insert in uppercase

SEQ ID NO: 47
```
tggccattgcatacgttgtatccatatcataatatgtacatttat attggctcatgtccaacattaccgccatgttgacattgattattg actagttattaatagtaatcaattacggggtcattagttcatagc
```

```
ccatatatggagttccgcgttacataacttacggtaaatggcccg
cctggctgaccgcccaacgacccccgcccattgacgtcaataatg
acgtatgttcccatagtaacgccaatagggactttccattgacgt
caatgggtggagtatttacggtaaactgcccacttggcagtacat
caagtgtatcatatgccaagtacgccccctattgacgtcaatgac
ggtaaatggcccgcctggcattatgcccagtacatgaccttatgg
gactttcctacttggcagtacatctacgtattagtcatcgctatt
accatggtgatgcggttttggcagtacatcaatgggcgtggatag
cggtttgactcacggggatttccaagtctccaccccattgacgtc
aatgggagtttgttttggcaccaaaatcaacgggactttccaaaa
tgtcgtaacaactccgccccattgacgcaaatgggcggtaggcgt
gtacggtgggaggtctatataagcagagctcgtttagtgaaccgt
cagatcgcctggagacgccatccacgctgttttgacctccataga
agacaccgggaccgatccagcctccgcggccgggaacggtgcatt
ggaacgcggattccccgtgccaagagtgacgtaagtaccgccat
agactctataggcacacccctttggctcttatgcatgctatactg
tttttggcttggggcctatacaccccgcttccttatgctatagg
tgatggtatagcttagcctataggtgtgggttattgaccattatt
gaccactccaacggtggagggcagtgtagtctgagcagtactcgt
tgctgccgcgcgcgccaccagacataatagctgacagactaacag
actgttcctttccatgggtcttttctgcagtcaccgtcgTCGACA
ATTATCTATTTCAAATTTAGCAGGAAAAAAGAGAACATCACCTTG
TAAAACTGAAGATTGTGACCAGTCAGAATAATGTGGAAATGATGC
GACACTATGATATGTGCATCTATACTGTCATCTCATTTCCCATTA
TGGTGACAGCTGCCTCGGGAAGCCAAGTTGGGCTTTAAAGTGCAG
GGCCTGCTGATGTTGAGTGCTTTTTGTTCGGAAATGAGATGACAG
TATAGTGAAGTAGATTAGCATCTATACTGTCATCTCATTTCCCAT
AAGAAGTTATGTATTCATCCAATAATTCAAGCCAAGCAAGTATAT
AGGTGTTTTAATAGTTTTTGTTTGCAGTCCTCTGTTCCAGTGCAC
CATTGATAAAAGAAGAATGTAGTTTTATCAATGGTGCACTGGTGG
TGGCCTGCTATTTCCTTCAAATGAATGATTTTTACTAATTTTGTG
TACTTTTATTGTGTCGATGTAGAATCTGCCTGGTCTATCTGATGT
GACAGCTTCTGTAGCACCCAGTGCATGCTTGATAAAGTGTTTAGT
TATCTTTTATCAATGGTGCACTGGTACTGCTAGCTGTAGAACTCC
AGCTTCGGCCTGTCGCCCAATCAAACTGTCCTGTTACTGAACACT
GTTCTATGGTTTCTCTCTGAAATCACTAAGTGTGTGATATTCTGC
CTTAGTGATTTCAGAGAGACTGTGGTAGTGAAAAGTCTGTAGAAA
AGTAAGGGAAACTCAAACCCCTTTCTACACTCTCTCTGCTGTCAC
TTAGGTGTTTCTGTATGGCTTAGTGATTTCAGAGAGATGAGTTTG
GTGGGGATTGTGACCAGAAGATTTTGAAAATTAAATATTACTGAA
GATTTCGACTTCGCGGCCGCGGATCCAgatcttttttcctctgcc
```

```
aaaaattatggggacatcatgaagcccttgagcatctgacttct
ggctaataaaggaaatttattttcattgcaatagtgtgttggaat
tttttgtgtctctcactcggaaggacatatgggagggcaaatcat
ttaaaacatcagaatgagtatttggtttagagtttggcaacatat
gcccattcttccgcttcctcgctcactgactcgctgcgctcggtc
gttcggctgcggcgagcggtatcagctcactcaaaggcggtaata
cggttatccacagaatcaggggataacgcaggaaagaacatgtga
gcaaaaggccagcaaaaggccaggaaccgtaaaaaggccgcgttg
ctggcgttttccataggctccgcccccctgacgagcatcacaaa
aatcgacgctcaagtcagaggtggcgaaacccgacaggactataa
agataccaggcgtttccccctggaagctccctcgtgcgctctcct
gttccgaccctgccgcttaccggatacctgtccgcctttctccct
tcgggaagcgtggcgctttctcatagctcacgctgtaggtatctc
agttcggtgtaggtcgttcgctccaagctgggctgtgtgcacgaa
ccccccgttcagcccgaccgctgcgccttatccggtaactatcgt
cttgagtccaacccggtaagacacgacttatcgccactggcagca
gccactggtaacaggattagcagagcgaggtatgtaggcggtgct
acagagttcttgaagtggtggcctaactacggctacactagaaga
acagtatttggtatctgcgctctgctgaagccagttaccttcgga
aaaagagttggtagctcttgatccggcaaacaaaccaccgctggt
agcggtggtttttttgtttgcaagcagcagattacgcgcagaaaa
aaaggatctcaagaagatcctttgatcttttctacggggtctgac
gctcagtggaacgaaaactcacgttaagggattttggtcatgaga
ttatcaaaaaggatcttcacctagatccttttaaattaaaaatga
agttttaaatcaatctaaagtatatatgagtaaacttggtctgac
agttaccaatgcttaatcagtgaggcacctatctcagcgatctgt
ctatttcgttcatccatagttgcctgactcggggggggggggcgc
tgaggtctgcctcgtgaagaaggtgttgctgactcataccaggcc
tgaatcgccccatcatccagccagaaagtgagggagccacggttg
atgagagctttgttgtaggtggaccagttggtgattttgaacttt
tgctttgccacggaacggtctgcgttgtcgggaagatgcgtgatc
tgatccttcaactcagcaaaagttcgatttattcaacaaagccgc
cgtcccgtcaagtcagcgtaatgctctgccagtgttacaaccaat
taaccaattctgattagaaaaactcatcgagcatcaaatgaaact
gcaatttattcatatcaggattatcaataccatattttgaaaaa
gccgtttctgtaatgaaggagaaaactcaccgaggcagttccata
ggatggcaagatcctggtatcggtctgcgattccgactcgtccaa
catcaatacaacctattaatttcccctcgtcaaaaataaggttat
```

-continued

```
caagtgagaaatcaccatgagtgacgactgaatccggtgagaatg gcaaaagcttatgcatttctttccagacttgttcaacaggccagc cattacgctcgtcatcaaaatcactcgcatcaaccaaaccgttat tcattcgtgattgcgcctgagcgagacgaaatacgcgatcgctgt taaaaggacaattacaaacaggaatcgaatgcaaccggcgcagga acactgccagcgcatcaacaatattttcacctgaatcaggatatt cttctaatacctggaatgctgttttcccggggatcgcagtggtga gtaaccatgcatcatcaggagtacggataaaatgcttgatggtcg gaagaggcataaattccgtcagccagtttagtctgaccatctcat ctgtaacatcattggcaacgctacctttgccatgtttcagaaaca actctggcgcatcgggcttcccatacaatcgatagattgtcgcac ctgattgcccgacattatcgcgagcccatttatacccatataaat cagcatccatgttggaatttaatcgcggcctcgagcaagacgttt cccgttgaatatggctcataacacccctttgtattactgtttatgt aagcagacagttttattgttcatgatgatatattttttatcttgtg caatgtaacatcagagattttgagacacaacgtggctttccccc cccccattattgaagcatttatcagggttattgtctcatgagcg gatacatatttgaatgtatttagaaaaataaacaaatagggttc cgcgcacatttccccgaaaagtgccacctgacgtctaagaaacca ttattatcatgacattaacctataaaaataggcgtatcacgaggc cctttcgtctcgcgcgtttcggtgatgacggtgaaaacctctgac acatgcagctcccggagacggtcacagcttgtctgtaagcggatg ccgggagcagacaagcccgtcagggcgcgtcagcgggtgttggcg ggtgtcggggctggcttaactatgcggcatcagagcagattgtac
``` tgagagtgcaccatatgcggtgtgaaataccgcacagatgcgtaa ggagaaaataccgcatcagattggctat

EGFR target based on Homo sapiens epidermal growth factor receptor (EGFR), transcript variant 1, mRNA, NCBI Reference Sequence: NM_005228.3.

```
EGFR Target sequence:
                                     SEQ ID NO: 48
5' CACCTGCGTGAAGAAGTGT 5'

EGFR Target Guide strand:
                                     SEQ ID NO: 49
5' ACACTTCTTCACGCAGGTG 3'
```

Non-limiting examples of Bifunctional shRNAs targeting SRC-3 are highly effective and have the advantage of causing RNAi at concentrations significantly lower than conventional shRNA or siRNA. The present inventors have developed bishRNAs to optimally target SRC-3 to reduce its expression. FIG. 5 shows cell growth assays were performed to examine the ability of SRC-3 and SRC-1 bi-shRNA vectors to block breast cancer cell growth. MCF-7 cells were transfected with SRC-1 and SRC-3 bio-shRNA vectors and their effects on cell proliferation were measured via MTT assay after four (FIGS. 6A and 6B) days. All SRC targeting vectors were able to effectively reduce cell growth in contrast to the negative control (siGFP). Similarly, inhibition of growth is also observed on MDA-MB-231 cells transfected with SRC-1 and SCR-3 bi-shRNA vectors. These results confirm that bi-shRNA based targeting of SRC-1 and SRC-3 can reduce breast cancer cell growth in vitro.

Figure 6A:
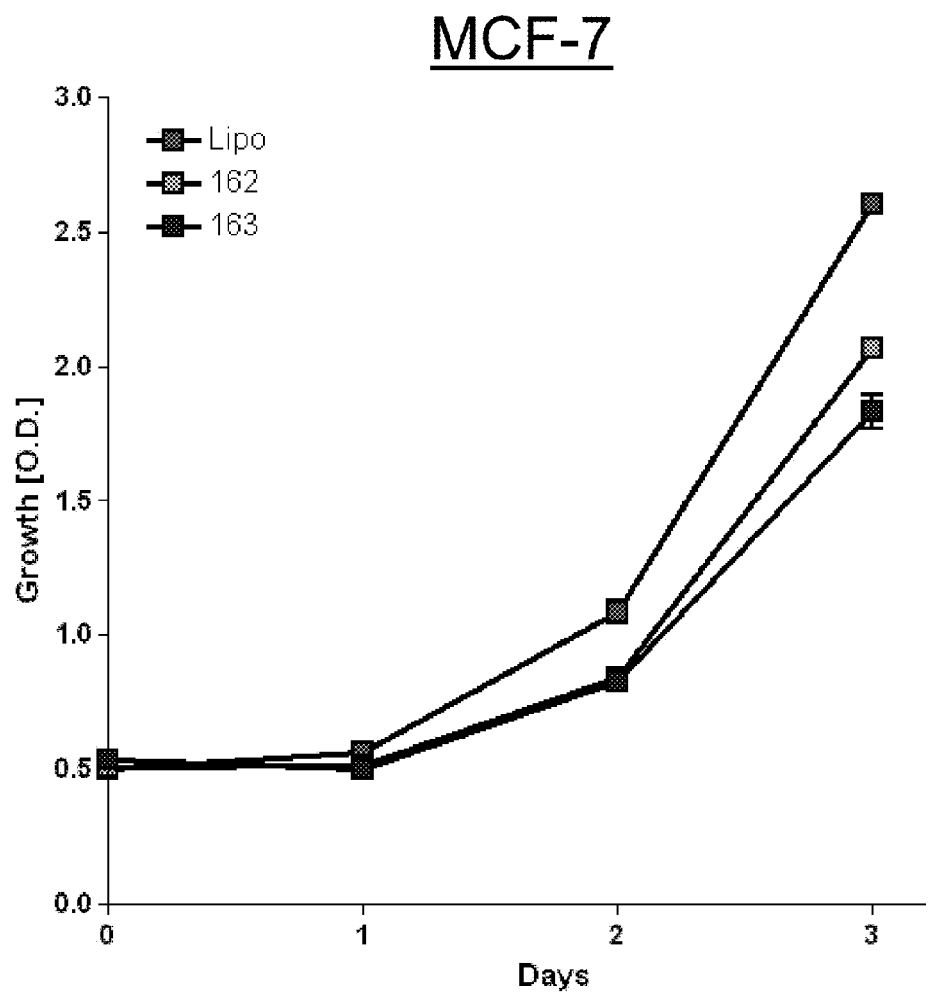
FIG. 6A is a graph that shows the change in growth.
Figure 6B:
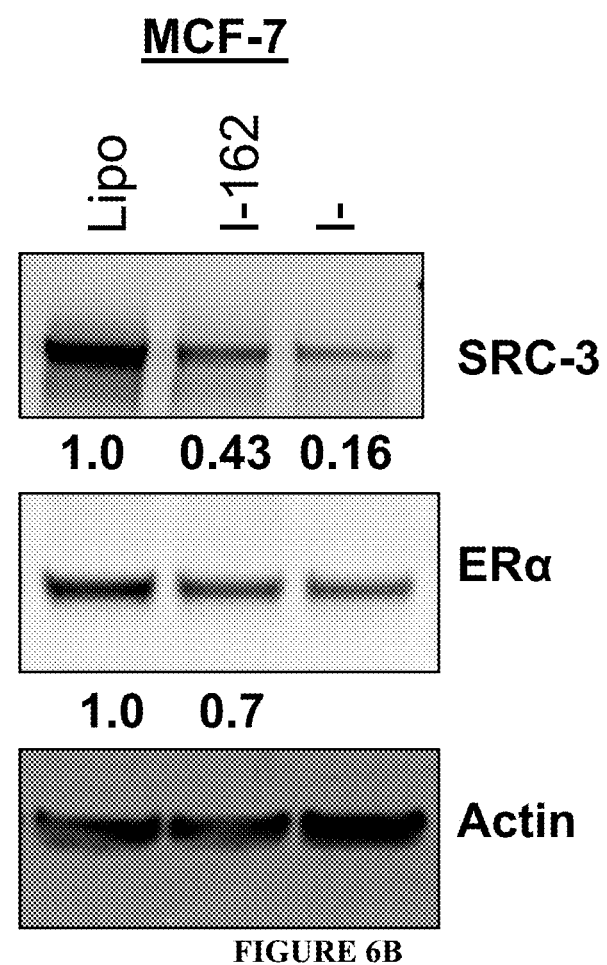
FIG. 6B is a blot shows the results obtained against an MCF-7 breast cancer cell line using the constructs shown in FIGS. 5 and 6 of the present invention, namely: pGBI-162: PI3K E545K+SRC-3+ER-α (NR3A1) targeting vector, and pGBI-163: SRC-3+ER-α (NR3A1)+PI3K E545K targeting vector.

FIG. 6A is a graph that shows the change in growth, and FIG. 6B is a blot shows the results obtained against an MCF-7 breast cancer cell line using the constructs shown in FIGS. 5 and 6 of the present invention, namely: pGBI-162: PI3K E545K+SRC-3+ER-α (NR3A1) targeting vector, and pGBI-163: SRC-3+ER-α (NR3A1)+PI3K E545K targeting vector.

Table 1. Additional shRNA targeting sequences for use in the multimeric targeting vector.

| Target Gene | Gene Function | Species | Sequence of Target | Region of Target | SEQ ID NO: |
|---|---|---|---|---|---|
| STMN1 | Structual, regulation of microtubule | Human | 5' GCTGACTAATTTGTTCTGA 3' | Coding region | 50 |
| STMN1 | Structual, regulation of microtubule | Human | 5' GGCACAAATGGCTGCCAAA 3' | Coding region | 51 |
| STMN1 | Structual, regulation of microtubule | Rat | 5' GGCGCAAATGGCTGCCAAG 3' | Coding region | 52 |
| ASAH1 | Enzyme, lipid metabolism | Human | 5' AATCAACCTATCCTCCTTC 3' | Coding region | 53 |
| ASAH1 | Enzyme, lipid metabolism | Human | 5' AAAATCAACCTATCCTCCT 3' | Coding region | 54 |
| FURIN | Enzyme, proprotein convertase | Human | 5' GTTTTGATGTCAATGACCA 3' | Coding region | 55 |
| FURIN | Enzyme, proprotein convertase | Human | 5 GGAGAAAGGAGTGAAACCT 3' | 3'-UTR | 56 |

-continued

| Target Gene | Gene Function | Species | Sequence of Target | Region of Target | SEQ ID NO:: |
|---|---|---|---|---|---|
| FURIN | Enzyme, proprotein convertase | Human | 5' CAGCTGCGCTCTGGCTTTA 3' | Coding region | 57 |
| PDX1 | Transcription activator | Human | 5' AGTTCCTATTCAACAAGTA 3' | Coding region | 58 |
| PDX1 | Transcription activator | Human | 5' CAGTTATTTACAAACAGGT 3' | 3'-UTR | 59 |
| PDX1 | Transcription activator | Mouse | 5' GGAAGATAAGAAACGTAGT 3' | Coding region | 60 |
| TACSTD2 | Cell Surface Receptor | Human | 5' GGAAGGGATGGCATAGCGT 3' | 3'-UTR | 61 |
| TACSTD2 | Cell Surface Receptor | Human | 5' GCCTCATTTACCATCGTTT 3' | 3'-UTR | 62 |
| TACSTD2 | Cell Surface Receptor | Human, Mouse | 5' TGGACAACGATGGCCTCTA 3' | coding region | 63 |
| MSLN | Cytokine and Cell Surface Receptor | Human | 5' GCCTCATCTTCTACAAGAA 3' | Coding region | 64 |
| MSLN | Cytokine and Cell Surface Receptor | Human, Mouse | 5' CCAGGACCAGCAGGAGGCA 3' | Coding region | 65 |
| SLC39A4 | Iron regulated transporter | Human | 5' ACAGCAGCGAGGTCCCTAT 3' | Coding region | 66 |
| SLC39A4 | Iron regulated transporter | Human | 5' ACGTAGCACTCTGCGACAT 3' | Coding region | 67 |
| NCOA1 | Transcriptional cofactor | Human, Mouse | 5' ATGGAAGGTACAGGAATAT 3' | Coding Region | 68 |
| NCOA1 | Transcriptional cofactor | Human, Mouse | 5' TCATGGGAATTCATATCAT 3' | Coding Region | 69 |
| NCOA2 | Transcriptional cofactor | Human, Mouse | 5' CCACCAATCAGAAACAGTA 3' | Coding Region | 70 |
| NCOA2 | Transcriptional cofactor | Human | 5' GGAGGAGATTGATAGAGCC 3' | Coding Region | 71 |
| NCOA3 | Transcriptional cofactor | Human | 5' GTTGTCAATATAGATACAA 3' | Coding Region | 72 |
| NCOA3 | Transcriptional cofactor | Human, Mouse | 5' AAAGCAAACTCTTCCGAAA 3' | Coding Region | 73 |
| NCOA3 | Transcriptional cofactor | Human | 5' GTTGTCAATATAGATACAA 3' | Coding + 3'UTR | 74 |
| NCOA3 | Transcriptional cofactor | Human | 5' GAGGAAGAACCAGGTCAGT 3' | Coding + 3'UTR | 75 |
| NCOA3 | Transcriptional cofactor | Human | 5' AAAGCAAACTCTTCCGAAA 3' | Coding + 3'UTR | 76 |
| NCOA3 | Transcriptional cofactor | Human | 5' GAGGAAGAACCAGGTCAGT 3' | Coding + 3'UTR | 77 |
| NCOA3 | Transcriptional cofactor | Human | 5' GGAAATGAGATGACAGTAT 3' | 3' UTR | 78 |
| NCOA3 | Transcriptional cofactor | Human | 5' CCTATATGGTAGAGCAATA 3' | 3' UTR | 79 |

-continued

| Target Gene | Gene Function | Species | Sequence of Target | Region of Target | SEQ ID NO: |
|---|---|---|---|---|---|
| EFNB1 | Cell adhesion | Human | 5' GAAGCACCATGATTACTAC 3' | Coding region | 80 |
| EFNB1 | Cell adhesion | Human | 5' CAGCCAGGAAGCATAGGAT 3' | 3' UTR | 81 |
| CCNE1 | Cell cycle control | Human | 5' AGAGGAAGGCAAACGTGAC 3' | coding region | 82 |
| CCNE1 | Cell cycle control | Human | 5' CAAACTTGAGGAAATCTAT 3' | coding region | 83 |
| CCNE1 | Cell cycle control | Human | 5' TGGAGGTGTGTGAAGTCTA 3' | coding region | 84 |
| CCNE1 | Cell cycle control | Human | 5' AGAGGAAGGCAAACGTGAC 3' | coding region and 3'UTR | 85 |
| CCNE1 | Cell cycle control | Human | 5' TGTTTTGTAAGTGCTGCTA 3' | coding region and 3'UTR | 86 |
| KRAS | Signal transducer | Human, Mouse | 5' GTTGGAGCTGATGGCGTAG 3' | Kras mutation | 87 |
| KRAS | Signal transducer | Human, Mouse | 5' TTGGAGCTGATGGCGTAGG 3' | Kras mutation | 88 |
| KRAS | Signal transducer | Human, Mouse | 5' TGGAGCTGATGGCGTAGGC 3' | Kras mutation | 89 |
| KRAS | Signal transducer | Human, Mouse | 5' GTTGGAGCTGATGGCGTAG 3' | Kras mutation | 90 |
| KRAS | Signal transducer | Human, Mouse | 5' TTGGAGCTGATGGCGTAGG 3' | Kras mutation | 91 |
| KRAS | Signal transducer | Human, Mouse | 5' TGGAGCTGATGGCGTAGGC 3' | Kras mutation | 92 |
| KRAS | Signal transducer | Human, Mouse | 5' GTTGGAGCTGATGGCGTAG 3' | Kras mutation | 93 |
| KRAS | Signal transducer | Human, Mouse | 5' TTGGAGCTGATGGCGTAGG 3' | Kras mutation | 94 |
| KRAS | Signal transducer | Human, Mouse | 5' TGGAGCTGATGGCGTAGGC 3' | Kras mutation | 95 |
| hRLU | Reporter | Human | 5' GGCCTTTCACTACTCCTAC 3' | coding region | 96 |
| hRLU | Reporter | Human | 5' GAGCGAAGAGGGCGAGAAA 3' | coding region | 97 |
| KRAS | Signal transducer | Human, Mouse | 5' TGTGGTAGTTGGAGCTGAT 3' | Kras mutation | 98 |
| KRAS | Signal transducer | Human, Mouse | 5' GTGGTAGTTGGAGCTGATG 3' | Kras mutation | 99 |
| KRAS | Signal transducer | Human, Mouse | 5' TGGTAGTTGGAGCTGATGG 3' | Kras mutation | 100 |
| KRAS | Signal transducer | Human, Mouse | 5' GGTAGTTGGAGCTGATGGC 3' | Kras mutation | 101 |
| KRAS | Signal transducer | Human, Mouse | 5' GTAGTTGGAGCTGATGGCG 3' | Kras mutation | 102 |
| KRAS | Signal transducer | Human, Mouse | 5' TAGTTGGAGCTGATGGCGT 3' | Kras mutation | 103 |

-continued

| Target Gene | Gene Function | Species | Sequence of Target | Region of Target | SEQ ID NO:: |
|---|---|---|---|---|---|
| KRAS | Signal transducer | Human, Mouse | 5' AGTTGGAGCTGATGGCGTA 3' | Kras mutation | 104 |
| KRAS | Signal transducer | Human, Mouse | 5' GTGGTAGTTGGAGCTGATG 3' | Kras mutation | 105 |
| KRAS | Signal transducer | Human, Mouse | 5' GTGGTAGTTGGAGCTGATG 3' | Kras mutation | 106 |
| KRAS | Signal transducer | Human, Mouse | 5' GTGGTAGTTGGAGCTGATG 3' | Kras mutation | 107 |
| KRAS | Signal transducer | Human, Mouse | 5' TGGTAGTTGGAGCTGATGG 3' | Kras mutation | 108 |
| KRAS | Signal transducer | Human, Mouse | 5' TGGTAGTTGGAGCTGATGG 3' | Kras mutation | 109 |
| KRAS | Signal transducer | Human, Mouse | 5' GTGGTAGTTGGAGCTGTTG 3' | Kras mutation | 110 |
| KRAS | Signal transducer | Human, Mouse | 5' TGGTAGTTGGAGCTGTTGG 3' | Kras mutation | 111 |
| KRAS | Signal transducer | Human, Mouse | 5' GTGGTAGTTGGAGCTGTTG 3' | Kras mutation | 112 |
| KRAS | Signal transducer | Human, Mouse | 5' TGGTAGTTGGAGCTGTTGG 3' | Kras mutation | 113 |
| KRAS | Signal transducer | Human, Mouse | 5' TGTGGTAGTTGGAGCTCGT 3' | Kras mutation | 114 |
| KRAS | Signal transducer | Human, Mouse | 5' TGTGGTAGTTGGAGCTTGT 3' | Kras mutation | 115 |
| KRAS | Signal transducer | Human, Mouse | 5' GTGGTAGTTGGAGCTCGTG 3' | Kras mutation | 116 |
| KRAS | Signal transducer | Human, Mouse | 5' GTGGTAGTTGGAGCTTGTG 3' | Kras mutation | 117 |
| AR | Hormone receptor | Human | 5' CAGAAATGATTGCACTATT 3' | coding region | 118 |
| AR | Hormone receptor | Human | 5' CAGCCTGTTGAACTCTTCT 3' | 5'-UTR | 119 |
| AR | Hormone receptor | Human, Mouse | 5' ACGAGGCAGCTGCGTACCA 3' | coding region | 120 |
| AR | Hormone receptor | Human, Mouse | 5' GCAGGAAGCAGTATCCGAA 3' | coding region | 121 |
| EWS-FLI1 | Transcription activator | Junction Human | 5' CTACGGGCAGCAGAACCCT 3' | region | 122 |
| EWS-FLI1 | Transcription activator | Junction Human | 5' CGGGCAGCAGAGTTCACTG 3' | region | 123 |
| EWS-FLI1 | Transcription activator | Junction Human | 5' TCTTGATCAGACCCTTCT 3' | region | 124 |
| EWS-FLI1 | Transcription activator | Junction Human | 5' AGATCTTGATCTAGGTTCA 3' | region | 125 |
| EWS-ERG | Transcription activator | Junction Human | 5' CTACGGGCAGCAGAATTTA 3' | region | 126 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±0.1, 0.5, 1, 2, 3, 4, 5, 6, 7, 8, 9, 10, 11, 12, 13, 14 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Ohnishi Y, Tokunaga K, Kaneko K, Hohjoh H. Assessment of allele-specific gene silencing by RNA interference with mutant and wild-type reporter alleles. J RNAi Gene Silencing. 2006 Feb. 28; 2(1):154-60.

2. Huang H, Qiao R, Zhao D, Zhang T, Li Y, Yi F, Lai F, Hong J, Ding X, Yang Z, Zhang L, Du Q, Liang Z. Profiling of mismatch discrimination in RNAi enabled rational design of allele-specific siRNAs. Nucleic Acids Res. 2009 December; 37(22):7560-9.

3. Schwarz DS, Ding H, Kennington L, Moore JT, Schelter J, Burchard J, Linsley PS, Aronin N, Xu Z, Zamore PD. Designing siRNA that distinguish between genes that differ by a single nucleotide. PLoS Genet. 2006 Sep. 8; 2(9):e140.

4. Geng CM, Ding HL. Design of functional small interfering RNAs targeting amyotrophic lateral sclerosis-associated mutant alleles. Chin Med J (Engl). 2011 January; 124(1):106-10.

5. Brummelkamp TR, Bernards R, Agami R. Stable suppression of tumorigenicity by virus-mediated RNA interference. Cancer Cell. 2002 September; 2(3):243-7.

6. Fleming JB, Shen GL, Holloway SE, Davis M, Brekken RA. Molecular consequences of silencing mutant K-ras in pancreatic cancer cells: justification for K-ras-directed therapy. Mol Cancer Res. 2005 July; 3(7):413-23.

7. Zhang Z, Jiang G, Yang F, Wang J. Knockdown of mutant K-ras expression by adenovirus-mediated siRNA inhibits the in vitro and in vivo growth of lung cancer cells. Cancer Biol Ther. 2006 November; 5(11):1481-6.

8. Smakman N, Veenendaal LM, van Diest P, Bos R, Offringa R, Borel Rinkes IH, Kranenburg O. Dual effect of Kras(D12) knockdown on tumorigenesis: increased immune-mediated tumor clearance and abrogation of tumor malignancy. Oncogene. 2005 Dec. 15; 24(56):8338-42.

9. Zhang YA, Nemunaitis J, Samuel SK, Chen P, Shen Y, Tong AW. Antitumor activity of an oncolytic adenovirus-delivered oncogene small interfering RNA. Cancer Res. 2006 Oct. 1; 66(19):9736-43.

10. Sierant M, Paduszynska A, Kazmierczak-Baranska J, Nacmias B, Sorbi S, Bagnoli S, Sochacka E, Nawrot B. Specific Silencing of L392V PSEN1 Mutant Allele by RNA Interference. Int J Alzheimers Dis. 2011 Apr. 7; 2011: 809218.

11. de Yñigo-Mojado L, Martin-Ruiz I, Sutherland JD. Efficient allele-specific targeting of LRRK2 R1441 mutations mediated by RNAi. PLoS One. 2011; 6(6):e21352.

12. Takahashi M, Watanabe S, Murata M, Furuya H, Kanazawa I, Wada K, Hohjoh H. Tailor-made RNAi knockdown against triplet repeat disease-causing alleles. Proc Natl Acad Sci USA. 2010 Dec. 14; 107(50):21731-6.

13. Pfister EL, Kennington L, Straubhaar J, Wagh S, Liu W, DiFiglia M, Landwehrmeyer B, Vonsattel JP, Zamore PD, Aronin N. Five siRNAs targeting three SNPs may provide therapy for three-quarters of Huntington's disease patients. Curr Biol. 2009 May 12; 19(9):774-8.

14. Rao DD, Maples PB, Senzer N, Kumar P, Wang Z, Pappen BO, Yu Y, Haddock C, Jay C, Phadke AP, Chen S, Kuhn J, Dylewski D, Scott S, Monsma D, Webb C, Tong A, Shanahan D, Nemunaitis J. Enhanced target gene knockdown by a bifunctional shRNA: a novel approach of RNA interference. Cancer Gene Ther. 2010 November; 17(11): 780-91.

15. Rao DD, Senzer N, Wang Z, Kumar P, Jay CM, Nemunaitis J. Bi-functional Short Hairpin RNA (bi-shRNA): Design and Pathway to Clinical Application. Methods Mol Biol. 2012.

What is claimed is:

1. A bifunctional shRNA composition capable of reducing expression of three or more genes, comprising:
   a first bifunctional RNA molecule that reduces the expression of a first gene target;
   a second bifunctional RNA molecule that reduces the expression of a second gene target; and
   a third bifunctional RNA molecule that reduces the expression of a third gene target, wherein each of the bifunctional RNA molecules are capable of activating a cleavage-dependent and a cleavage-independent RNA-induced silencing complex for reducing the expression level of the first, second and third gene target, wherein the bifunctional shRNAs comprises at least one nucleic acid sequence defined by SEQ ID NOS: 2, 4, 40 or 41.

2. The bifunctional shRNAs of claim 1, wherein each of the bifunctional shRNAs is spliced into a vector.

3. The bifunctional shRNAs of claim 1, wherein at least one target site for the first bifunctional RNA selectively targets a mutated KRAS gene defined further as a human KRAS gene having at least one of a G12C, a G12D, a G12V, or a G12R mutation.

4. The bifunctional shRNAs of claim 1, wherein the expression of normal RAS is not reduced below functional physiological levels by the first bifunctional RNA molecule.

5. An expression vector comprising:
   a promoter; and
   a nucleic acid insert operably linked to the promoter, wherein the insert comprises:
   a first bifunctional RNA molecule that reduces the expression of s first target gene;
   a second bifunctional RNA molecule that reduces the expression of a second target gene; and
   a third bifunctional RNA molecule that reduces the expression of a third target gene, wherein the bifunctional RNA molecule is capable of activating a cleavage-dependent and a cleavage-independent RNA-induced silencing complex for reducing the expression level of the first, second and third target genes, wherein the one or more shRNA comprise a bifunctional RNA molecule that activates a cleavage-dependent and a cleavage-independent RNA-induced silencing complex for reducing the expression level of the first, second and third target genes, wherein the bifunctional shRNAs comprises at least one nucleic acid sequence defined by SEQ ID NOS: 2, 4, 44 or 45.

6. The expression vector of claim 5, wherein at least one gene target comprises a bifunctional shRNA that selectively targets a mutated KRAS gene defined further as a human KRAS gene having at least one of a G12C, a G12D, a G12V, or a G12R mutation.

7. The expression vector of claim 5, wherein the nucleic acid insert comprises 1, 2, 3, 4, 5, 6, 7, 8, 9, 11, 10, 12, 13, 14, 15, 16, 17, 18, 20, 21, 25, 50, 75, or 100 copies of bifunctional shRNAs inserts capable of reducing an expression of one or more mutated or normal genes.

8. A therapeutic delivery system comprising:
   a therapeutic agent carrier; and
   an expression vector comprising a promoter and a nucleic acid insert operably linked to the promoter, the nucleic acid insert encoding:
   a first bifunctional RNA molecule that reduces the expression of a first gene target;
   a second bifunctional RNA molecule that reduces the expression of a second gene target; and
   a third bifunctional RNA molecule that reduces the expression of a third gene target, wherein each of the bifunctional RNA molecules are capable of activating a cleavage-dependent and a cleavage-independent RNA-induced silencing complex for reducing the expression level of the first, second and third gene target, wherein the bifunctional shRNAs comprises at least one nucleic acid sequence defined by SEQ ID NOS: 2, 4, 44 or 45.

9. The delivery system of claim 8, wherein at least one gene target comprises a bifunctional shRNA that selectively targets a mutated KRAS gene defined further as a human KRAS gene having at least one of a G12C, a G12D, a G12V, or a G12R mutation.

10. The delivery system of claim 8, wherein the nucleic acid insert comprises 1, 2, 3, 4, 5, 6, 7, 8, 9, 11, 10, 12, 13, 14, 15, 16, 17, 18, 20, 21, 25, 50, 75, or 100 copies of bifunctional shRNAs inserts capable of reducing an expression of one or more mutated or normal genes.

* * * * *

SEQUENCE LISTING

```
<160> NUMBER OF SEQ ID NOS: 126

<210> SEQ ID NO 1
<211> LENGTH: 4843
<212> TYPE: DNA
<213> ORGANISM: Artificial Sequence
<220> FEATURE:
<223> OTHER INFORMATION: Synthetic primer

<400> SEQUENCE: 1
tggccattgc atacgttgta tccatatcat aatatgtaca tttatattgg ctcatgtcca      60
acattaccgc catgttgaca ttgattattg actagttatt aatagtaatc aattacgggg     120
tcattagttc atagcccata tatggagttc cgcgttacat aacttacggt aaatggcccg     180
cctggctgac cgcccaacga cccccgccca ttgacgtcaa taatgacgta tgttcccata     240
gtaacgccaa tagggacttt ccattgacgt caatgggtgg agtatttacg gtaaactgcc     300
cacttggcag tacatcaagt gtatcatatg ccaagtacgc cccctattga cgtcaatgac     360
ggtaaatggc ccgcctggca ttatgcccag tacatgacct tatgggactt tcctacttgg     420
cagtacatct acgtattagt catcgctatt accatggtga tgcggttttg gcagtacatc     480
aatgggcgtg gatagcggtt tgactcacgg ggatttccaa gtctccaccc cattgacgtc     540
aatgggagtt tgttttggca ccaaaatcaa cgggactttc caaaatgtcg taacaactcc     600
gccccattga cgcaaatggg cggtaggcgt gtacggtggg aggtctatat aagcagagct     660
cgtttagtga accgtcagat cgcctggaga cgccatccac gctgttttga cctccataga     720
agacaccggg accgatccag cctccgcggc cgggaacggt gcattggaac gcggattccc     780
cgtgccaaga gtgacgtaag taccgcctat agactctata ggcacacccc tttggctctt     840
atgcatgcta tactgttttt ggcttggggc ctatacaccc ccgcttcctt atgctatagg     900
tgatggtata gcttagccta taggtgtggg ttattgacca ttattgacca ctccaacggt     960
ggagggcagt gtagtctgag cagtactcgt tgctgccgcg cgcgccacca gacataatag    1020
ctgacagact aacagactgt tcctttccat gggtctttc tgcagtcacc gtcgtcgaca     1080
attatctatt tcaaatttag caggaaaaaa gagaacatca ccttgtaaaa ctgaagattg    1140
tgaccagtca gaataatgtt gtggtagttg gagcttgtga tatgtgcatc tacaagctcc    1200
aactaccaca cattatggtg acagctgcct cgggaagcca agttgggctt taaagtgcag    1260
ggcctgctga tgttgagtgc ttttttgttct gtggtagcaa gagctagtag tgaagtagat    1320
tagcatctac aagctccaac taccacacat aagaagttat gtattcatcc aataattcaa    1380
gccaagcaag tatataggtg ttttaatagt ttttgtttgc agtcctctgt tggaaatgag    1440
atgacagtat agaagaatgt agtatactgt catctcattt cctggtggcc tgctatttcc    1500
ttcaaatgaa tgattttac taattttgtg tacttttatt gtgtcgatgt agaatctgcc     1560
tggtctatct gatgtgacag cttctgtagc acggaaatga tgcgacacta tgtgtttagt    1620
tatctatact gtcatctcat ttcctactgc tagctgtaga actccagctt cggcctgtcg    1680
cccaatcaaa ctgtcctgtt actgaacact gttctatggt tcacctgcgt gaagaagtgt    1740
tgtgtgatat tctgcacact tcttcacgca ggtgctgtgg tagtgaaaag tctgtagaaa    1800
agtaagggaa actcaaaccc ctttctacac cacctgcgac tagaagagtg tgtttctgta    1860
```

```
tggacacttc ttcacgcagg tgtgagtttg gtggggattg tgaccagaag attttgaaaa    1920
ttaaatatta ctgaagattt cgacttcgcg gccgcggatc cagatctttt tccctctgcc    1980
aaaaattatg gggacatcat gaagccccct gagcatctga cttctggcta ataaaggaaa    2040
tttattttca ttgcaatagt gtgttggaat tttttgtgtc tctcactcgg aaggacatat    2100
gggagggcaa atcatttaaa acatcagaat gagtatttgg tttagagttt ggcaacatat    2160
gcccattctt ccgcttcctc gctcactgac tcgctgcgct cggtcgttcg gctgcggcga    2220
gcggtatcag ctcactcaaa ggcggtaata cggttatcca gaatcaggg ataacgca    2280 ggaaagaaca tgtgagcaaa aggccagcaa aaggccagga accgtaaaaa ggccgcgttg    2340
ctggcgtttt tccataggct ccgcccccct gacgagcatc acaaaaatcg acgctcaagt    2400
cagaggtggc gaaacccgac aggactataa agataccagg cgtttccccc tggaagctcc    2460
ctcgtgcgct ctcctgttcc gaccctgccg cttaccggat acctgtccgc ctttctccct    2520
tcgggaagcg tggcgctttc tcatagctca cgctgtaggt atctcagttc ggtgtaggtc    2580
gttcgctcca agctgggctg tgtgcacgaa ccccccgttc agcccgaccg ctgcgcctta    2640
tccggtaact atcgtcttga gtccaacccg gtaagacacg acttatcgcc actggcagca    2700
gccactggta acaggattag cagagcgagg tatgtaggcg gtgctacaga gttcttgaag    2760
tggtggccta actacggcta cactagaaga acagtatttg gtatctgcgc tctgctgaag    2820
ccagttacct tcggaaaaag agttggtagc tcttgatccg gcaaacaaac caccgctggt    2880
agcggtggtt ttttgtttg caagcagcag attacgcgca gaaaaaaagg atctcaagaa    2940
gatcctttga tcttttctac ggggtctgac gctcagtgga acgaaaactc acgttaaggg    3000
attttggtca tgagattatc aaaaaggatc ttcacctaga tccttttaaa ttaaaaatga    3060
agttttaaat caatctaaag tatatatgag taaacttggt ctgacagtta ccaatgctta    3120
atcagtgagg cacctatctc agcgatctgt ctatttcgtt catccatagt tgcctgactc    3180 ggggggggg ggcgctgagg tctgcctcgt gaagaaggtg ttgctgactc ataccaggcc    3240
tgaatcgccc catcatccag ccagaaagtg agggagccac ggttgatgag agctttgttg    3300
taggtggacc agttggtgat tttgaacttt tgctttgcca cggaacggtc tgcgttgtcg    3360
ggaagatgcg tgatctgatc cttcaactca gcaaaagttc gatttattca acaaagccgc    3420
cgtcccgtca gtcagcgta atgctctgcc agtgttacaa ccaattaacc aattctgatt    3480
agaaaaactc atcgagcatc aaatgaaact gcaatttatt catatcagga ttatcaatac    3540 catattttg aaaagccgt ttctgtaatg aaggagaaaa ctcaccgagg cagttccata    3600
ggatggcaag atcctggtat cggtctgcga ttccgactcg tccaacatca atacaaccta    3660
ttaatttccc ctcgtcaaaa ataaggttat caagtgagaa atcaccatga gtgacgactg    3720
aatccggtga gaatggcaaa agcttatgca tttctttcca gacttgttca acaggccagc    3780
cattacgctc gtcatcaaaa tcactcgcat caaccaaacc gttattcatt cgtgattgcg    3840
cctgagcgag acgaaatacg cgatcgctgt taaaaggaca attacaaaca ggaatcgaat    3900
gcaaccggcg caggaacact gccagcgcat caacaatatt ttcacctgaa tcaggatatt    3960
cttctaatac ctggaatgct gttttcccgg ggatcgcagt ggtgagtaac catgcatcat    4020
caggagtacg gataaaatgc ttgatggtcg aagaggcat aaattccgtc agccagttta    4080
gtctgaccat ctcatctgta acatcattgg caacgctacc tttgccatgt ttcagaaaca    4140
actctggcgc atcgggcttc ccatacaatc gatagattgt cgcacctgat tgcccgacat    4200
```

| | |
|---|---|
| tatcgcgagc ccatttatac ccatataaat cagcatccat gttggaattt aatcgcggcc | 4260 |
| tcgagcaaga cgtttcccgt tgaatatggc tcataacacc ccttgtatta ctgtttatgt | 4320 |
| aagcagacag ttttattgtt catgatgata tattttatc ttgtgcaatg taacatcaga | 4380 |
| gattttgaga cacaacgtgg ctttcccccc cccccatta ttgaagcatt tatcagggtt | 4440 |
| attgtctcat gagcggatac atatttgaat gtatttagaa aaataaacaa ataggggttc | 4500 |
| cgcgcacatt tccccgaaaa gtgccacctg acgtctaaga aaccattatt atcatgacat | 4560 |
| taacctataa aataggcgt atcacgaggc cctttcgtct cgcgcgtttc ggtgatgacg | 4620 |
| gtgaaaacct ctgacacatg cagctcccgg agacggtcac agcttgtctg taagcggatg | 4680 |
| ccgggagcag acaagcccgt cagggcgcgt cagcgggtgt tggcgggtgt cggggctggc | 4740 |
| ttaactatgc ggcatcagag cagattgtac tgagagtgca ccatatgcgg tgtgaaatac | 4800 |
| cgcacagatg cgtaaggaga aaataccgca tcagattggc tat | 4843 |

<210> SEQ ID NO 2
<211> LENGTH: 875
<212> TYPE: DNA
<213> ORGANISM: Artificial Sequence
<220> FEATURE:
<223> OTHER INFORMATION: Synthetic primer

<400> SEQUENCE: 2

| | |
|---|---|
| tcgacaatta tctatttcaa atttagcagg aaaaaagaga acatcacctt gtaaaactga | 60 |
| agattgtgac cagtcagaat aatgttgtgg tagttggagc ttgtgatatg tgcatctaca | 120 |
| agctccaact accacacatt atggtgacag ctgcctcggg aagccaagtt gggctttaaa | 180 |
| gtgcagggcc tgctgatgtt gagtgctttt tgttctgtgg tagcaagagc tagtagtgaa | 240 |
| gtagattagc atctacaagc tccaactacc acacataaga agttatgtat tcatccaata | 300 |
| attcaagcca agcaagtata taggtgtttt aatagttttt gtttgcagtc ctctgttgga | 360 |
| aatgagatga cagtatagaa gaatgtagta tactgtcatc tcatttcctg gtggcctgct | 420 |
| atttccttca aatgaatgat ttttactaat tttgtgtact tttattgtgt cgatgtagaa | 480 |
| tctgcctggt ctatctgatg tgacagcttc tgtagcacgg aaatgatgcg acactatgtg | 540 |
| tttagttatc tatactgtca tctcatttcc tactgctagc tgtagaactc cagcttcggc | 600 |
| ctgtcgccca atcaaactgt cctgttactg aacactgttc tatggttcac ctgcgtgaag | 660 |
| aagtgttgtg tgatattctg cacacttctt cacgcaggtg ctgtggtagt gaaaagtctg | 720 |
| tagaaaagta agggaaactc aaacccctttt ctacaccacc tgcgactaga agagtgtgtt | 780 |
| tctgtatgga cacttcttca cgcaggtgtg agtttggtgg ggattgtgac cagaagattt | 840 |
| tgaaaattaa atattactga agatttcgac ttcgc | 875 |

<210> SEQ ID NO 3
<211> LENGTH: 4843
<212> TYPE: DNA
<213> ORGANISM: Artificial Sequence
<220> FEATURE:
<223> OTHER INFORMATION: Synthetic primer

<400> SEQUENCE: 3

| | |
|---|---|
| tggccattgc atacgttgta tccatatcat aatatgtaca tttatattgg ctcatgtcca | 60 |
| acattaccgc catgttgaca ttgattattg actagttatt aatagtaatc aattacgggg | 120 |
| tcattagttc atagcccata tatggagttc cgcgttacat aacttacggt aaatggcccg | 180 |
| cctggctgac cgcccaacga cccccgccca ttgacgtcaa taatgacgta tgttcccata | 240 |

```
gtaacgccaa tagggacttt ccattgacgt caatgggtgg agtatttacg gtaaactgcc    300
cacttggcag tacatcaagt gtatcatatg ccaagtacgc ccctattga cgtcaatgac     360
ggtaaatggc ccgcctggca ttatgcccag tacatgacct tatgggactt tcctacttgg    420
cagtacatct acgtattagt catcgctatt accatggtga tgcggttttg gcagtacatc    480
aatgggcgtg gatagcggtt tgactcacgg ggatttccaa gtctccaccc cattgacgtc    540
aatgggagtt tgttttggca ccaaaatcaa cgggactttc caaaatgtcg taacaactcc    600
gccccattga cgcaaatggg cggtaggcgt gtacggtggg aggtctatat aagcagagct    660
cgtttagtga accgtcagat cgcctggaga cgccatccac gctgttttga cctccataga    720
agacaccggg accgatccag cctccgcggc cgggaacggt gcattggaac gcggattccc    780
cgtgccaaga gtgacgtaag taccgcctat agactctata ggcacacccc tttggctctt    840
atgcatgcta tactgttttt ggcttgggc ctatacaccc ccgcttcctt atgctatagg     900
tgatggtata gcttagccta taggtgtggg ttattgacca ttattgacca ctccaacggt    960
ggagggcagt gtagtctgag cagtactcgt tgctgccgcg cgcgccacca gacataatag   1020
ctgacagact aacagactgt tcctttccat gggtcttttc tgcagtcacc gtcgtcgaca   1080
attatctatt tcaaatttag caggaaaaaa gagaacatca ccttgtaaaa ctgaagattg   1140
tgaccagtca gaataatgtc acctgcgtga agaagtgtga tatgtgcatc tacacttctt   1200
cacgcaggtg cattatggtg acagctgcct cgggaagcca agttgggctt taaagtgcag   1260
ggcctgctga tgttgagtgc ttttgttcc acctgcgact agaagagtag tgaagtagat    1320
tagcatctac acttcttcac gcaggtgcat aagaagttat gtattcatcc aataattcaa   1380
gccaagcaag tatataggtg ttttaatagt ttttgtttgc agtcctctgt ttgtggtagt   1440
tggagcttgt agaagaatgt agtacaagct ccaactacca catggtggcc tgctatttcc   1500
ttcaaatgaa tgattttac taattttgtg tacttttatt gtgtcgatgt agaatctgcc     1560
tggtctatct gatgtgacag cttctgtagc actgtggtag caagagctag tgtgtttagt   1620
tatctacaag ctccaactac cacatactgc tagctgtaga actccagctt cggcctgtcg   1680
cccaatcaaa ctgtcctgtt actgaacact gttctatggt tggaaatgag atgacagtat   1740
tgtgtgatat tctgcatact gtcatctcat ttccctgtgg tagtgaaaag tctgtagaaa   1800
agtaagggaa actcaaaccc ctttctacac ggaaatgatg cgacactatg tgtttctgta   1860
tggatactgt catctcattt cctgagtttg gtggggattg tgaccagaag attttgaaaa   1920
ttaaatatta ctgaagattt cgacttcgcg gccgcggatc cagatctttt tccctctgcc   1980
aaaaattatg gggacatcat gaagccccct gagcatctga cttctggcta ataaaggaaa   2040
tttattttca ttgcaatagt gtgttggaat tttttgtgtc tctcactcgg aaggacatat   2100
gggagggcaa atcatttaaa acatcagaat gagtatttgg tttagagttt ggcaacatat   2160
gcccattctt ccgcttcctc gctcactgac tcgctgcgct cggtcgttcg gctgcggcga   2220
gcggtatcag ctcactcaaa ggcggtaata cggttatcca cagaatcagg ggataacgca   2280
ggaaagaaca tgtgagcaaa aggccagcaa aaggccagga accgtaaaaa ggccgcgttg   2340
ctggcgtttt tccataggct ccgcccccct gacgagcatc acaaaaatcg acgctcaagt   2400
cagaggtggc gaaacccgac aggactataa agataccagg cgtttccccc tggaagctcc   2460
ctcgtgcgct ctcctgttcc gaccctgccg cttaccggat acctgtccgc ctttctccct   2520
tcgggaagcg tggcgctttc tcatagctca cgctgtaggt atctcagttc ggtgtaggtc   2580
```

```
gttcgctcca agctgggctg tgtgcacgaa ccccccgttc agcccgaccg ctgcgcctta    2640
tccggtaact atcgtcttga gtccaacccg gtaagacacg acttatcgcc actggcagca    2700
gccactggta acaggattag cagagcgagg tatgtaggcg gtgctacaga gttcttgaag    2760
tggtggccta actacggcta cactagaaga acagtatttg gtatctgcgc tctgctgaag    2820
ccagttacct tcggaaaaag agttggtagc tcttgatccg gcaaacaaac caccgctggt    2880
agcggtggtt ttttgtttg caagcagcag attacgcgca gaaaaaaagg atctcaagaa    2940
gatcctttga tcttttctac ggggtctgac gctcagtgga acgaaaactc acgttaaggg    3000
attttggtca tgagattatc aaaaaggatc ttcacctaga tccttttaaa ttaaaaatga    3060
agttttaaat caatctaaag tatatatgag taaacttggt ctgacagtta ccaatgctta    3120
atcagtgagg cacctatctc agcgatctgt ctatttcgtt catccatagt tgcctgactc    3180 ggggggggg ggcgctgagg tctgcctcgt gaagaaggtg ttgctgactc ataccaggcc    3240
tgaatcgccc catcatccag ccagaaagtg agggagccac ggttgatgag agctttgttg    3300
taggtggacc agttggtgat tttgaacttt tgctttgcca cggaacggtc tgcgttgtcg    3360
ggaagatgcg tgatctgatc cttcaactca gcaaaagttc gatttattca acaaagccgc    3420
cgtcccgtca gtcagcgta atgctctgcc agtgttacaa ccaattaacc aattctgatt    3480
agaaaaactc atcgagcatc aaatgaaact gcaatttatt catatcagga ttatcaatac    3540 catattttg aaaagccgt ttctgtaatg aaggagaaaa ctcaccgagg cagttccata    3600
ggatggcaag atcctggtat cggtctgcga ttccgactcg tccaacatca atacaaccta    3660
ttaatttccc ctcgtcaaaa ataaggttat caagtgagaa atcaccatga gtgacgactg    3720
aatccggtga atggcaaa agcttatgca tttctttcca gacttgttca acaggccagc    3780
cattacgctc gtcatcaaaa tcactcgcat caaccaaacc gttattcatt cgtgattgcg    3840
cctgagcgag acgaaatacg cgatcgctgt taaaaggaca attacaaaca ggaatcgaat    3900
gcaaccggcg caggaacact gccagcgcat caacaatatt ttcacctgaa tcaggatatt    3960
cttctaatac ctggaatgct gttttcccgg ggatcgcagt ggtgagtaac catgcatcat    4020
caggagtacg gataaaatgc ttgatggtcg gaagaggcat aaattccgtc agccagttta    4080
gtctgaccat ctcatctgta acatcattgg caacgctacc tttgccatgt ttcagaaaca    4140
actctggcgc atcgggcttc ccatacaatc gatagattgt cgcacctgat tgcccgacat    4200
tatcgcgagc ccatttatac ccatataaat cagcatccat gttggaattt aatcgcggcc    4260
tcgagcaaga cgtttcccgt tgaatatggc tcataacacc ccttgtatta ctgtttatgt    4320
aagcagacag ttttattgtt catgatgata tatttttatc ttgtgcaatg taacatcaga    4380
gattttgaga cacaacgtgg ctttcccccc cccccattag ttgaagcatt tatcagggtt    4440
attgtctcat gagcggatac atatttgaat gtatttagaa aaataaacaa ataggggttc    4500
cgcgcacatt tccccgaaaa gtgccacctg acgtctaaga aaccattatt atcatgacat    4560
taacctataa aaataggcgt atcacgaggc cctttcgtct cgcgcgtttc ggtgatgacg    4620
gtgaaaacct ctgacacatg cagctcccgg agacggtcac agcttgtctg taagcggatg    4680
ccgggagcag acaagcccgt cagggcgcgt cagcgggtgt tggcgggtgt cggggctggc    4740
ttaactatgc ggcatcagag cagattgtac tgagagtgca ccatatgcgg tgtgaaatac    4800
cgcacagatg cgtaaggaga aaataccgca tcagattggc tat           4843

<210> SEQ ID NO 4
<211> LENGTH: 875
```

<212> TYPE: DNA
<213> ORGANISM: Artificial Sequence
<220> FEATURE:
<223> OTHER INFORMATION: Synthetic primer

<400> SEQUENCE: 4

```
tcgacaatta tctatttcaa atttagcagg aaaaaagaga acatcacctt gtaaaactga      60
agattgtgac cagtcagaat aatgtcacct gcgtgaagaa gtgtgatatg tgcatctaca     120
cttcttcacg caggtgcatt atggtgacag ctgcctcggg aagccaagtt gggctttaaa     180
gtgcagggcc tgctgatgtt gagtgctttt tgttccacct gcgactagaa gagtagtgaa     240
gtagattagc atctcacactt cttcacgcag gtgcataaga agttatgtat tcatccaata    300
attcaagcca agcaagtata taggtgtttt aatagttttt gtttgcagtc ctctgtttgt     360
ggtagttgga gcttgtagaa gaatgtagta caagctccaa ctaccacatg gtggcctgct     420
atttccttca aatgaatgat ttttactaat tttgtgtact tttattgtgt cgatgtagaa     480
tctgcctggt ctatctgatg tgacagcttc tgtagcactg tggtagcaag agctagtgtg     540
tttagttatc tacaagctcc aactaccaca tactgctagc tgtagaactc cagcttcggc     600
ctgtcgccca atcaaactgt cctgttactg aacactgttc tatggttgga aatgagatga    660
cagtattgtg tgatattctg catactgtca tctcatttcc ctgtggtagt gaaaagtctg     720
tagaaaagta agggaaactc aaaccccttt ctacacggaa atgatgcgac actatgtgtt     780
tctgtatgga tactgtcatc tcatttcctg agtttggtgg ggattgtgac cagaagatt     840
tgaaaattaa atattactga agatttcgac ttcgc                                875
```

<210> SEQ ID NO 5
<211> LENGTH: 245
<212> TYPE: DNA
<213> ORGANISM: Artificial Sequence
<220> FEATURE:
<223> OTHER INFORMATION: Synthetic primer

<400> SEQUENCE: 5

```
tcgactgctg ttgaagtgag cgcctgtggt agttggagct gattagtgaa gccacagatg      60
taatcagctc caactaccac agttgcctac tgcctcggaa gcagctcact acattactca     120
gctgttgaag tgagcgcctg tggtaggaag agatgattag tgaagccaca gatgtaatca     180
gctccaacta ccacagttgc ctactgcctc ggaagcttaa taaggatct tttattttca      240
ttggc                                                                  245
```

<210> SEQ ID NO 6
<211> LENGTH: 245
<212> TYPE: DNA
<213> ORGANISM: Artificial Sequence
<220> FEATURE:
<223> OTHER INFORMATION: Synthetic primer

<400> SEQUENCE: 6

```
tcgactgctg ttgaagtgag cgccgtggta gttggagctg atgtagtgaa gccacagatg      60
tacatcagct ccaactacca cgttgcctac tgcctcggaa gcagctcact acattactca     120
gctgttgaag tgagcgccgt ggtagtctta gctaatgtag tgaagccaca gatgtacatc     180
agctccaact accacgttgc ctactgcctc ggaagcttaa taaggatct tttattttca      240
ttggc                                                                  245
```

<210> SEQ ID NO 7

```
<211> LENGTH: 245
<212> TYPE: DNA
<213> ORGANISM: Artificial Sequence
<220> FEATURE:
<223> OTHER INFORMATION: Synthetic primer

<400> SEQUENCE: 7
tcgactgctg ttgaagtgag cgcctggtag ttggagctga tggtagtgaa gccacagatg      60
taccatcagc tccaactacc agttgcctac tgcctcggaa gcagctcact acattactca     120
gctgttgaag tgagcgcctg gtagttactg ctaatggtag tgaagccaca gatgtaccat     180
cagctccaac taccagttgc ctactgcctc ggaagcttaa taaaggatct tttattttca     240
ttggc                                                                 245

<210> SEQ ID NO 8
<211> LENGTH: 245
<212> TYPE: DNA
<213> ORGANISM: Artificial Sequence
<220> FEATURE:
<223> OTHER INFORMATION: Synthetic primer

<400> SEQUENCE: 8
tcgactgctg ttgaagtgag cgccggtagt tggagctgat ggctagtgaa gccacagatg      60
tagccatcag ctccaactac cgttgcctac tgcctcggaa gcagctcact acattactca     120
gctgttgaag tgagcgccgg tagttgtctc tgatagctag tgaagccaca gatgtagcca     180
tcagctccaa ctaccgttgc ctactgcctc ggaagcttaa taaaggatct tttattttca     240
ttggc                                                                 245

<210> SEQ ID NO 9
<211> LENGTH: 245
<212> TYPE: DNA
<213> ORGANISM: Artificial Sequence
<220> FEATURE:
<223> OTHER INFORMATION: Synthetic primer

<400> SEQUENCE: 9
tcgactgctg ttgaagtgag cgccgtagtt ggagctgatg gcgtagtgaa gccacagatg      60
tacgccatca gctccaacta cgttgcctac tgcctcggaa gcagctcact acattactca     120
gctgttgaag tgagcgccgt agttggagct gatggcgtag tgaagccaca gatgtacgcc     180
atcagctcca actacgttgc ctactgcctc ggaagcttaa taaaggatct tttattttca     240
ttggc                                                                 245

<210> SEQ ID NO 10
<211> LENGTH: 245
<212> TYPE: DNA
<213> ORGANISM: Artificial Sequence
<220> FEATURE:
<223> OTHER INFORMATION: Synthetic primer

<400> SEQUENCE: 10
tcgactgctg ttgaagtgag cgcctagttg gagctgatgg cgttagtgaa gccacagatg      60
taacgccatc agctccaact agttgcctac tgcctcggaa gcagctcact acattactca     120
gctgttgaag tgagcgccta gttggatgag atgacgttag tgaagccaca gatgtaacgc     180
catcagctcc aactagttgc ctactgcctc ggaagcttaa taaaggatct tttattttca     240
ttggc                                                                 245
```

<210> SEQ ID NO 11
<211> LENGTH: 245
<212> TYPE: DNA
<213> ORGANISM: Artificial Sequence
<220> FEATURE:
<223> OTHER INFORMATION: Synthetic primer

<400> SEQUENCE: 11

```
tcgactgctg ttgaagtgag cgccagttgg agctgatggc gtatagtgaa gccacagatg    60
tatacgccat cagctccaac tgttgcctac tgcctcggaa gcagctcact acattactca   120
gctgttgaag tgagcgccag ttggagacta tggagtatag tgaagccaca gatgtatacg   180
ccatcagctc caactgttgc ctactgcctc ggaagcttaa taaggatct tttatttttca   240
ttggc                                                                245
```

<210> SEQ ID NO 12
<211> LENGTH: 245
<212> TYPE: DNA
<213> ORGANISM: Artificial Sequence
<220> FEATURE:
<223> OTHER INFORMATION: Synthetic primer

<400> SEQUENCE: 12

```
tcgactgctg ttgaagtgag cgccgttgga gctgatggcg tagtagtgaa gccacagatg    60
tactacgcca tcagctccaa cgttgcctac tgcctcggaa gcagctcact acattactca   120
gctgttgaag tgagcgccgt tgaagcacgt ggtgtagtag tgaagccaca gatgtactac   180
gccatcagct ccaacgttgc ctactgcctc ggaagcttaa taaggatct tttatttttca   240
ttggc                                                                245
```

<210> SEQ ID NO 13
<211> LENGTH: 245
<212> TYPE: DNA
<213> ORGANISM: Artificial Sequence
<220> FEATURE:
<223> OTHER INFORMATION: Synthetic primer

<400> SEQUENCE: 13

```
tcgactgctg ttgaagtgag cgccttggag ctgatggcgt aggtagtgaa gccacagatg    60
tacctacgcc atcagctcca agttgcctac tgcctcggaa gcagctcact acattactca   120
gctgttgaag tgagcgcctt ggagctatag gtctaggtag tgaagccaca gatgtaccta   180
cgccatcagc tccaagttgc ctactgcctc ggaagcttaa taaggatct tttatttttca   240
ttggc                                                                245
```

<210> SEQ ID NO 14
<211> LENGTH: 245
<212> TYPE: DNA
<213> ORGANISM: Artificial Sequence
<220> FEATURE:
<223> OTHER INFORMATION: Synthetic primer

<400> SEQUENCE: 14

```
tcgactgctg ttgaagtgag cgcctggagc tgatggcgta ggctagtgaa gccacagatg    60
tagcctacgc catcagctcc agttgcctac tgcctcggaa gcagctcact acattactca   120
gctgttgaag tgagcgcctg gagctgtatg cgttcgctag tgaagccaca gatgtagcct   180
acgccatcag ctccagttgc ctactgcctc ggaagcttaa taaggatct tttatttttca   240
ttggc                                                                245
```

<210> SEQ ID NO 15
<211> LENGTH: 245
<212> TYPE: DNA
<213> ORGANISM: Artificial Sequence
<220> FEATURE:
<223> OTHER INFORMATION: Synthetic primer

<400> SEQUENCE: 15
tcgactgctg ttgaagtgag cgccgttgga gctgatggcg tagtagtgaa gccacagatg      60
tactatgcca tcagctccaa cgttgcctac tgcctcggaa gcagctcact acattactca     120
gctgttgaag tgagcgccgt tgaagcacgt ggtgtagtag tgaagccaca gatgtactat     180
gccatcagct ccaacgttgc ctactgcctc ggaagcttaa taaggatctt tttatttttca    240 ttggc                                                                 245

<210> SEQ ID NO 16
<211> LENGTH: 245
<212> TYPE: DNA
<213> ORGANISM: Artificial Sequence
<220> FEATURE:
<223> OTHER INFORMATION: Synthetic primer

<400> SEQUENCE: 16
tcgactgctg ttgaagtgag cgccttggag ctgatggcgt aggtagtgaa gccacagatg      60
tacctatgcc atcagctcca agttgcctac tgcctcggaa gcagctcact acattactca     120
gctgttgaag tgagcgcctt ggagctatag gtctaggtag tgaagccaca gatgtaccta     180
tgccatcagc tccaagttgc ctactgcctc ggaagcttaa taaggatctt tttatttttca    240 ttggc                                                                 245

<210> SEQ ID NO 17
<211> LENGTH: 245
<212> TYPE: DNA
<213> ORGANISM: Artificial Sequence
<220> FEATURE:
<223> OTHER INFORMATION: Synthetic primer

<400> SEQUENCE: 17
tcgactgctg ttgaagtgag cgcctggagc tgatggcgta ggctagtgaa gccacagatg      60
tagcctatgc catcagctcc agttgcctac tgcctcggaa gcagctcact acattactca     120
gctgttgaag tgagcgcctg gagctgtatg cgttcgctag tgaagccaca gatgtagcct     180
atgccatcag ctccagttgc ctactgcctc ggaagcttaa taaggatctt tttatttttca    240 ttggc                                                                 245

<210> SEQ ID NO 18
<211> LENGTH: 245
<212> TYPE: DNA
<213> ORGANISM: Artificial Sequence
<220> FEATURE:
<223> OTHER INFORMATION: Synthetic primer

<400> SEQUENCE: 18
tcgactgctg ttgaagtgag cgccgttgga gctcatggcg tagtagtgaa gccacagatg      60
tactacgcca tgagctccaa cgttgcctac tgcctcggaa gcagctcact acattactca     120
gctgttgaag tgagcgccgt tgaagcacgt ggtgtagtag tgaagccaca gatgtactac     180
gccatgagct ccaacgttgc ctactgcctc ggaagcttaa taaggatctt tttatttttca    240 ttggc                                                                 245

<210> SEQ ID NO 19
<211> LENGTH: 245
<212> TYPE: DNA
<213> ORGANISM: Artificial Sequence
<220> FEATURE:
<223> OTHER INFORMATION: Synthetic primer

<400> SEQUENCE: 19
tcgactgctg ttgaagtgag cgccttggag ctcatggcgt aggtagtgaa gccacagatg    60
tacctacgcc atgagctcca agttgcctac tgcctcggaa gcagctcact acattactca   120
gctgttgaag tgagcgcctt ggagctatag gtctaggtag tgaagccaca gatgtaccta   180
cgccatgagc tccaagttgc ctactgcctc ggaagcttaa taaggatct tttattttca   240 ttggc                                                                245

<210> SEQ ID NO 20
<211> LENGTH: 245
<212> TYPE: DNA
<213> ORGANISM: Artificial Sequence
<220> FEATURE:
<223> OTHER INFORMATION: Synthetic primer

<400> SEQUENCE: 20
tcgactgctg ttgaagtgag cgcctggagc tcatggcgta ggctagtgaa gccacagatg    60
tagcctacgc catgagctcc agttgcctac tgcctcggaa gcagctcact acattactca   120
gctgttgaag tgagcgcctg agctgtatg cgttcgctag tgaagccaca gatgtagcct   180
acgccatgag ctccagttgc ctactgcctc ggaagcttaa taaggatct tttattttca   240 ttggc                                                                245

<210> SEQ ID NO 21
<211> LENGTH: 245
<212> TYPE: DNA
<213> ORGANISM: Artificial Sequence
<220> FEATURE:
<223> OTHER INFORMATION: Synthetic primer

<400> SEQUENCE: 21
tcgactgctg ttgaagtgag cgccgtggta gttggagctg ttgtagtgaa gccacagatg    60
tacaacagct ccaactacca cgttgcctac tgcctcggaa gcagctcact acattactca   120
gctgttgaag tgagcgccgt ggtagtctta gctattgtag tgaagccaca gatgtacaac   180
agctccaact accacgttgc ctactgcctc ggaagcttaa taaggatct tttattttca   240 ttggc                                                                245

<210> SEQ ID NO 22
<211> LENGTH: 245
<212> TYPE: DNA
<213> ORGANISM: Artificial Sequence
<220> FEATURE:
<223> OTHER INFORMATION: Synthetic primer

<400> SEQUENCE: 22
tcgactgctg ttgaagtgag cgcctggtag ttggagctgt tggtagtgaa gccacagatg    60
taccaacagc tccaactacc agttgcctac tgcctcggaa gcagctcact acattactca   120
gctgttgaag tgagcgcctg gtagttactg ctattggtag tgaagccaca gatgtaccaa   180
cagctccaac taccagttgc ctactgcctc ggaagcttaa taaggatct tttattttca   240

```
ttggc                                                                   245

<210> SEQ ID NO 23
<211> LENGTH: 245
<212> TYPE: DNA
<213> ORGANISM: Artificial Sequence
<220> FEATURE:
<223> OTHER INFORMATION: Synthetic primer

<400> SEQUENCE: 23
tcgactgctg ttgaagtgag cgcctgtggt agttggagct cgttagtgaa gccacagatg      60
taacgagctc caactaccac agttgcctac tgcctcggaa gcagctcact acattactca     120
gctgttgaag tgagcgcctg tggtagactg agctagttag tgaagccaca gatgtaacga     180
gctccaacta ccacagttgc ctactgcctc ggaagcttaa taaggatctc tttatttttca    240 ttggc                                                                   245

<210> SEQ ID NO 24
<211> LENGTH: 245
<212> TYPE: DNA
<213> ORGANISM: Artificial Sequence
<220> FEATURE:
<223> OTHER INFORMATION: Synthetic primer

<400> SEQUENCE: 24
tcgactgctg ttgaagtgag cgccgtggta gttggagctc gtgtagtgaa gccacagatg      60
tacacgagct ccaactacca cgttgcctac tgcctcggaa gcagctcact acattactca     120
gctgttgaag tgagcgccgt ggtagtacta gctagtgtag tgaagccaca gatgtacacg     180
agctccaact accacgttgc ctactgcctc ggaagcttaa taaggatctt tttatttttca    240 ttggc                                                                   245

<210> SEQ ID NO 25
<211> LENGTH: 245
<212> TYPE: DNA
<213> ORGANISM: Artificial Sequence
<220> FEATURE:
<223> OTHER INFORMATION: Synthetic primer

<400> SEQUENCE: 25
tcgactgctg ttgaagtgag cgcctgtggt agttggagct tgttagtgaa gccacagatg      60
taacaagctc caactaccac agttgcctac tgcctcggaa gcagctcact acattactca     120
gctgttgaag tgagcgcctg tggtagactg agctagttag tgaagccaca gatgtaacaa     180
gctccaacta ccacagttgc ctactgcctc ggaagcttaa taaggatctt tttatttttca    240 ttggc                                                                   245

<210> SEQ ID NO 26
<211> LENGTH: 245
<212> TYPE: DNA
<213> ORGANISM: Artificial Sequence
<220> FEATURE:
<223> OTHER INFORMATION: Synthetic primer

<400> SEQUENCE: 26
tcgactgctg ttgaagtgag cgccgtggta gttggagctt gtgtagtgaa gccacagatg      60
tacacaagct ccaactacca cgttgcctac tgcctcggaa gcagctcact acattactca     120
gctgttgaag tgagcgccgt ggtagtctta gcttatgtag tgaagccaca gatgtacaca     180
agctccaact accacgttgc ctactgcctc ggaagcttaa taaggatctt tttatttttca    240
```

-continued

```
ttggc                                                                   245

<210> SEQ ID NO 27
<211> LENGTH: 245
<212> TYPE: DNA
<213> ORGANISM: Artificial Sequence
<220> FEATURE:
<223> OTHER INFORMATION: Synthetic primer

<400> SEQUENCE: 27
tcgactgctg ttgaagtgag cgccgttgtc aatatagata caatagtgaa gccacagatg       60
tattgtatct atattgacaa cgttgcctac tgcctcggaa gcagctcact acattactca      120
gctgttgaag tgagcgccgt tgtcaatgct gatccaatag tgaagccaca gatgtattgt      180
atctatattg acaacgttgc ctactgcctc ggaagcttaa taaggatct tttattttca       240 ttggc                                                                   245

<210> SEQ ID NO 28
<211> LENGTH: 245
<212> TYPE: DNA
<213> ORGANISM: Artificial Sequence
<220> FEATURE:
<223> OTHER INFORMATION: Synthetic primer

<400> SEQUENCE: 28
tcgactgctg ttgaagtgag cgccaaagca aactcttccg aaatagtgaa gccacagatg       60
tatttcggaa gagtttgctt tgttgcctac tgcctcggaa gcagctcact acattactca      120
gctgttgaag tgagcgccaa agcaaatact tctgaaatag tgaagccaca gatgtatttc      180
ggaagagttt gctttgttgc ctactgcctc ggaagcttaa taaggatct tttattttca       240 ttggc                                                                   245

<210> SEQ ID NO 29
<211> LENGTH: 245
<212> TYPE: DNA
<213> ORGANISM: Artificial Sequence
<220> FEATURE:
<223> OTHER INFORMATION: Synthetic primer

<400> SEQUENCE: 29
tcgactgctg ttgaagtgag cgccgttgtc aatatagata caatagtgaa gccacagatg       60
tattgtatct atattgacaa cgttgcctac tgcctcggaa gcagctcact acattactca      120
gctgttgaag tgagcgccga ggaagagaga ggtaagttag tgaagccaca gatgtaactg      180
acctggttct cctcgttgc ctactgcctc ggaagcttaa taaggatct tttattttca        240 ttggc                                                                   245

<210> SEQ ID NO 30
<211> LENGTH: 245
<212> TYPE: DNA
<213> ORGANISM: Artificial Sequence
<220> FEATURE:
<223> OTHER INFORMATION: Synthetic primer

<400> SEQUENCE: 30
tcgactgctg ttgaagtgag cgccaaagca aactcttccg aaatagtgaa gccacagatg       60
tatttcggaa gagtttgctt tgttgcctac tgcctcggaa gcagctcact acattactca      120
gctgttgaag tgagcgccga ggaagagaga ggtaagttag tgaagccaca gatgtaactg      180
```

```
acctggttct tcctcgttgc ctactgcctc ggaagcttaa taaaggatct tttattttca    240
ttggc                                                                245

<210> SEQ ID NO 31
<211> LENGTH: 245
<212> TYPE: DNA
<213> ORGANISM: Artificial Sequence
<220> FEATURE:
<223> OTHER INFORMATION: Synthetic primer

<400> SEQUENCE: 31
tcgactgctg ttgaagtgag cgcccctata tggtagagca atatagtgaa gccacagatg     60
tatattgctc taccatatag ggttgcctac tgcctcggaa gcagctcact acattactca    120
gctgttgaag tgagcgcccc tatatgcatg atcaatatag tgaagccaca gatgtatatt    180
gctctaccat atagggttgc ctactgcctc ggaagcttaa taaaggatct tttattttca    240
ttggc                                                                245

<210> SEQ ID NO 32
<211> LENGTH: 245
<212> TYPE: DNA
<213> ORGANISM: Artificial Sequence
<220> FEATURE:
<223> OTHER INFORMATION: Synthetic primer

<400> SEQUENCE: 32
tcgactgctg ttgaagtgag cgccggaaat gagatgacag tattagtgaa gccacagatg     60
taatactgtc atctcatttc cgttgcctac tgcctcggaa gcagctcact acattactca    120
gctgttgaag tgagcgccgg aaatgactag acactattag tgaagccaca gatgtaatac    180
tgtcatctca tttccgttgc ctactgcctc ggaagcttaa taaaggatct tttattttca    240
ttggc                                                                245

<210> SEQ ID NO 33
<211> LENGTH: 245
<212> TYPE: DNA
<213> ORGANISM: Artificial Sequence
<220> FEATURE:
<223> OTHER INFORMATION: Synthetic primer

<400> SEQUENCE: 33
tcgactgctg ttgaagtgag cgccatggaa ggtacaggaa tattagtgaa gccacagatg     60
taatattcct gtaccttcca tgttgcctac tgcctcggaa gcagctcact acattactca    120
gctgttgaag tgagcgccat ggaaggacta gtaatattag tgaagccaca gatgtaatat    180
tcctgtacct tccatgttgc ctactgcctc ggaagcttaa taaaggatct tttattttca    240
ttggc                                                                245

<210> SEQ ID NO 34
<211> LENGTH: 245
<212> TYPE: DNA
<213> ORGANISM: Artificial Sequence
<220> FEATURE:
<223> OTHER INFORMATION: Synthetic primer

<400> SEQUENCE: 34
tcgactgctg ttgaagtgag cgcctcatgg gaattcatat cattagtgaa gccacagatg     60
taatgatatg aattcccatg agttgcctac tgcctcggaa gcagctcact acattactca    120
gctgttgaag tgagcgcctc atgggacaac atctcattag tgaagccaca gatgtaatga    180
```

```
tatgaattcc catgagttgc ctactgcctc ggaagcttaa taaaggatct tttattttca      240
ttggc                                                                  245

<210> SEQ ID NO 35
<211> LENGTH: 245
<212> TYPE: DNA
<213> ORGANISM: Artificial Sequence
<220> FEATURE:
<223> OTHER INFORMATION: Synthetic primer

<400> SEQUENCE: 35
tcgactgctg ttgaagtgag cgccccacca atcagaaaca gtatagtgaa gccacagatg       60
tatactgttt ctgattggtg ggttgcctac tgcctcggaa gcagctcact acattactca      120
gctgttgaag tgagcgcccc accaatgtca aatagtatag tgaagccaca gatgtatact      180
gtttctgatt ggtgggttgc ctactgcctc ggaagcttaa taaaggatct tttattttca      240
ttggc                                                                  245

<210> SEQ ID NO 36
<211> LENGTH: 245
<212> TYPE: DNA
<213> ORGANISM: Artificial Sequence
<220> FEATURE:
<223> OTHER INFORMATION: Synthetic primer

<400> SEQUENCE: 36
tcgactgctg ttgaagtgag cgccggagga gattgataga gcctagtgaa gccacagatg       60
taggctctat caatctcctc cgttgcctac tgcctcggaa gcagctcact acattactca      120
gctgttgaag tgagcgccgg aggagacata tacagcctag tgaagccaca gatgtaggct      180
ctatcaatct cctccgttgc ctactgcctc ggaagcttaa taaaggatct tttattttca      240
ttggc                                                                  245

<210> SEQ ID NO 37
<211> LENGTH: 49
<212> TYPE: DNA
<213> ORGANISM: Artificial Sequence
<220> FEATURE:
<223> OTHER INFORMATION: Synthetic primer

<400> SEQUENCE: 37
aaagcaattt ctacacgaga tcctctctct gaaatcacta agcaggaga                   49

<210> SEQ ID NO 38
<211> LENGTH: 19
<212> TYPE: DNA
<213> ORGANISM: Artificial Sequence
<220> FEATURE:
<223> OTHER INFORMATION: Synthetic primer

<400> SEQUENCE: 38
tctctctgaa atcactaag                                                    19

<210> SEQ ID NO 39
<211> LENGTH: 19
<212> TYPE: DNA
<213> ORGANISM: Artificial Sequence
<220> FEATURE:
<223> OTHER INFORMATION: Synthetic primer

<400> SEQUENCE: 39
```

```
cttagtgatt tcagagaga                                                    19

<210> SEQ ID NO 40
<211> LENGTH: 19
<212> TYPE: DNA
<213> ORGANISM: Artificial Sequence
<220> FEATURE:
<223> OTHER INFORMATION: Synthetic primer

<400> SEQUENCE: 40
ggaaatgaga tgacagtat                                                    19

<210> SEQ ID NO 41
<211> LENGTH: 19
<212> TYPE: DNA
<213> ORGANISM: Artificial Sequence
<220> FEATURE:
<223> OTHER INFORMATION: Synthetic primer

<400> SEQUENCE: 41
atactgtcat ctcatttcc                                                    19

<210> SEQ ID NO 42
<211> LENGTH: 19
<212> TYPE: DNA
<213> ORGANISM: Artificial Sequence
<220> FEATURE:
<223> OTHER INFORMATION: Synthetic primer

<400> SEQUENCE: 42
ccagtgcacc attgataaa                                                    19

<210> SEQ ID NO 43
<211> LENGTH: 19
<212> TYPE: DNA
<213> ORGANISM: Artificial Sequence
<220> FEATURE:
<223> OTHER INFORMATION: Synthetic primer

<400> SEQUENCE: 43
tttatcaatg gtgcactgg                                                    19

<210> SEQ ID NO 44
<211> LENGTH: 868
<212> TYPE: DNA
<213> ORGANISM: Artificial Sequence
<220> FEATURE:
<223> OTHER INFORMATION: Synthetic primer

<400> SEQUENCE: 44
aattatctat ttcaaattta gcaggaaaaa agagaacatc accttgtaaa actgaagatt        60
gtgaccagtc agaataatgt tctctctgaa atcactaagg atatgtgcat ctcttagtga       120
tttcagagag acattatggt gacagctgcc tcgggaagcc aagttgggct ttaaagtgca       180
gggcctgctg atgttgagtg cttttttgttc tctctctgct gtcacttaga gtgaagtaga      240
ttagcatctc ttagtgattt cagagagaca taagaagtta tgtattcatc caataattca       300
agccaagcaa gtatataggt gttttaatag tttttgtttg cagtcctctg ttggaaatga       360
tgcgacacta tagaagaatg tagtatactg tcatctcatt tcctggtggc ctgctatttc       420
cttcaaatga atgattttta ctaatttttgt gtacttttat tgtgtcgatg tagaatctgc      480
ctggtctatc tgatgtgaca gcttctgtag cacggaaatg agatgacagt atgtgtttag       540
ttatctatac tgtcatctca tttcctactg ctagctgtag aactccagct tcggcctgtc       600
```

| | | |
|---|---|---|
| gcccaatcaa actgtcctgt tactgaacac tgttctatgg ttccagtgca ccattgataa | 660 | |
| atgtgtgata ttctgcttta tcaatggtgc actggctgtg gtagtgaaaa gtctgtagaa | 720 | |
| aagtaaggga aactcaaacc cctttctaca cccagtgcat gcttgataaa gtgtttctgt | 780 | |
| atggtttatc aatggtgcac tggtgagttt ggtggggatt gtgaccagaa gattttgaaa | 840 | |
| attaaatatt actgaagatt tcgacttc | 868 | |

<210> SEQ ID NO 45
<211> LENGTH: 868
<212> TYPE: DNA
<213> ORGANISM: Artificial Sequence
<220> FEATURE:
<223> OTHER INFORMATION: Synthetic primer

<400> SEQUENCE: 45

| | | |
|---|---|---|
| aattatctat ttcaaattta gcaggaaaaa agagaacatc accttgtaaa actgaagatt | 60 | |
| gtgaccagtc agaataatgt ggaaatgatg cgacactatg atatgtgcat ctatactgtc | 120 | |
| atctcatttc ccattatggt gacagctgcc tcgggaagcc aagttgggct ttaaagtgca | 180 | |
| gggcctgctg atgttgagtg cttttttgttc ggaaatgaga tgacagtata gtgaagtaga | 240 | |
| ttagcatcta tactgtcatc tcatttccca taagaagtta tgtattcatc caataattca | 300 | |
| agccaagcaa gtatataggt gttttaatag ttttttgtttg cagtcctctg ttccagtgca | 360 | |
| ccattgataa aagaagaatg tagttttatc aatggtgcac tggtggtggc ctgctatttc | 420 | |
| cttcaaatga atgattttta ctaattttgt gtacttttat tgtgtcgatg tagaatctgc | 480 | |
| ctggtctatc tgatgtgaca gcttctgtag cacccagtgc atgcttgata aagtgtttag | 540 | |
| ttatcttttta tcaatggtgc actggtactg ctagctgtag aactccagct tcggcctgtc | 600 | |
| gcccaatcaa actgtcctgt tactgaacac tgttctatgg tttctctctg aaatcactaa | 660 | |
| gtgtgtgata ttctgcctta gtgatttcag agagactgtg gtagtgaaaa gtctgtagaa | 720 | |
| aagtaaggga aactcaaacc cctttctaca ctctctctgc tgtcacttag gtgtttctgt | 780 | |
| atggcttagt gatttcagag agatgagttt ggtggggatt gtgaccagaa gattttgaaa | 840 | |
| attaaatatt actgaagatt tcgacttc | 868 | |

<210> SEQ ID NO 46
<211> LENGTH: 4843
<212> TYPE: DNA
<213> ORGANISM: Artificial Sequence
<220> FEATURE:
<223> OTHER INFORMATION: Synthetic primer

<400> SEQUENCE: 46

| | | |
|---|---|---|
| tggccattgc atacgttgta tccatatcat aatatgtaca tttatattgg ctcatgtcca | 60 | |
| acattaccgc catgttgaca ttgattattg actagttatt aatagtaatc aattacgggg | 120 | |
| tcattagttc atagcccata tatggagttc cgcgttacat aacttacggt aaatggcccg | 180 | |
| cctggctgac cgcccaacga ccccgcccca ttgacgtcaa taatgacgta tgttcccata | 240 | |
| gtaacgccaa tagggacttt ccattgacgt caatgggtgg agtatttacg gtaaactgcc | 300 | |
| cacttggcag tacatcaagt gtatcatatg ccaagtacgc ccctattga cgtcaatgac | 360 | |
| ggtaaatggc ccgcctggca ttatgcccag tacatgacct tatgggactt tcctacttgg | 420 | |
| cagtacatct acgtattagt catcgctatt accatggtga tgcggttttg gcagtacatc | 480 | |
| aatgggcgtg gatagcggtt tgactcacgg ggatttccaa gtctccaccc cattgacgtc | 540 | |

-continued

```
aatgggagtt tgttttggca ccaaaatcaa cgggactttc caaaatgtcg taacaactcc    600
gccccattga cgcaaatggg cggtaggcgt gtacggtggg aggtctatat aagcagagct    660
cgtttagtga accgtcagat cgcctggaga cgccatccac gctgttttga cctccataga    720
agacaccggg accgatccag cctccgcggc cgggaacggt gcattggaac gcggattccc    780
cgtgccaaga gtgacgtaag taccgcctat agactctata ggcacacccc tttggctctt    840
atgcatgcta tactgttttt ggcttggggc ctatacaccc ccgcttcctt atgctatagg    900
tgatggtata gcttagccta taggtgtggg ttattgacca ttattgacca ctccaacggt    960
ggagggcagt gtagtctgag cagtactcgt tgctgccgcg cgcgccacca gacataatag   1020
ctgacagact aacagactgt tccttttccat gggtctttttc tgcagtcacc gtcgtcgaca   1080
attatctatt tcaaatttag caggaaaaaa gagaacatca ccttgtaaaa ctgaagattg   1140
tgaccagtca gaataatgtt ctctctgaaa tcactaagga tatgtgcatc tcttagtgat   1200
ttcagagaga cattatggtg acagctgcct cgggaagcca agttgggctt taaagtgcag   1260
ggcctgctga tgttgagtgc ttttgttct ctctctgctg tcacttagag tgaagtagat   1320
tagcatctct tagtgatttc agagagacat aagaagttat gtattcatcc aataattcaa   1380
gccaagcaag tatataggtg ttttaatagt ttttgtttgc agtcctctgt tggaaatgat   1440
gcgacactat agaagaatgt agtatactgt catctcattt cctggtggcc tgctatttcc   1500
ttcaaatgaa tgattttac taattttgtg tactttatt gtgtcgatgt agaatctgcc   1560
tggtctatct gatgtgacag cttctgtagc acggaaatga gatgacagta tgtgtttagt   1620
tatctatact gtcatctcat ttcctactgc tagctgtaga actccagctt cggcctgtcg   1680
cccaatcaaa ctgtcctgtt actgaacact gttctatggt tccagtgcac cattgataaa   1740
tgtgtgatat tctgctttat caatggtgca ctggctgtgg tagtgaaaag tctgtagaaa   1800
agtaagggaa actcaaaccc ctttctacac ccagtgcatg cttgataaag tgtttctgta   1860
tggtttatca atggtgcact ggtgagtttg gtggggattg tgaccagaag attttgaaaa   1920
ttaaatatta ctgaagattt cgacttcgcg gccgcggatc cagatctttt tccctctgcc   1980
aaaaattatg gggacatcat gaagccccctt gagcatctga cttctggcta ataaaggaaa   2040
tttattttca ttgcaatagt gtgttggaat ttttttgtgtc tctcactcgg aaggacatat   2100
gggagggcaa atcatttaaa acatcagaat gagtatttgg tttagagttt ggcaacatat   2160
gcccattctt ccgcttcctc gctcactgac tcgctgcgct cggtcgttcg gctgcggcga   2220
gcggtatcag ctcactcaaa ggcggtaata cggttatcca cagaatcagg ggataacgca   2280
ggaaagaaca tgtgagcaaa aggccagcaa aaggccagga accgtaaaaa ggccgcgttg   2340
ctggcgtttt tccataggct ccgcccccct gacgagcatc acaaaaatcg acgctcaagt   2400
cagaggtggc gaaacccgac aggactataa agataccagg cgtttccccc tggaagctcc   2460
ctcgtgcgct ctcctgttcc gaccctgccg cttaccggat acctgtccgc ctttctccct   2520
tcgggaagcg tggcgctttc tcatagctca cgctgtaggt atctcagttc ggtgtaggtc   2580
gttcgctcca agctgggctg tgtgcacgaa ccccccgttc agcccgaccg ctgcgcctta   2640
tccggtaact atcgtcttga gtccaacccg gtaagcacg acttatcgcc actggcagca   2700
gccactggta acaggattag cagagcgagg tatgtaggcg gtgctacaga gttcttgaag   2760
tggtggccta actacggcta cactagaaga acagtatttg gtatctgcgc tctgctgaag   2820
ccagttacct tcggaaaaag agttggtagc tcttgatccg gcaaacaaac caccgctggt   2880
agcggtggtt tttttgtttg caagcagcag attacgcgca gaaaaaaagg atctcaagaa   2940
```

```
gatcctttga tcttttctac ggggtctgac gctcagtgga acgaaaactc acgttaaggg    3000
attttggtca tgagattatc aaaaaggatc ttcacctaga tccttttaaa ttaaaaatga    3060
agttttaaat caatctaaag tatatatgag taaacttggt ctgacagtta ccaatgctta    3120
atcagtgagg cacctatctc agcgatctgt ctatttcgtt catccatagt tgcctgactc    3180 ggggggggggg ggcgctgagg tctgcctcgt gaagaaggtg ttgctgactc ataccaggcc    3240
tgaatcgccc catcatccag ccagaaagtg agggagccac ggttgatgag agctttgttg    3300
taggtggacc agttggtgat tttgaacttt tgctttgcca cggaacggtc tgcgttgtcg    3360
ggaagatgcg tgatctgatc cttcaactca gcaaaagttc gatttattca acaaagccgc    3420
cgtcccgtca agtcagcgta atgctctgcc agtgttacaa ccaattaacc aattctgatt    3480
agaaaaactc atcgagcatc aaatgaaact gcaatttatt catatcagga ttatcaatac    3540 catattttg aaaaagccgt ttctgtaatg aaggagaaaa ctcaccgagg cagttccata    3600
ggatggcaag atcctggtat cggtctgcga ttccgactcg tccaacatca atacaaccta    3660
ttaatttccc ctcgtcaaaa ataaggttat caagtgagaa atcaccatga gtgacgactg    3720
aatccggtga gaatggcaaa agcttatgca tttctttcca gacttgttca acaggccagc    3780
cattacgctc gtcatcaaaa tcactcgcat caaccaaacc gttattcatt cgtgattgcg    3840
cctgagcgag acgaaatacg cgatcgctgt taaaaggaca attacaaaca ggaatcgaat    3900
gcaaccggcg caggaacact gccagcgcat caacaatatt ttcacctgaa tcaggatatt    3960
cttctaatac ctggaatgct gttttcccgg ggatcgcagt ggtgagtaac catgcatcat    4020
caggagtacg gataaaatgc ttgatggtcg gaagaggcat aaattccgtc agccagttta    4080
gtctgaccat ctcatctgta acatcattgg caacgctacc tttgccatgt ttcagaaaca    4140
actctggcgc atcgggcttc ccatacaatc gatagattgt cgcacctgat tgcccgacat    4200
tatcgcgagc ccatttatac ccatataaat cagcatccat gttggaattt aatcgcggcc    4260
tcgagcaaga cgtttcccgt tgaatatggc tcataacacc ccttgtatta ctgtttatgt    4320
aagcagacag ttttattgtt catgatgata tatttttatc ttgtgcaatg taacatcaga    4380
gattttgaga cacaacgtgg ctttcccccc ccccccatta ttgaagcatt tatcagggtt    4440
attgtctcat gagcggatac atatttgaat gtatttagaa aaataaacaa ataggggttc    4500
cgcgcacatt tccccgaaaa gtgccacctg acgtctaaga aaccattatt atcatgacat    4560
taacctataa aaataggcgt atcacgaggc cctttcgtct cgcgcgtttc ggtgatgacg    4620
gtgaaaacct ctgacacatg cagctcccgg agacggtcac agcttgtctg taagcggatg    4680
ccgggagcag acaagcccgt cagggcgcgt cagcgggtgt tggcgggtgt cggggctggc    4740
ttaactatgc ggcatcagag cagattgtac tgagagtgca ccatatgcgg tgtgaaatac    4800
cgcacagatg cgtaaggaga aaataccgca tcagattggc tat                     4843
```

<210> SEQ ID NO 47
<211> LENGTH: 4843
<212> TYPE: DNA
<213> ORGANISM: Artificial Sequence
<220> FEATURE:
<223> OTHER INFORMATION: Synthetic primer

<400> SEQUENCE: 47

```
tggccattgc atacgttgta tccatatcat aaatatgtaca tttatattgg ctcatgtcca      60
acattaccgc catgttgaca ttgattattg actagttatt aatagtaatc aattacgggg     120
```

```
tcattagttc atagcccata tatggagttc cgcgttacat aacttacggt aaatggcccg      180
cctggctgac cgcccaacga cccccgccca ttgacgtcaa taatgacgta tgttcccata      240
gtaacgccaa tagggacttt ccattgacgt caatgggtgg agtatttacg gtaaactgcc      300
cacttggcag tacatcaagt gtatcatatg ccaagtacgc ccctattga cgtcaatgac       360 ggtaaatggc ccgcctggca ttatgcccag tacatgacct tatgggactt tcctacttgg      420
cagtacatct acgtattagt catcgctatt accatggtga tgcggttttg gcagtacatc      480
aatgggcgtg gatagcggtt tgactcacgg ggatttccaa gtctccaccc cattgacgtc      540
aatgggagtt tgttttggca ccaaaatcaa cgggactttc caaaatgtcg taacaactcc      600
gccccattga cgcaaatggg cggtaggcgt gtacggtggg aggtctatat aagcagagct      660
cgtttagtga accgtcagat cgcctggaga cgccatccac gctgttttga cctccataga      720
agacaccggg accgatccag cctccgcggc cgggaacggt gcattggaac gcggattccc      780
cgtgccaaga gtgacgtaag taccgcctat agactctata ggcacacccc tttggctctt      840
atgcatgcta tactgttttt ggcttggggc ctatacaccc ccgcttcctt atgctatagg      900
tgatggtata gcttagccta taggtgtggg ttattgacca ttattgacca ctccaacggt      960
ggagggcagt gtagtctgag cagtactcgt tgctgccgcg cgcgccacca gacataatag     1020
ctgacagact aacagactgt tcctttccat gggtcttttc tgcagtcacc gtcgtcgaca     1080
attatctatt tcaaatttag caggaaaaaa gagaacatca ccttgtaaaa ctgaagattg     1140
tgaccagtca gaataatgtg gaaatgatgc gacactatga tatgtgcatc tatactgtca     1200
tctcatttcc cattatggtg acagctgcct cgggaagcca agttgggctt taaagtgcag     1260
ggcctgctga tgttgagtgc ttttgttcg gaaatgagat gacagtatag tgaagtagat       1320
tagcatctat actgtcatct catttcccat aagaagttat gtattcatcc aataattcaa     1380
gccaagcaag tatataggtg ttttaatagt ttttgtttgc agtcctctgt tccagtgcac     1440
cattgataaa agaagaatgt agttttatca atggtgcact ggtggtggcc tgctatttcc     1500
ttcaaatgaa tgattttac taattttgtg tactttatt gtgtcgatgt agaatctgcc        1560
tggtctatct gatgtgacag cttctgtagc acccagtgca tgcttgataa agtgtttagt     1620
tatcttttat caatggtgca ctggtactgc tagctgtaga actccagctt cggcctgtcg     1680
cccaatcaaa ctgtcctgtt actgaacact gttctatggt ttctctctga atcactaag       1740 tgtgtgatat tctgccttag tgatttcaga gagactgtgg tagtgaaaag tctgtagaaa     1800
agtaagggaa actcaaaccc cttctacac tctctctgct gtcacttagg tgtttctgta       1860
tggcttagtg atttcagaga gatgagtttg gtggggattg tgaccagaag attttgaaaa     1920
ttaaatatta ctgaagattt cgacttcgcg gccgcggatc cagatctttt tccctctgcc     1980
aaaaattatg gggacatcat gaagcccctt gagcatctga cttctggcta ataaaggaaa     2040
tttattttca ttgcaatagt gtgttggaat ttttgtgtc tctcactcgg aaggacatat       2100
gggagggcaa atcatttaaa acatcagaat gagtatttgg tttagagttt ggcaacatat     2160
gcccattctt ccgcttcctc gctcactgac tcgctgcgct cggtcgttcg gctgcggcga     2220
gcggtatcag ctcactcaaa ggcggtaata cggttatcca cagaatcagg gataacgca      2280 ggaaagaaca tgtgagcaaa aggccagcaa aaggccagga accgtaaaaa ggccgcgttg     2340
ctggcgtttt tccataggct ccgccccct gacgagcatc acaaaaatcg acgctcaagt      2400
cagaggtggc gaaacccgac aggactataa agataccagg cgtttccccc tggaagctcc     2460
ctcgtgcgct ctcctgttcc gaccctgccg cttaccggat acctgtccgc ctttctccct     2520
```

```
tcgggaagcg tggcgctttc tcatagctca cgctgtaggt atctcagttc ggtgtaggtc   2580
gttcgctcca agctgggctg tgtgcacgaa ccccccgttc agcccgaccg ctgcgcctta   2640
tccggtaact atcgtcttga gtccaacccg gtaagacacg acttatcgcc actggcagca   2700
gccactggta acaggattag cagagcgagg tatgtaggcg gtgctacaga gttcttgaag   2760
tggtggccta actacggcta cactagaaga acagtatttg gtatctgcgc tctgctgaag   2820
ccagttacct tcggaaaaag agttggtagc tcttgatccg gcaaacaaac caccgctggt   2880
agcggtggtt ttttttgttg caagcagcag attacgcgca gaaaaaaagg atctcaagaa   2940
gatcctttga tcttttctac ggggtctgac gctcagtgga acgaaaactc acgttaaggg   3000
attttggtca tgagattatc aaaaaggatc ttcacctaga tccttttaaa ttaaaaatga   3060
agttttaaat caatctaaag tatatatgag taaacttggt ctgacagtta ccaatgctta   3120
atcagtgagg cacctatctc agcgatctgt ctatttcgtt catccatagt tgcctgactc   3180
gggggggggg ggcgctgagg tctgcctcgt gaagaaggtg ttgctgactc ataccaggcc   3240
tgaatcgccc catcatccag ccagaaagtg agggagccac ggttgatgag agctttgttg   3300
taggtggacc agttggtgat tttgaacttt tgctttgcca cggaacggtc tgcgttgtcg   3360
ggaagatgcg tgatctgatc cttcaactca gcaaaagttc gatttattca acaaagccgc   3420
cgtcccgtca gtcagcgta atgctctgcc agtgttacaa ccaattaacc aattctgatt   3480
agaaaaactc atcgagcatc aaatgaaact gcaatttatt catatcagga ttatcaatac   3540 catattttg aaaaagccgt ttctgtaatg aaggagaaaa ctcaccgagg cagttccata   3600
ggatggcaag atcctggtat cggtctgcga ttccgactcg tccaacatca atacaaccta   3660
ttaatttccc ctcgtcaaaa ataaggttat caagtgagaa atcaccatga gtgacgactg   3720
aatccggtga gaatggcaaa agcttatgca tttctttcca gacttgttca acaggccagc   3780
cattacgctc gtcatcaaaa tcactcgcat caaccaaacc gttattcatt cgtgattgcg   3840
cctgagcgag acgaaatacg cgatcgctgt taaaaggaca attacaaaca ggaatcgaat   3900
gcaaccggcg caggaacact gccagcgcat caacaatatt ttcacctgaa tcaggatatt   3960
cttctaatac ctggaatgct gttttcccgg ggatcgcagt ggtgagtaac catgcatcat   4020
caggagtacg gataaaatgc ttgatggtcg gaagaggcat aaattccgtc agccagttta   4080
gtctgaccat ctcatctgta acatcattgg caacgctacc tttgccatgt ttcagaaaca   4140
actctggcgc atcgggcttc ccatacaatc gatagattgt cgcacctgat tgcccgacat   4200
tatcgcgagc ccatttatac ccatataaat cagcatccat gttggaattt aatcgcggcc   4260
tcgagcaaga cgtttcccgt tgaatatggc tcataacacc ccttgtatta ctgtttatgt   4320
aagcagacag ttttattgtt catgatgata tatttttatc ttgtgcaatg taacatcaga   4380
gattttgaga cacaacgtgg ctttcccccc cccccatta ttgaagcatt tatcagggtt   4440
attgtctcat gagcggatac atatttgaat gtatttagaa aaataaacaa ataggggttc   4500
cgcgcacatt tccccgaaaa gtgccacctg acgtctaaga aaccattatt atcatgacat   4560
taacctataa aaataggcgt atcacgaggc cctttcgtct cgcgcgtttc ggtgatgacg   4620
gtgaaaacct ctgacacatg cagctcccgg agacggtcac agcttgtctg taagcggatg   4680
ccgggagcag acaagcccgt cagggcgcgt cagcgggtgt tggcgggtgt cggggctggc   4740
ttaactatgc ggcatcagag cagattgtac tgagagtgca ccatatgcgg tgtgaaatac   4800
cgcacagatg cgtaaggaga aaataccgca tcagattggc tat           4843
```

```
<210> SEQ ID NO 48
<211> LENGTH: 19
<212> TYPE: DNA
<213> ORGANISM: Artificial Sequence
<220> FEATURE:
<223> OTHER INFORMATION: Synthetic primer

<400> SEQUENCE: 48
cacctgcgtg aagaagtgt                                               19

<210> SEQ ID NO 49
<211> LENGTH: 19
<212> TYPE: DNA
<213> ORGANISM: Artificial Sequence
<220> FEATURE:
<223> OTHER INFORMATION: Synthetic primer

<400> SEQUENCE: 49
acacttcttc acgcaggtg                                               19

<210> SEQ ID NO 50
<211> LENGTH: 19
<212> TYPE: DNA
<213> ORGANISM: Artificial Sequence
<220> FEATURE:
<223> OTHER INFORMATION: Synthetic primer

<400> SEQUENCE: 50
gctgactaat ttgttctga                                               19

<210> SEQ ID NO 51
<211> LENGTH: 19
<212> TYPE: DNA
<213> ORGANISM: Artificial Sequence
<220> FEATURE:
<223> OTHER INFORMATION: Synthetic primer

<400> SEQUENCE: 51
ggcacaaatg gctgccaaa                                               19

<210> SEQ ID NO 52
<211> LENGTH: 19
<212> TYPE: DNA
<213> ORGANISM: Artificial Sequence
<220> FEATURE:
<223> OTHER INFORMATION: Synthetic primer

<400> SEQUENCE: 52
ggcgcaaatg gctgccaag                                               19

<210> SEQ ID NO 53
<211> LENGTH: 19
<212> TYPE: DNA
<213> ORGANISM: Artificial Sequence
<220> FEATURE:
<223> OTHER INFORMATION: Synthetic primer

<400> SEQUENCE: 53
aatcaaccta tcctccttc                                               19

<210> SEQ ID NO 54
<211> LENGTH: 19
<212> TYPE: DNA
<213> ORGANISM: Artificial Sequence
<220> FEATURE:
<223> OTHER INFORMATION: Synthetic primer
```

<400> SEQUENCE: 54
aaaatcaacc tatcctcct                                                  19

<210> SEQ ID NO 55
<211> LENGTH: 19
<212> TYPE: DNA
<213> ORGANISM: Artificial Sequence
<220> FEATURE:
<223> OTHER INFORMATION: Synthetic primer

<400> SEQUENCE: 55
gttttgatgt caatgacca                                                  19

<210> SEQ ID NO 56
<211> LENGTH: 19
<212> TYPE: DNA
<213> ORGANISM: Artificial Sequence
<220> FEATURE:
<223> OTHER INFORMATION: Synthetic primer

<400> SEQUENCE: 56
ggagaaagga gtgaaacct                                                  19

<210> SEQ ID NO 57
<211> LENGTH: 19
<212> TYPE: DNA
<213> ORGANISM: Artificial Sequence
<220> FEATURE:
<223> OTHER INFORMATION: Synthetic primer

<400> SEQUENCE: 57
cagctgcgct ctggcttta                                                  19

<210> SEQ ID NO 58
<211> LENGTH: 19
<212> TYPE: DNA
<213> ORGANISM: Artificial Sequence
<220> FEATURE:
<223> OTHER INFORMATION: Synthetic primer

<400> SEQUENCE: 58
agttcctatt caacaagta                                                  19

<210> SEQ ID NO 59
<211> LENGTH: 19
<212> TYPE: DNA
<213> ORGANISM: Artificial Sequence
<220> FEATURE:
<223> OTHER INFORMATION: Synthetic primer

<400> SEQUENCE: 59
cagttattta caaacaggt                                                  19

<210> SEQ ID NO 60
<211> LENGTH: 19
<212> TYPE: DNA
<213> ORGANISM: Artificial Sequence
<220> FEATURE:
<223> OTHER INFORMATION: Synthetic primer

<400> SEQUENCE: 60
ggaagataag aaacgtagt                                                  19

<210> SEQ ID NO 61

```
<211> LENGTH: 19
<212> TYPE: DNA
<213> ORGANISM: Artificial Sequence
<220> FEATURE:
<223> OTHER INFORMATION: Synthetic primer

<400> SEQUENCE: 61
ggaagggatg gcatagcgt                                                   19

<210> SEQ ID NO 62
<211> LENGTH: 19
<212> TYPE: DNA
<213> ORGANISM: Artificial Sequence
<220> FEATURE:
<223> OTHER INFORMATION: Synthetic primer

<400> SEQUENCE: 62
gcctcattta ccatcgttt                                                   19

<210> SEQ ID NO 63
<211> LENGTH: 19
<212> TYPE: DNA
<213> ORGANISM: Artificial Sequence
<220> FEATURE:
<223> OTHER INFORMATION: Synthetic primer

<400> SEQUENCE: 63
tggacaacga tggcctcta                                                   19

<210> SEQ ID NO 64
<211> LENGTH: 19
<212> TYPE: DNA
<213> ORGANISM: Artificial Sequence
<220> FEATURE:
<223> OTHER INFORMATION: Synthetic primer

<400> SEQUENCE: 64
gcctcatctt ctacaagaa                                                   19

<210> SEQ ID NO 65
<211> LENGTH: 19
<212> TYPE: DNA
<213> ORGANISM: Artificial Sequence
<220> FEATURE:
<223> OTHER INFORMATION: Synthetic primer

<400> SEQUENCE: 65
ccaggaccag caggaggca                                                   19

<210> SEQ ID NO 66
<211> LENGTH: 19
<212> TYPE: DNA
<213> ORGANISM: Artificial Sequence
<220> FEATURE:
<223> OTHER INFORMATION: Synthetic primer

<400> SEQUENCE: 66
acagcagcga ggtccctat                                                   19

<210> SEQ ID NO 67
<211> LENGTH: 19
<212> TYPE: DNA
<213> ORGANISM: Artificial Sequence
<220> FEATURE:
<223> OTHER INFORMATION: Synthetic primer

<400> SEQUENCE: 67
```
acgtagcact ctgcgacat                                                     19

<210> SEQ ID NO 68
<211> LENGTH: 19
<212> TYPE: DNA
<213> ORGANISM: Artificial Sequence
<220> FEATURE:
<223> OTHER INFORMATION: Synthetic primer

<400> SEQUENCE: 68
atggaaggta caggaatat                                                     19

<210> SEQ ID NO 69
<211> LENGTH: 19
<212> TYPE: DNA
<213> ORGANISM: Artificial Sequence
<220> FEATURE:
<223> OTHER INFORMATION: Synthetic primer

<400> SEQUENCE: 69
tcatgggaat tcatatcat                                                     19

<210> SEQ ID NO 70
<211> LENGTH: 19
<212> TYPE: DNA
<213> ORGANISM: Artificial Sequence
<220> FEATURE:
<223> OTHER INFORMATION: Synthetic primer

<400> SEQUENCE: 70
ccaccaatca gaaacagta                                                     19

<210> SEQ ID NO 71
<211> LENGTH: 19
<212> TYPE: DNA
<213> ORGANISM: Artificial Sequence
<220> FEATURE:
<223> OTHER INFORMATION: Synthetic primer

<400> SEQUENCE: 71
ggaggagatt gatagagcc                                                     19

<210> SEQ ID NO 72
<211> LENGTH: 19
<212> TYPE: DNA
<213> ORGANISM: Artificial Sequence
<220> FEATURE:
<223> OTHER INFORMATION: Synthetic primer

<400> SEQUENCE: 72
gttgtcaata tagatacaa                                                     19

<210> SEQ ID NO 73
<211> LENGTH: 19
<212> TYPE: DNA
<213> ORGANISM: Artificial Sequence
<220> FEATURE:
<223> OTHER INFORMATION: Synthetic primer

<400> SEQUENCE: 73
aaagcaaact cttccgaaa                                                     19

<210> SEQ ID NO 74
<211> LENGTH: 19
<212> TYPE: DNA

```
<213> ORGANISM: Artificial Sequence
<220> FEATURE:
<223> OTHER INFORMATION: Synthetic primer

<400> SEQUENCE: 74
gttgtcaata tagatacaa                                                    19

<210> SEQ ID NO 75
<211> LENGTH: 19
<212> TYPE: DNA
<213> ORGANISM: Artificial Sequence
<220> FEATURE:
<223> OTHER INFORMATION: Synthetic primer

<400> SEQUENCE: 75
gaggaagaac caggtcagt                                                    19

<210> SEQ ID NO 76
<211> LENGTH: 19
<212> TYPE: DNA
<213> ORGANISM: Artificial Sequence
<220> FEATURE:
<223> OTHER INFORMATION: Synthetic primer

<400> SEQUENCE: 76
aaagcaaact cttccgaaa                                                    19

<210> SEQ ID NO 77
<211> LENGTH: 19
<212> TYPE: DNA
<213> ORGANISM: Artificial Sequence
<220> FEATURE:
<223> OTHER INFORMATION: Synthetic primer

<400> SEQUENCE: 77
gaggaagaac caggtcagt                                                    19

<210> SEQ ID NO 78
<211> LENGTH: 19
<212> TYPE: DNA
<213> ORGANISM: Artificial Sequence
<220> FEATURE:
<223> OTHER INFORMATION: Synthetic primer

<400> SEQUENCE: 78
ggaaatgaga tgacagtat                                                    19

<210> SEQ ID NO 79
<211> LENGTH: 19
<212> TYPE: DNA
<213> ORGANISM: Artificial Sequence
<220> FEATURE:
<223> OTHER INFORMATION: Synthetic primer

<400> SEQUENCE: 79
cctatatggt agagcaata                                                    19

<210> SEQ ID NO 80
<211> LENGTH: 19
<212> TYPE: DNA
<213> ORGANISM: Artificial Sequence
<220> FEATURE:
<223> OTHER INFORMATION: Synthetic primer

<400> SEQUENCE: 80
gaagcaccat gattactac                                                    19
```

```
<210> SEQ ID NO 81
<211> LENGTH: 19
<212> TYPE: DNA
<213> ORGANISM: Artificial Sequence
<220> FEATURE:
<223> OTHER INFORMATION: Synthetic primer

<400> SEQUENCE: 81
cagccaggaa gcataggat                                                  19

<210> SEQ ID NO 82
<211> LENGTH: 19
<212> TYPE: DNA
<213> ORGANISM: Artificial Sequence
<220> FEATURE:
<223> OTHER INFORMATION: Synthetic primer

<400> SEQUENCE: 82
agaggaaggc aaacgtgac                                                  19

<210> SEQ ID NO 83
<211> LENGTH: 19
<212> TYPE: DNA
<213> ORGANISM: Artificial Sequence
<220> FEATURE:
<223> OTHER INFORMATION: Synthetic primer

<400> SEQUENCE: 83
caaacttgag gaaatctat                                                  19

<210> SEQ ID NO 84
<211> LENGTH: 19
<212> TYPE: DNA
<213> ORGANISM: Artificial Sequence
<220> FEATURE:
<223> OTHER INFORMATION: Synthetic primer

<400> SEQUENCE: 84
tggaggtgtg tgaagtcta                                                  19

<210> SEQ ID NO 85
<211> LENGTH: 19
<212> TYPE: DNA
<213> ORGANISM: Artificial Sequence
<220> FEATURE:
<223> OTHER INFORMATION: Synthetic primer

<400> SEQUENCE: 85
agaggaaggc aaacgtgac                                                  19

<210> SEQ ID NO 86
<211> LENGTH: 19
<212> TYPE: DNA
<213> ORGANISM: Artificial Sequence
<220> FEATURE:
<223> OTHER INFORMATION: Synthetic primer

<400> SEQUENCE: 86
tgttttgtaa gtgctgcta                                                  19

<210> SEQ ID NO 87
<211> LENGTH: 19
<212> TYPE: DNA
<213> ORGANISM: Artificial Sequence
<220> FEATURE:
```

```
<223> OTHER INFORMATION: Synthetic primer

<400> SEQUENCE: 87
gttggagctg atggcgtag                                              19

<210> SEQ ID NO 88
<211> LENGTH: 19
<212> TYPE: DNA
<213> ORGANISM: Artificial Sequence
<220> FEATURE:
<223> OTHER INFORMATION: Synthetic primer

<400> SEQUENCE: 88
ttggagctga tggcgtagg                                              19

<210> SEQ ID NO 89
<211> LENGTH: 19
<212> TYPE: DNA
<213> ORGANISM: Artificial Sequence
<220> FEATURE:
<223> OTHER INFORMATION: Synthetic primer

<400> SEQUENCE: 89
tggagctgat ggcgtaggc                                              19

<210> SEQ ID NO 90
<211> LENGTH: 19
<212> TYPE: DNA
<213> ORGANISM: Artificial Sequence
<220> FEATURE:
<223> OTHER INFORMATION: Synthetic primer

<400> SEQUENCE: 90
gttggagctg atggcgtag                                              19

<210> SEQ ID NO 91
<211> LENGTH: 19
<212> TYPE: DNA
<213> ORGANISM: Artificial Sequence
<220> FEATURE:
<223> OTHER INFORMATION: Synthetic primer

<400> SEQUENCE: 91
ttggagctga tggcgtagg                                              19

<210> SEQ ID NO 92
<211> LENGTH: 19
<212> TYPE: DNA
<213> ORGANISM: Artificial Sequence
<220> FEATURE:
<223> OTHER INFORMATION: Synthetic primer

<400> SEQUENCE: 92
tggagctgat ggcgtaggc                                              19

<210> SEQ ID NO 93
<211> LENGTH: 19
<212> TYPE: DNA
<213> ORGANISM: Artificial Sequence
<220> FEATURE:
<223> OTHER INFORMATION: Synthetic primer

<400> SEQUENCE: 93
gttggagctg atggcgtag                                              19
```

```
<210> SEQ ID NO 94
<211> LENGTH: 19
<212> TYPE: DNA
<213> ORGANISM: Artificial Sequence
<220> FEATURE:
<223> OTHER INFORMATION: Synthetic primer

<400> SEQUENCE: 94
ttggagctga tggcgtagg                                                    19

<210> SEQ ID NO 95
<211> LENGTH: 19
<212> TYPE: DNA
<213> ORGANISM: Artificial Sequence
<220> FEATURE:
<223> OTHER INFORMATION: Synthetic primer

<400> SEQUENCE: 95
tggagctgat ggcgtaggc                                                    19

<210> SEQ ID NO 96
<211> LENGTH: 19
<212> TYPE: DNA
<213> ORGANISM: Artificial Sequence
<220> FEATURE:
<223> OTHER INFORMATION: Synthetic primer

<400> SEQUENCE: 96
ggcctttcac tactcctac                                                    19

<210> SEQ ID NO 97
<211> LENGTH: 19
<212> TYPE: DNA
<213> ORGANISM: Artificial Sequence
<220> FEATURE:
<223> OTHER INFORMATION: Synthetic primer

<400> SEQUENCE: 97
gagcgaagag ggcgagaaa                                                    19

<210> SEQ ID NO 98
<211> LENGTH: 19
<212> TYPE: DNA
<213> ORGANISM: Artificial Sequence
<220> FEATURE:
<223> OTHER INFORMATION: Synthetic primer

<400> SEQUENCE: 98
tgtggtagtt ggagctgat                                                    19

<210> SEQ ID NO 99
<211> LENGTH: 19
<212> TYPE: DNA
<213> ORGANISM: Artificial Sequence
<220> FEATURE:
<223> OTHER INFORMATION: Synthetic primer

<400> SEQUENCE: 99
gtggtagttg gagctgatg                                                    19

<210> SEQ ID NO 100
<211> LENGTH: 19
<212> TYPE: DNA
<213> ORGANISM: Artificial Sequence
<220> FEATURE:
<223> OTHER INFORMATION: Synthetic primer
```

<400> SEQUENCE: 100
tggtagttgg agctgatgg                                                19

<210> SEQ ID NO 101
<211> LENGTH: 19
<212> TYPE: DNA
<213> ORGANISM: Artificial Sequence
<220> FEATURE:
<223> OTHER INFORMATION: Synthetic primer

<400> SEQUENCE: 101
ggtagttgga gctgatggc                                                19

<210> SEQ ID NO 102
<211> LENGTH: 19
<212> TYPE: DNA
<213> ORGANISM: Artificial Sequence
<220> FEATURE:
<223> OTHER INFORMATION: Synthetic primer

<400> SEQUENCE: 102
gtagttggag ctgatggcg                                                19

<210> SEQ ID NO 103
<211> LENGTH: 19
<212> TYPE: DNA
<213> ORGANISM: Artificial Sequence
<220> FEATURE:
<223> OTHER INFORMATION: Synthetic primer

<400> SEQUENCE: 103
tagttggagc tgatggcgt                                                19

<210> SEQ ID NO 104
<211> LENGTH: 19
<212> TYPE: DNA
<213> ORGANISM: Artificial Sequence
<220> FEATURE:
<223> OTHER INFORMATION: Synthetic primer

<400> SEQUENCE: 104
agttggagct gatggcgta                                                19

<210> SEQ ID NO 105
<211> LENGTH: 19
<212> TYPE: DNA
<213> ORGANISM: Artificial Sequence
<220> FEATURE:
<223> OTHER INFORMATION: Synthetic primer

<400> SEQUENCE: 105
gtggtagttg gagctgatg                                                19

<210> SEQ ID NO 106
<211> LENGTH: 19
<212> TYPE: DNA
<213> ORGANISM: Artificial Sequence
<220> FEATURE:
<223> OTHER INFORMATION: Synthetic primer

<400> SEQUENCE: 106
gtggtagttg gagctgatg                                                19

<210> SEQ ID NO 107
<211> LENGTH: 19

```
<212> TYPE: DNA
<213> ORGANISM: Artificial Sequence
<220> FEATURE:
<223> OTHER INFORMATION: Synthetic primer

<400> SEQUENCE: 107
gtggtagttg gagctgatg                                               19

<210> SEQ ID NO 108
<211> LENGTH: 19
<212> TYPE: DNA
<213> ORGANISM: Artificial Sequence
<220> FEATURE:
<223> OTHER INFORMATION: Synthetic primer

<400> SEQUENCE: 108
tggtagttgg agctgatgg                                               19

<210> SEQ ID NO 109
<211> LENGTH: 19
<212> TYPE: DNA
<213> ORGANISM: Artificial Sequence
<220> FEATURE:
<223> OTHER INFORMATION: Synthetic primer

<400> SEQUENCE: 109
tggtagttgg agctgatgg                                               19

<210> SEQ ID NO 110
<211> LENGTH: 19
<212> TYPE: DNA
<213> ORGANISM: Artificial Sequence
<220> FEATURE:
<223> OTHER INFORMATION: Synthetic primer

<400> SEQUENCE: 110
gtggtagttg gagctgttg                                               19

<210> SEQ ID NO 111
<211> LENGTH: 19
<212> TYPE: DNA
<213> ORGANISM: Artificial Sequence
<220> FEATURE:
<223> OTHER INFORMATION: Synthetic primer

<400> SEQUENCE: 111
tggtagttgg agctgttgg                                               19

<210> SEQ ID NO 112
<211> LENGTH: 19
<212> TYPE: DNA
<213> ORGANISM: Artificial Sequence
<220> FEATURE:
<223> OTHER INFORMATION: Synthetic primer

<400> SEQUENCE: 112
gtggtagttg gagctgttg                                               19

<210> SEQ ID NO 113
<211> LENGTH: 19
<212> TYPE: DNA
<213> ORGANISM: Artificial Sequence
<220> FEATURE:
<223> OTHER INFORMATION: Synthetic primer

<400> SEQUENCE: 113
```

-continued tggtagttgg agctgttgg                                              19

<210> SEQ ID NO 114
<211> LENGTH: 19
<212> TYPE: DNA
<213> ORGANISM: Artificial Sequence
<220> FEATURE:
<223> OTHER INFORMATION: Synthetic primer

<400> SEQUENCE: 114
tgtggtagtt ggagctcgt                                              19

<210> SEQ ID NO 115
<211> LENGTH: 19
<212> TYPE: DNA
<213> ORGANISM: Artificial Sequence
<220> FEATURE:
<223> OTHER INFORMATION: Synthetic primer

<400> SEQUENCE: 115
tgtggtagtt ggagcttgt                                              19

<210> SEQ ID NO 116
<211> LENGTH: 19
<212> TYPE: DNA
<213> ORGANISM: Artificial Sequence
<220> FEATURE:
<223> OTHER INFORMATION: Synthetic primer

<400> SEQUENCE: 116
gtggtagttg gagctcgtg                                              19

<210> SEQ ID NO 117
<211> LENGTH: 19
<212> TYPE: DNA
<213> ORGANISM: Artificial Sequence
<220> FEATURE:
<223> OTHER INFORMATION: Synthetic primer

<400> SEQUENCE: 117
gtggtagttg gagcttgtg                                              19

<210> SEQ ID NO 118
<211> LENGTH: 19
<212> TYPE: DNA
<213> ORGANISM: Artificial Sequence
<220> FEATURE:
<223> OTHER INFORMATION: Synthetic primer

<400> SEQUENCE: 118
cagaaatgat tgcactatt                                              19

<210> SEQ ID NO 119
<211> LENGTH: 19
<212> TYPE: DNA
<213> ORGANISM: Artificial Sequence
<220> FEATURE:
<223> OTHER INFORMATION: Synthetic primer

<400> SEQUENCE: 119
cagcctgttg aactcttct                                              19

<210> SEQ ID NO 120
<211> LENGTH: 19
<212> TYPE: DNA
<213> ORGANISM: Artificial Sequence -continued

```
<220> FEATURE:
<223> OTHER INFORMATION: Synthetic primer

<400> SEQUENCE: 120
acgaggcagc tgcgtacca                                              19

<210> SEQ ID NO 121
<211> LENGTH: 19
<212> TYPE: DNA
<213> ORGANISM: Artificial Sequence
<220> FEATURE:
<223> OTHER INFORMATION: Synthetic primer

<400> SEQUENCE: 121
gcaggaagca gtatccgaa                                              19

<210> SEQ ID NO 122
<211> LENGTH: 19
<212> TYPE: DNA
<213> ORGANISM: Artificial Sequence
<220> FEATURE:
<223> OTHER INFORMATION: Synthetic primer

<400> SEQUENCE: 122
ctacgggcag cagaaccct                                              19

<210> SEQ ID NO 123
<211> LENGTH: 19
<212> TYPE: DNA
<213> ORGANISM: Artificial Sequence
<220> FEATURE:
<223> OTHER INFORMATION: Synthetic primer

<400> SEQUENCE: 123
cgggcagcag agttcactg                                              19

<210> SEQ ID NO 124
<211> LENGTH: 18
<212> TYPE: DNA
<213> ORGANISM: Artificial Sequence
<220> FEATURE:
<223> OTHER INFORMATION: Synthetic primer

<400> SEQUENCE: 124
tcttgatcag acccttct                                               18

<210> SEQ ID NO 125
<211> LENGTH: 19
<212> TYPE: DNA
<213> ORGANISM: Artificial Sequence
<220> FEATURE:
<223> OTHER INFORMATION: Synthetic primer

<400> SEQUENCE: 125
agatcttgat ctaggttca                                              19

<210> SEQ ID NO 126
<211> LENGTH: 19
<212> TYPE: DNA
<213> ORGANISM: Artificial Sequence
<220> FEATURE:
<223> OTHER INFORMATION: Synthetic primer

<400> SEQUENCE: 126
ctacgggcag cagaattta                                              19
```

UNITED STATES PATENT AND TRADEMARK OFFICE
CERTIFICATE OF CORRECTION

| | |
|---|---|
| PATENT NO. | : 9,683,237 B2 |
| APPLICATION NO. | : 14/696144 |
| DATED | : June 20, 2017 |
| INVENTOR(S) | : Donald Rao et al. |

It is certified that error appears in the above-identified patent and that said Letters Patent is hereby corrected as shown below:

In the Claims

In Claim 5, Column 119, Line 31, delete the word "s" and insert --a-- therefor.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*